(12) United States Patent
Ge et al.

(10) Patent No.: US 10,933,059 B2
(45) Date of Patent: Mar. 2, 2021

(54) COMBINATION, APPLICATION THEREOF AND TREATMENT METHOD

(71) Applicant: KANGPU BIOPHARMACEUTICALS, LTD., Shanghai (CN)

(72) Inventors: Chuansheng Ge, Shanghai (CN); Baisong Liao, Shanghai (CN); Wen-Cherng Lee, Shanghai (CN)

(73) Assignee: KANGPU BIOPHARMACEUTICALS. LTD., Shanghai (CN)

( * ) Notice: Subject to any disclaimer, the term of this patent is extended or adjusted under 35 U.S.C. 154(b) by 0 days.

(21) Appl. No.: 16/468,385

(22) PCT Filed: Dec. 15, 2017

(86) PCT No.: PCT/CN2017/116413
§ 371 (c)(1),
(2) Date: Jun. 11, 2019

(87) PCT Pub. No.: WO2018/108147
PCT Pub. Date: Jun. 21, 2018

(65) Prior Publication Data
US 2019/0328722 A1   Oct. 31, 2019

(30) Foreign Application Priority Data
Dec. 16, 2016  (CN) .......................... 201611170723.1

(51) Int. Cl.
| A61K 31/454 | (2006.01) |
| A61K 31/58 | (2006.01) |
| A61K 31/573 | (2006.01) |
| A61K 31/4166 | (2006.01) |
| A61P 35/00 | (2006.01) |

(52) U.S. Cl.
CPC ........ *A61K 31/454* (2013.01); *A61K 31/4166* (2013.01); *A61K 31/573* (2013.01); *A61K 31/58* (2013.01); *A61P 35/00* (2018.01)

(58) Field of Classification Search
CPC .............. A61K 2300/00; A61K 31/167; A61K 31/277; A61K 31/4166; A61K 31/4188; A61K 31/454; A61K 31/5377; A61K 31/5685; A61K 31/57; A61K 31/573; A61K 31/58; A61K 31/585; A61K 38/09; A61P 35/00
See application file for complete search history.

(56) References Cited

FOREIGN PATENT DOCUMENTS

| CN | 102822165 A | 12/2012 |
| CN | 106551934 A | 4/2017 |
| JP | 2015-531590 A | 11/2015 |
| WO | 02/059106 A1 | 8/2002 |
| WO | 02059106 A1 | 8/2002 |
| WO | 2008/115516 A2 | 9/2008 |
| WO | 2011100380 A1 | 8/2011 |
| WO | 2013/079964 A1 | 6/2013 |
| WO | 2014018926 A1 | 1/2014 |
| WO | 2014/113260 A1 | 7/2014 |
| WO | 2014/179867 A1 | 11/2014 |
| WO | 2016065980 A1 | 5/2016 |
| WO | WO 2016/065980 | * 6/2016 ........... C07D 401/04 |
| WO | 2017067530 A2 | 4/2017 |

OTHER PUBLICATIONS

International Search Report dated Mar. 14, 2018 from the International Searching Authority in corresponding International application No. PCT/CN2017/116413.
Written Opinion dated Mar. 14, 2018 from the International Searching Authority in corresponding International application No. PCT/CN2017/116413.
Tannock, I., et al., "Docetaxel plus Prednisone or Mitoxantrone plus Prednisone for Advanced Prostate Cancer", The New England Journal of Medicine, vol. 351, No. 15, 2004, pp. 1502-1512 (11 pages).
Petrylak, D., et al., "Docetaxel and prednisone with or without lenalidomide in chemotherapy-naive patients with metastatic castration-resistant prostate cancer (MAINSAIL): a randomised, double-blind, placebo-controlled phase 3 trial", Lancet Oncology, vol. 16, No. 4, 2015, pp. 417-425 (9 pages).
Xing, D.-L., et al., "Lenalidomide in Treating Patients with Castration-Resistant Prostate Cancer", Asian Pacific Journal of Cancer Prevention, vol. 16, No. 9, 2015, pp. 3969-3972 (4 pages).
Stahl, P., et al., "Handbook of Pharmaceutical Salts: Properties, Selection, and Use", International Union of Pure and Applied Chemistry, Wiley-VCH, 2002, pp. 330-350 (25 pages).

(Continued)

*Primary Examiner* — Erich A Leeser
(74) *Attorney, Agent, or Firm* — Sughrue Mion, PLLC

(57) ABSTRACT

Provided are a combination, an application thereof and a treatment method. The combination comprises one or more of a benzoheterocyclic compound of formula (I), a pharmaceutically acceptable salt, a solvate, a crystalline form, a cocrystal, a stereoisomer, an isotope compound, a metabolite and a prodrug thereof, and an androgen receptor pathway modulator and/or a hormone drug. The combination and treatment method may effectively inhibit the growth of prostate cancer cells.

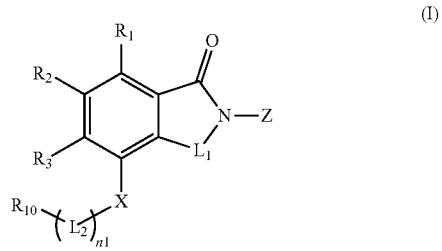

(I)

17 Claims, No Drawings

(56) References Cited

OTHER PUBLICATIONS

Rautio, J., et al., "Prodrugs: design and clinical applications", Nature Reviews: Drug Discovery, vol. 7, 2008, pp. 255-270 (16 pages).
Stella, V., et al., "Prodrugs: Challenges and Rewards Part 2 (Part 1)". Biotechnology: Pharmaceutical Aspects, Springer, 2007, pp. 4-33 (41 pages).
Communication (Office Action with Search Report) dated Apr. 13, 2020, from the Federal Service for Intellectual Property of Russia in Application No. 2019121794/04.
Communication dated Sep. 15, 2020 by the Japan Patent Office in application No. 2019-529888.

* cited by examiner

COMBINATION, APPLICATION THEREOF AND TREATMENT METHOD

The present application is a National Stage of International Application No. PCT/CN2017/116413 filed Dec. 15, 2017, claiming the benefit of Chinese Patent Application No. CN201611170723.1 filed on Dec. 16, 2016, the contents of which are incorporated herein by reference in their entireties.

FIELD OF INVENTION

The present invention relates to a combination, an application thereof and a treatment method.

BACKGROUND ART

Prostate cancer is a common malignancy in the male reproductive system. The statistics which was made by the International Agency for Research on Cancer of World Health Organization in 2012 showed that the number of newly diagnosed prostate cancer patients in the world was 1.1 million in that year, accounting for about 15% of the total number of new cancer cases, making it the second most common cancer in men worldwide. In the United States, the incidence of prostate cancer ranks first in all malignancies, with the second highest mortality rate, second only to lung cancer. Although the incidence of prostate cancer in China is much lower than that in western countries, it has shown a significant growth trend in recent years and ranks first among male urological tumors, and most of prostate cancer were diagnosed in the terminal stage.

The growth of the prostate cancer cells requires the supporting of androgens including testosterone. Therefore, the targeted treatment strategies for prostate cancer mainly focus on the synthesis of androgen and the binding to the androgen receptor thereof. For example, Enzalutamide, a prostate cancer drug marketed by the U.S. FDA in August 2012, is a small molecule androgen receptor antagonist, which finally inhibits the androgen receptor pathway by competitive inhibition of the binding of androgen to its receptor, thereby achieving the effect of treating castration-resistant prostate cancer.

Enzalutamide also shows some side effects in clinical studies, such as weakness or fatigue, lumbago, diarrhea, joint pain, hot flashes, tissue swelling, musculoskeletal pain, headache, upper respiratory tract infection, dizziness, spinal cord compression and cauda equina syndrome, muscle weakness, dyscoimesis, lower respiratory tract infection, hematuria, tingling, anxiety and hypertension and so on.

For the treatment of cancer, the drug combination is often used in the clinical practice to improve the treatment effect, for example, the combination of docetaxel and prednisone for use in the treatment of prostate cancer. However, people have met great setbacks when exploring new combination regimens. One of the typical examples is that although the combination of docetaxel and prednisone can treat prostate cancer (Tannock et al. *N. Eng. J. Med.* (2004), 351, 1502-1512), the combination regimen of docetaxel, prednisone and lenalidomide failed in a Phase III clinical trial involving more than 1000 prostate cancer patients (Petrylak et al. *Lancet Oncol.* (2015) 16-4, 417-425). It should also be noted that, the results of several phase II clinical studies also indicated that the clinical efficacy of lenalidomide alone in the treatment of prostate cancer was not satisfying (Xing et al. *Asian Pac. J. Cancer Prev.* (2015) 16-9, 3969-3972). Therefore, it has become an urgent technical problem to be solved in the art to explore combination regimens of anti-prostate cancer drugs (including Enzalutamide etc.) to improve the efficacy and reduce the toxic and side effect.

Content of the Present Invention

The technical problem to be solved in the present invention is to improve the efficacy of the present anti-prostate cancer drugs to achieve better clinical application effects. The present invention provides a combination, application thereof and treatment method. The combination and treatment method of the present invention can inhibit the growth of prostate cancer cells more effectively.

The present invention provides a combination, comprising one or more of the benzoheterocyclic compound of formula (I), the pharmaceutically acceptable salt, solvate, polymorph, co-crystal, stereoisomer, isotope compound, metabolite and prodrug thereof, and the androgen receptor pathway modulator;

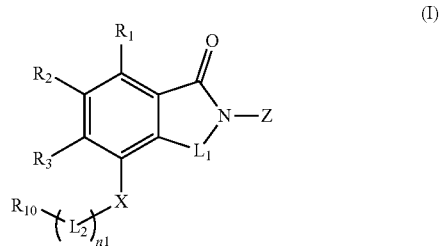

in formula (I), n1 is 0 or 1;
$L_1$ and $L_2$ are independently $CH_2$, CHD or $CD_2$;
X is NH, ND or O;
$R_1$ and $R_3$ are independently H or D;
$R_2$ is H, D or halogen;
Z is

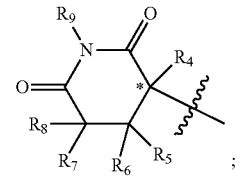

wherein, $R_4$ is H, D, $CH_3$, $CH_2D$, $CHD_2$ or $CD_3$; $R_5$, $R_6$, $R_7$, $R_8$ and $R_9$ are independently H or D; the carbon marked with * is an asymmetric center;
$R_{10}$ is H, D or

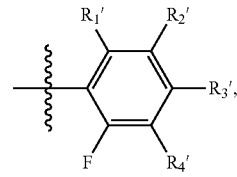

wherein, $R_1'$, $R_2'$, $R_3'$ and $R_4'$ are independently H, D, halogen, cyano, hydroxyl, substituted or unsubstituted ($C_1$-$C_{12}$) alkyl, substituted or unsubstituted ($C_1$-$C_{12}$) alkoxy, ($C_2$-$C_{20}$) heterocycloalkyl or deuterated $C_2$-$C_{20}$ heterocycloalkyl;

the substituent in the substituted ($C_1$-$C_{12}$) alkoxy is one or more of the following groups: D, halogen, hydroxyl, ($C_1$-

$C_{12}$) alkoxy, ($C_2$-$C_{20}$) heterocycloalkyl and ($C_2$-$C_{20}$) heterocycloalkyl substituted by ($C_1$-$C_{12}$) alkyl;

the substituent in the substituted ($C_1$-$C_{12}$) alkyl is one or more of the following groups: D, ($C_2$-$C_{20}$) heterocycloalkyl, deuterated ($C_2$-$C_{20}$) heterocycloalkyl, ($C_2$-$C_{20}$) heterocycloalkyl substituted by ($C_1$-$C_{12}$) alkyl and ($C_2$-$C_{20}$) heterocycloalkyl substituted by deuterated ($C_1$-$C_{12}$) alkyl;

when there are a plurality of substituents in the substituted ($C_1$-$C_{12}$) alkyl or the substituted ($C_1$-$C_{12}$) alkoxy, the substituents are the same or different;

in each of the above groups, the ($C_2$-$C_{20}$) heterocycloalkyl which is referred in the ($C_2$-$C_{20}$) heterocycloalkyl, deuterated ($C_2$-$C_{20}$) heterocycloalkyl, ($C_2$-$C_{20}$) heterocycloalkyl substituted by ($C_1$-$C_{12}$) alkyl and ($C_2$-$C_{20}$) heterocycloalkyl substituted by deuterated ($C_1$-$C_{12}$) alkyl is independently a ($C_2$-$C_{20}$) heterocycloalkyl wherein the heteroatom is one or more of O, N and S;

in the general formula (I), when n1 is 0, X is NH or ND, $R_{10}$ is H or D, then $R_2$ is F;

in the general formula (I), when n1 is 1, then $R_{10}$ is

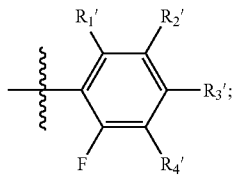

D represents deuterium-enriched hydrogen, and H represents non-deuterium-enriched hydrogen;

the androgen receptor pathway modulator is one or more of Enzalutamide, ARN-509, ODM-201, VT-464, Orteronel, EPI-001, Andarine, RD162, BMS-641988, CH5137291, Flutamide, Hydroxy flutamide, RU58642, LG120907, LG105, Galeterone, Spironolactone, MK-2866, AZD3514, Cyproterone acetate, ORM-15341, Bicalutamide, Nilutamide, Degarelix, Goserelin acetate, Leuprolide acetat, Abiraterone and Abiraterone Acetate;

when the androgen receptor pathway modulator is selected from one of the above compounds, the androgen receptor pathway modulator is not Bicalutamide, Nilutamide, Leuprolide acetate, Cyproterone acetate or Spironolactone.

In the formula (I), the asymmetric center preferably refers to (S)-configured carbon, (R)-configured carbon or racemate.

In the formula (I), the Z is preferably any one of the following structures:

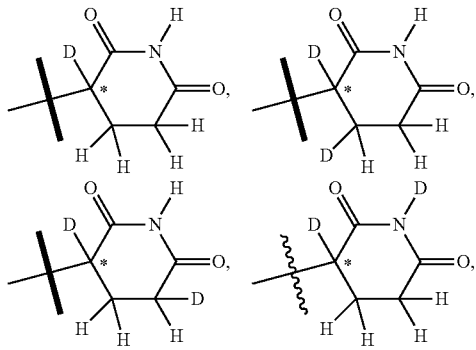
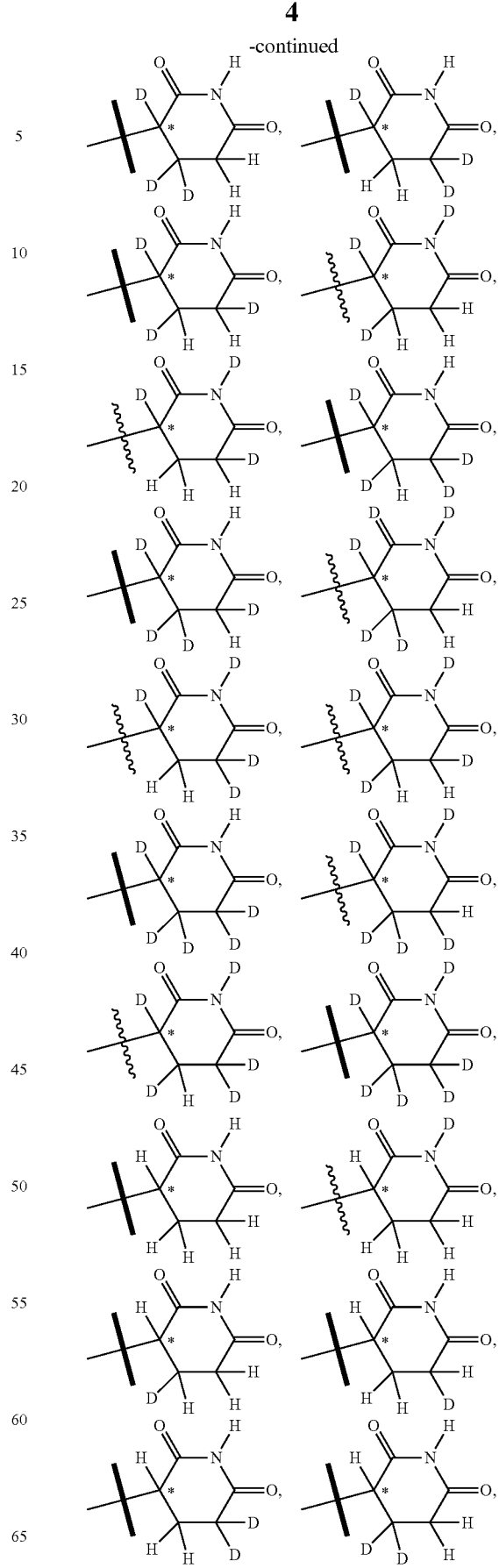

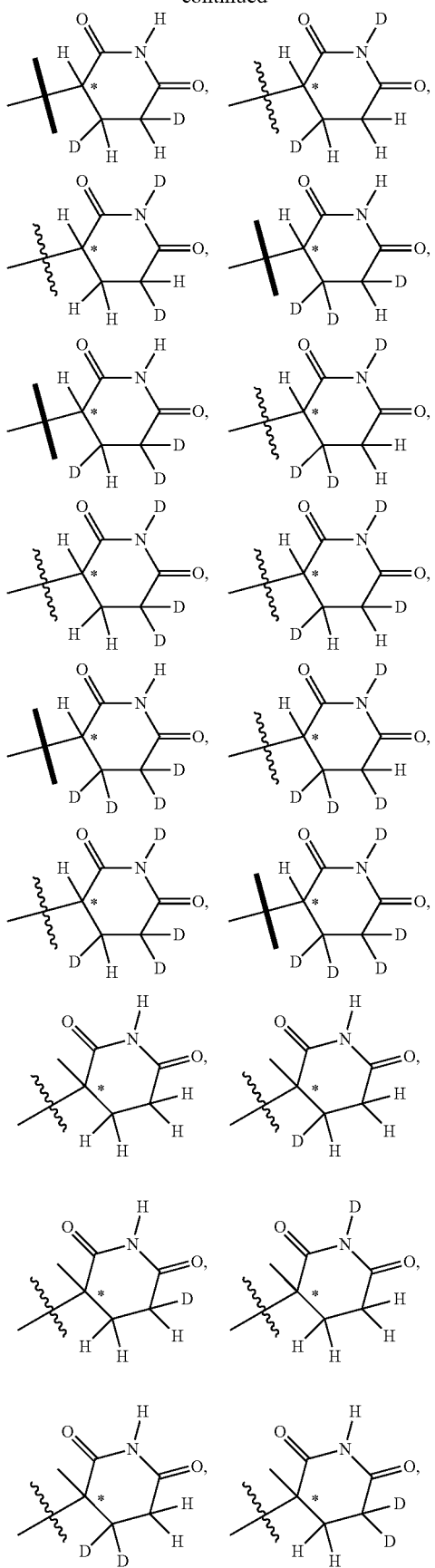
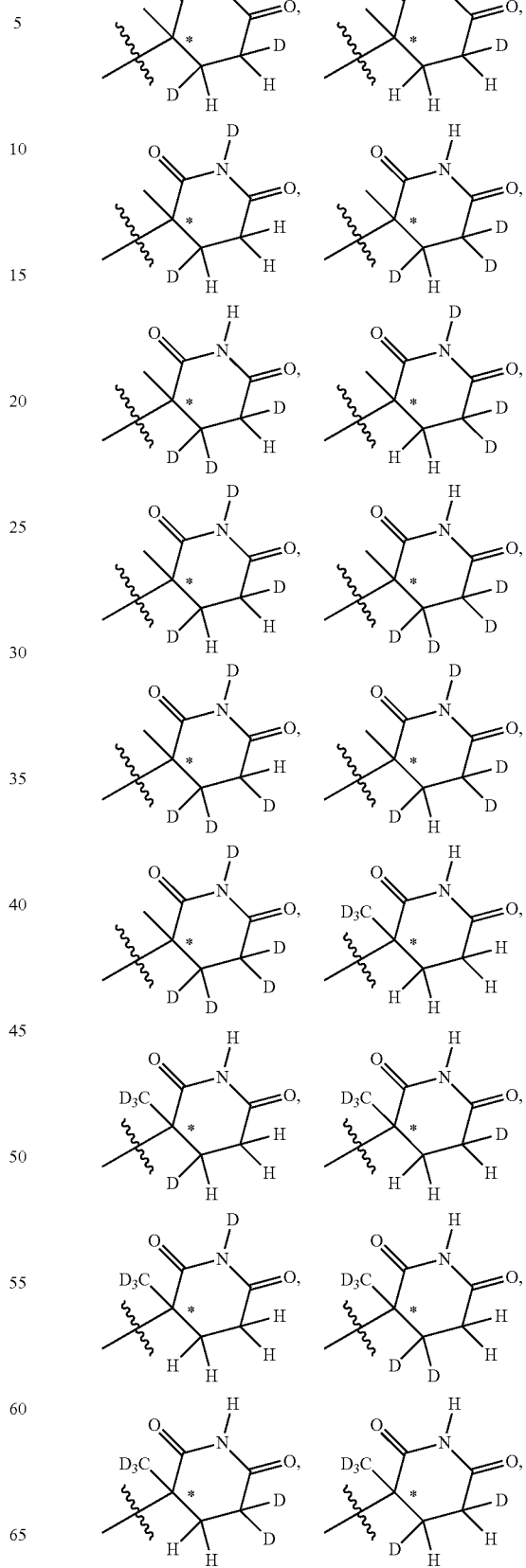

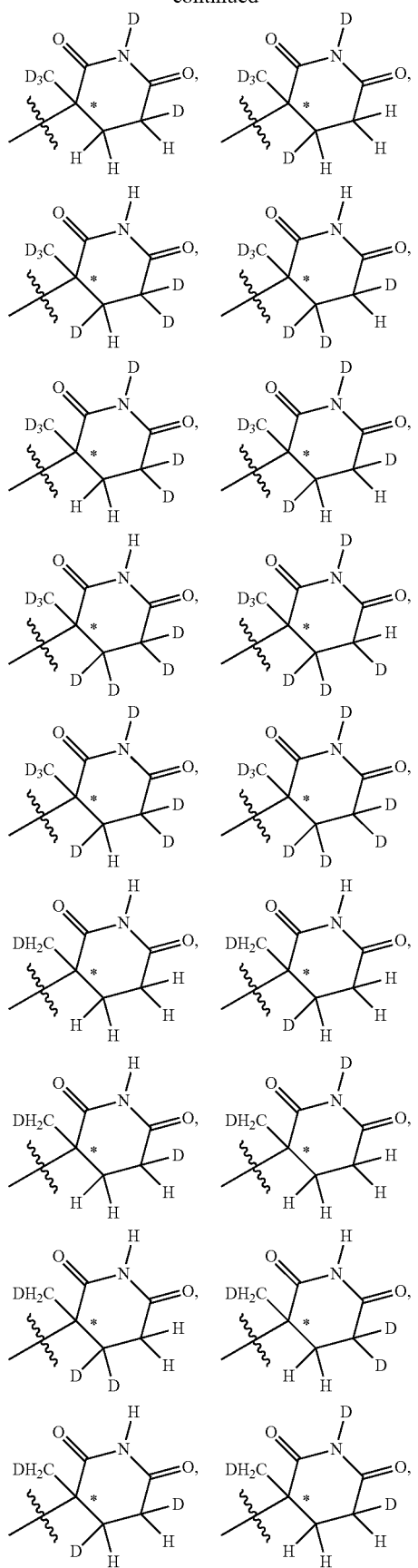
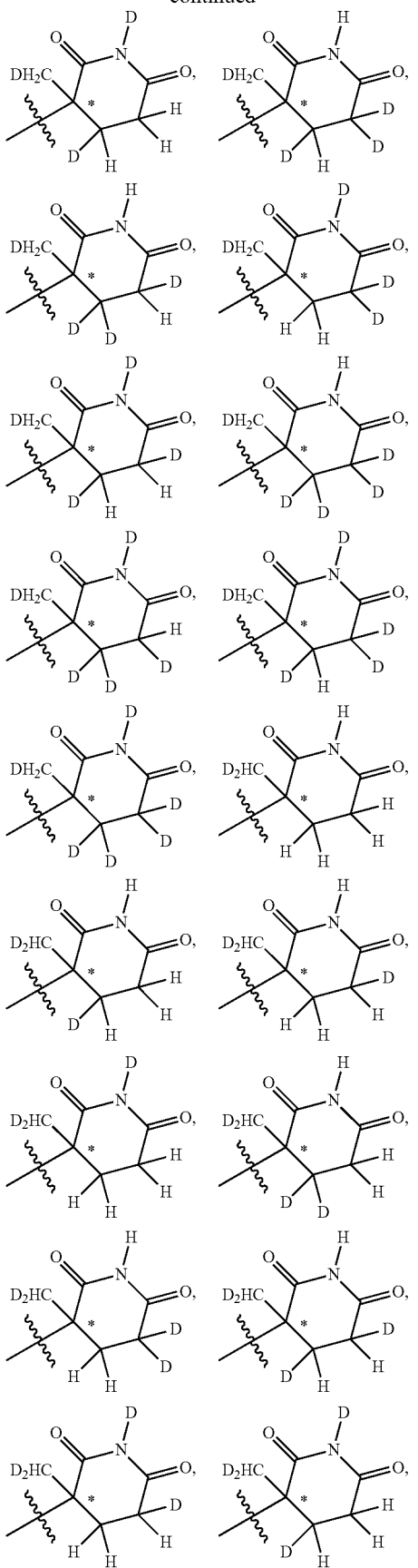

-continued

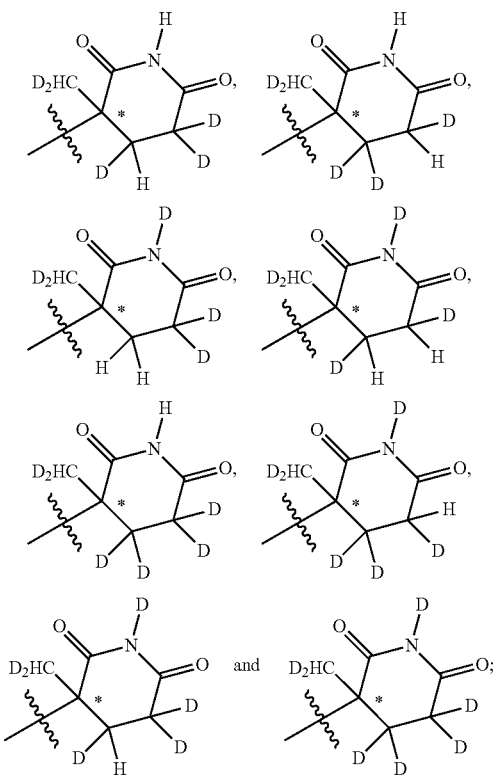

In some embodiments of the invention, Z is more preferably any one of the following structures

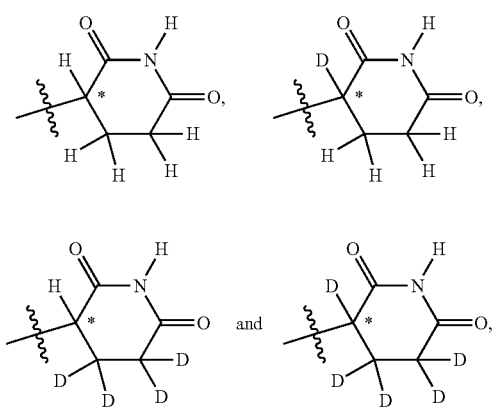

wherein, the carbon marked with * is an asymmetric center, and the asymmetric center, H and D are defined as described above.

In the formula (I), preferably, the $(C_2\text{-}C_{20})$ heterocycloalkyl which is referred in the $(C_2\text{-}C_{20})$ heterocycloalkyl, the deuterated $(C_2\text{-}C_{20})$ heterocycloalkyl, the $(C_2\text{-}C_{20})$ heterocycloalkyl substituted by $(C_1\text{-}C_{12})$ alkyl or the $(C_2\text{-}C_{20})$ heterocycloalkyl substituted by deuterated $(C_1\text{-}C_{12})$ alkyl independently refers to a $(C_2\text{-}C_6)$ heterocycloalkyl wherein the heteroatom is N or O and the number of heteroatoms is 1-2. The $(C_2\text{-}C_6)$ heterocycloalkyl wherein the heteroatom is N or O and the number of heteroatoms is 1-2 is preferably morpholinyl (e.g. 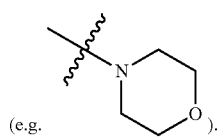 ).

In the formula (I), preferably, the $(C_1\text{-}C_{12})$ alkyl which is referred in the substituted or unsubstituted $(C_1\text{-}C_{12})$ alkyl, the $(C_2\text{-}C_{20})$ heterocycloalkyl substituted by $(C_1\text{-}C_{12})$ alkyl and the $(C_2\text{-}C_{20})$ heterocycloalkyl substituted by deuterated $(C_1\text{-}C_{12})$ alkyl is independently a $(C_1\text{-}C_4)$ alkyl. The $(C_1\text{-}C_4)$ alkyl is preferably methyl, ethyl, n-propyl, isopropyl, n-butyl, isobutyl, or tertiary-butyl. The substituted $(C_1\text{-}C_{12})$ alkyl is preferably

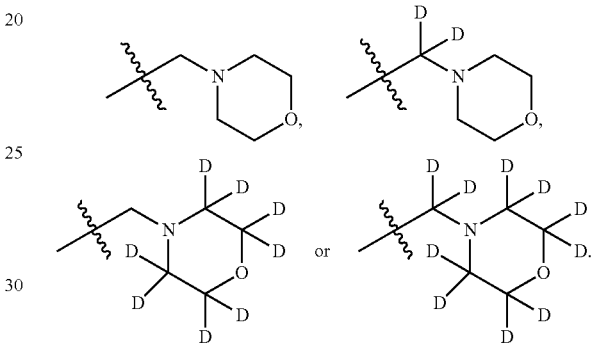

In the formula (I), preferably, the "$(C_1\text{-}C_{12})$ alkoxy" which is referred in the $(C_1\text{-}C_{12})$ alkoxy and the substituted or unsubstituted $(C_1\text{-}C_{12})$ alkoxy is independently a $(C_1\text{-}C_4)$ alkoxy; The $(C_1\text{-}C_4)$ alkoxy is preferably methoxy, ethoxy, n-propoxy, isopropoxy, n-butoxy, isobutoxy or tert-butoxy.

In the formula (I), the

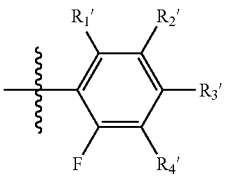

is preferably

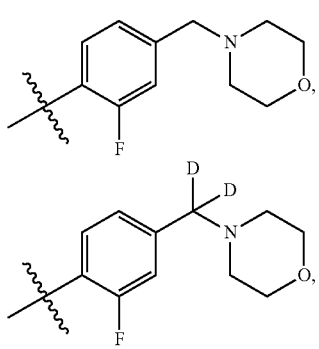

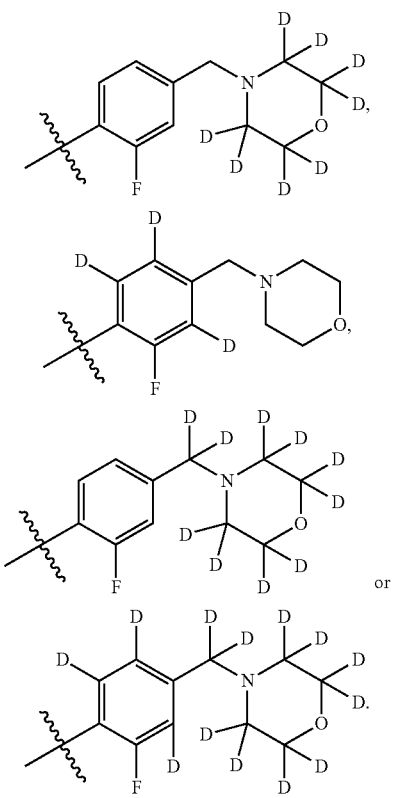
In the combination, the one or more of the benzoheterocyclic compound of formula (I), the pharmaceutically acceptable salt, solvate, polymorph, co-crystal, stereoisomer, isotope compound, metabolite and prodrug thereof is preferably any one of the following compounds:
B101
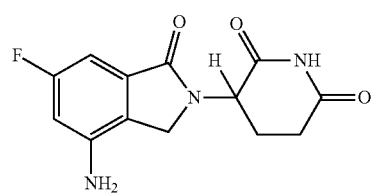
B102
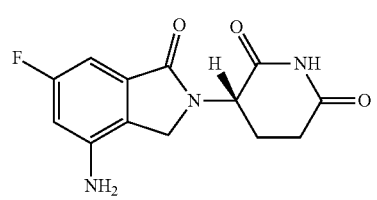
B103
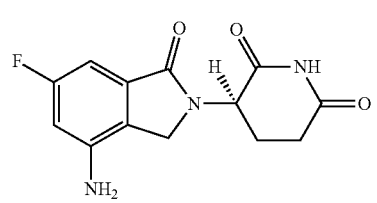
B104
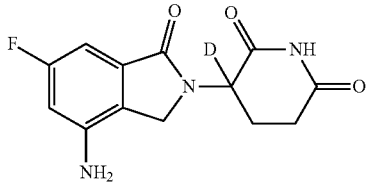
B105
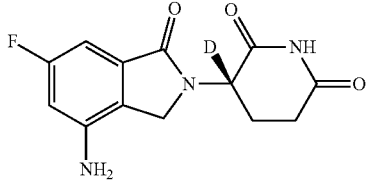
B106
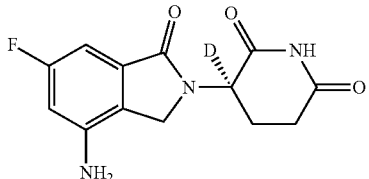
B107
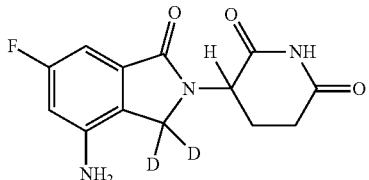
B108
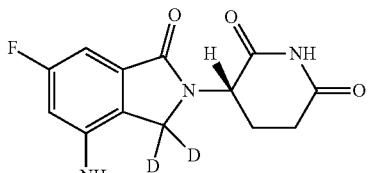
B109
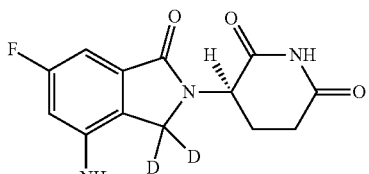
B110
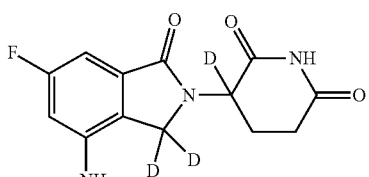
B111
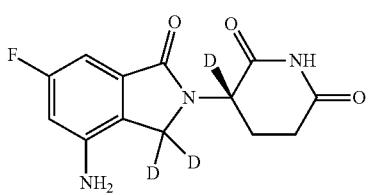

-continued
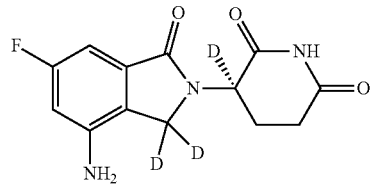 B112
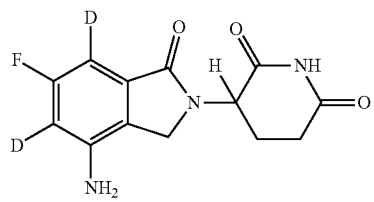 B113
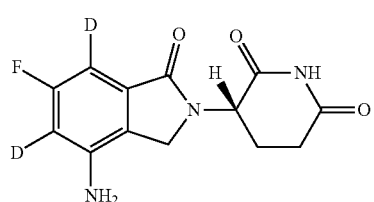 B114
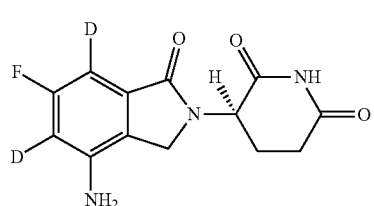 B115
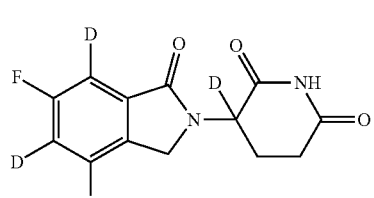 B116
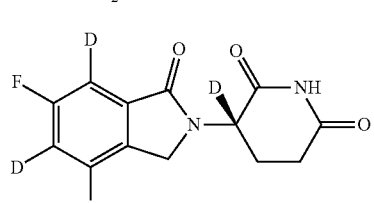 B117
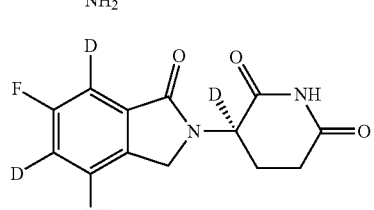 B118
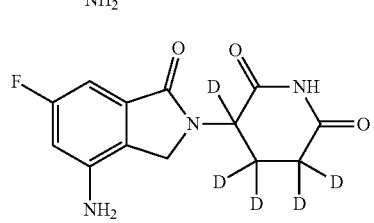 B119
-continued
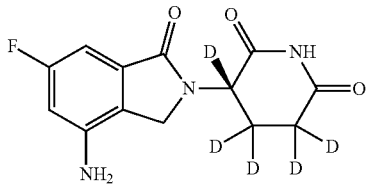 B120
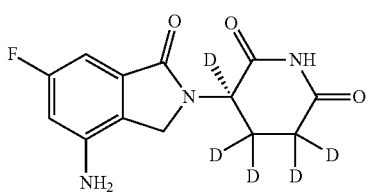 B121
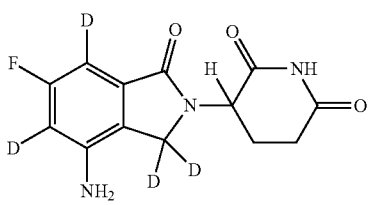 B122
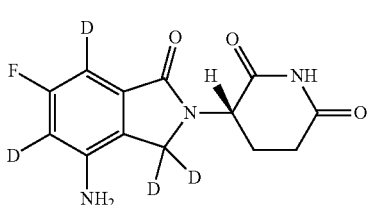 B123
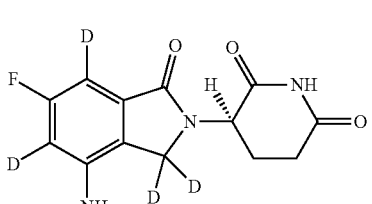 B124
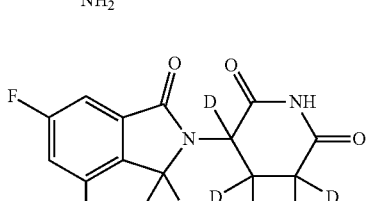 B125
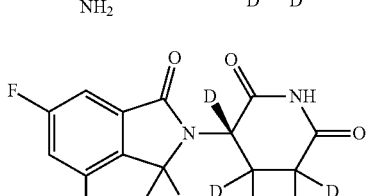 B126
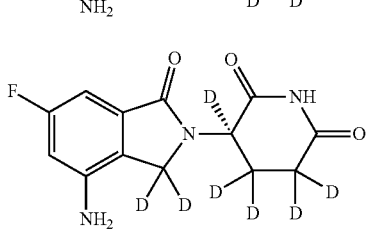 B127

B128
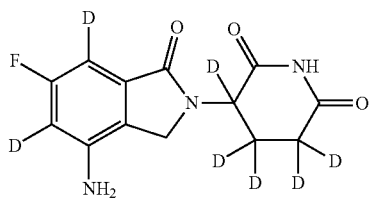
B129
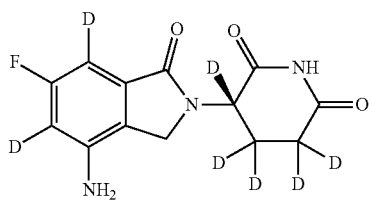
B130
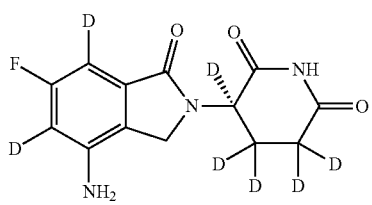
B131
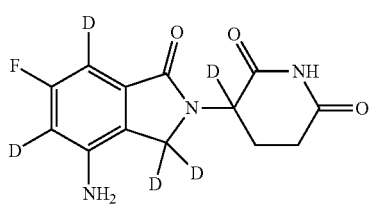
B132
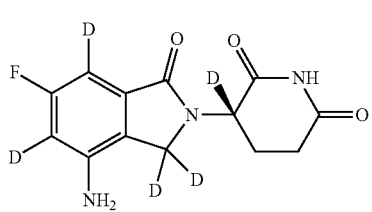
B133
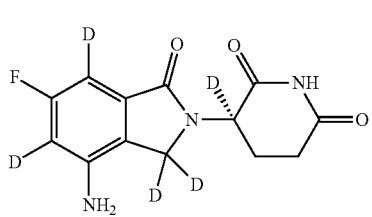
B134
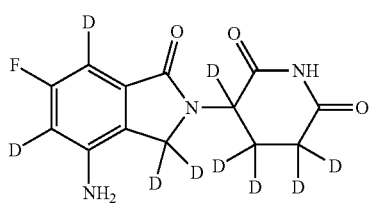
B135
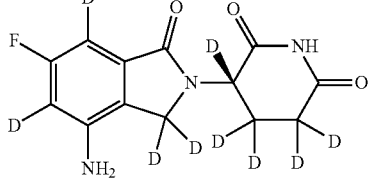
B136
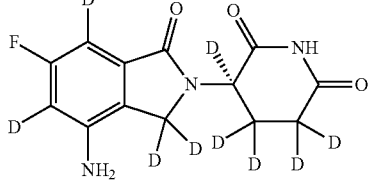
B137
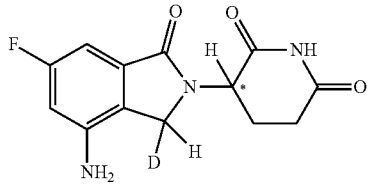
B138
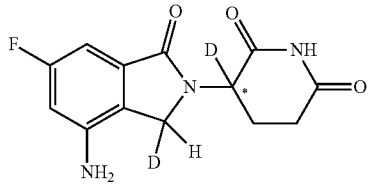
B139
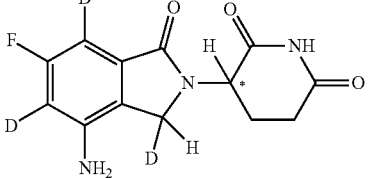
B140
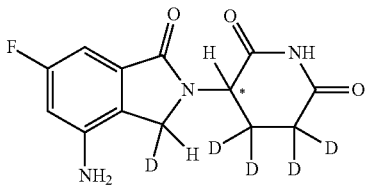
B141
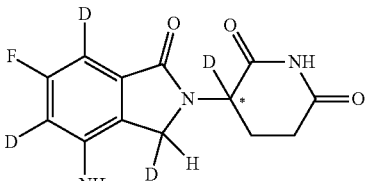
B142
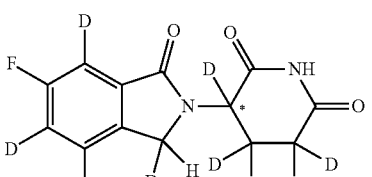

C101
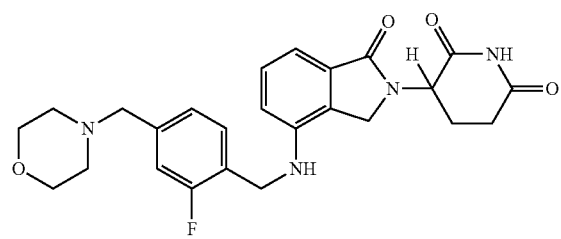
C102
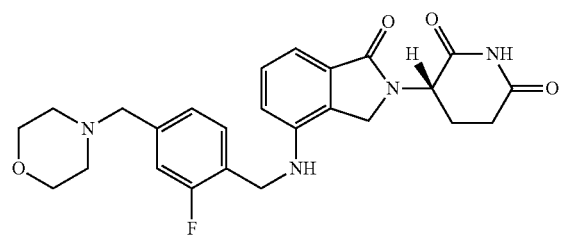
C103
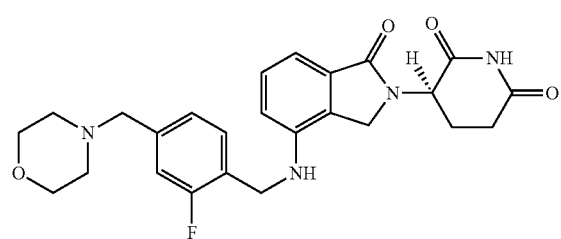
C104
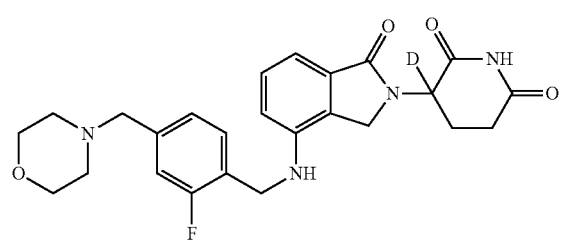
C105
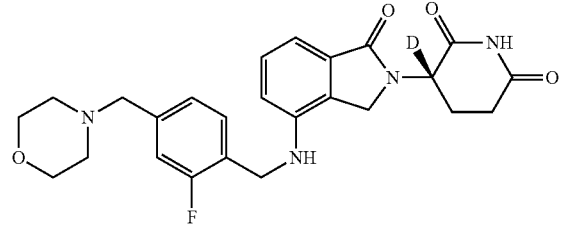
C106
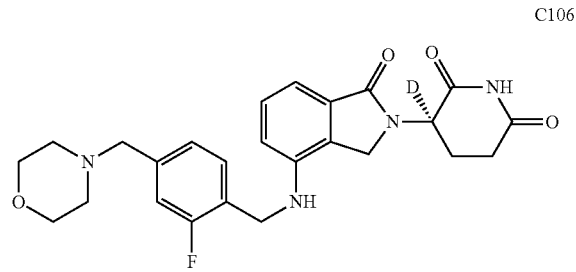
C107
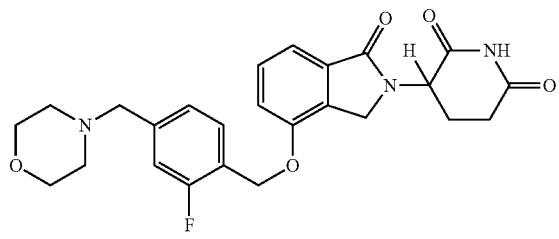
C108
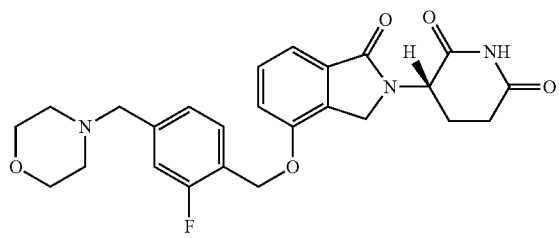
C109
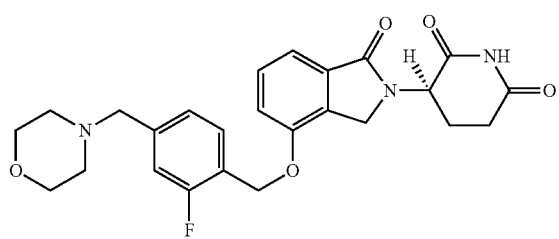
C110
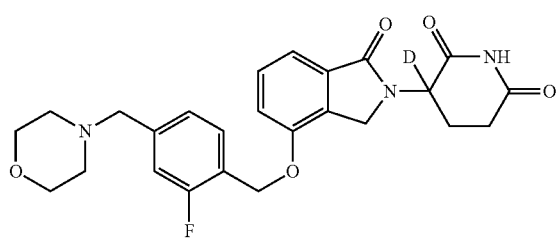
C111
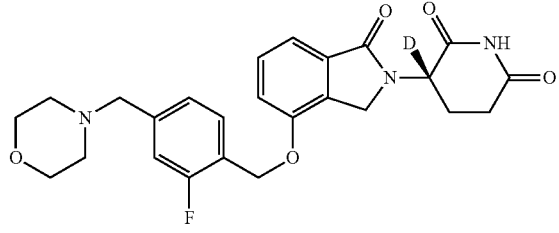
C112
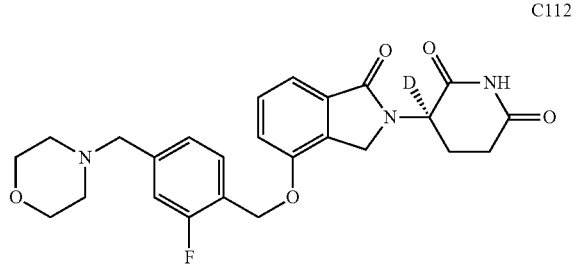

C113
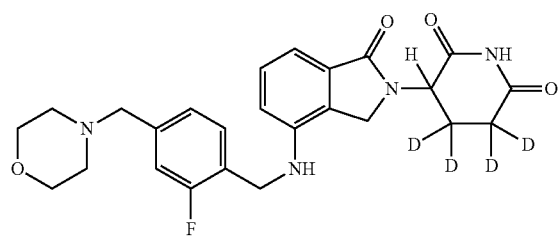
C119
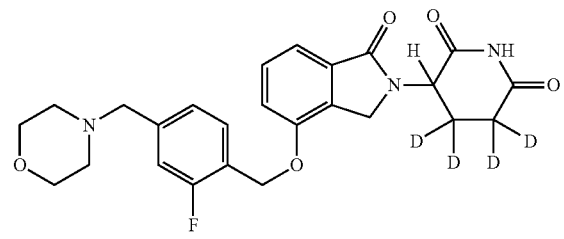
C114
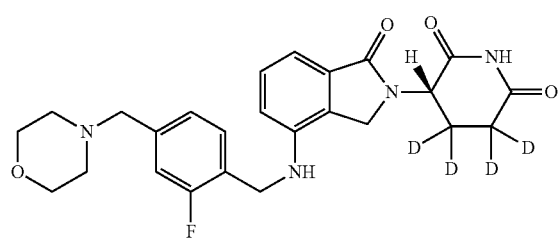
C120
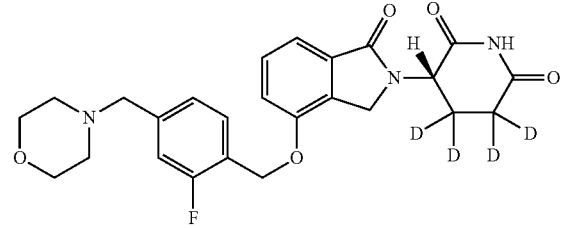
C115
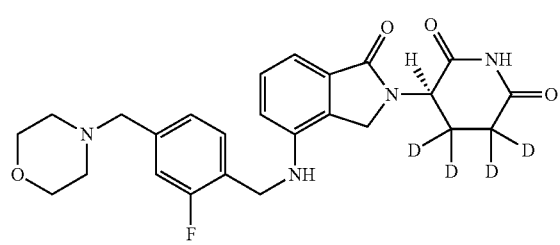
C121
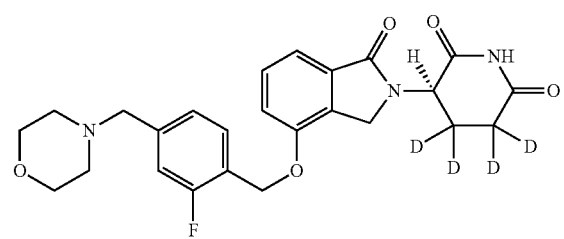
C116
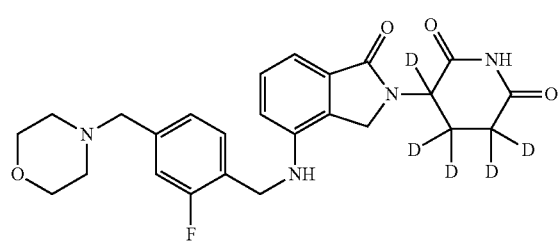
C122
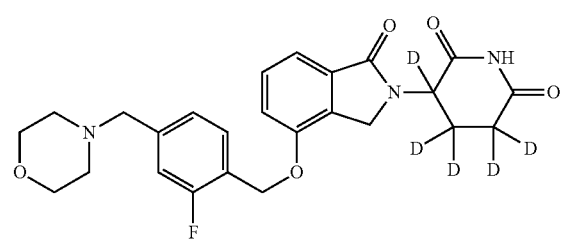
C117
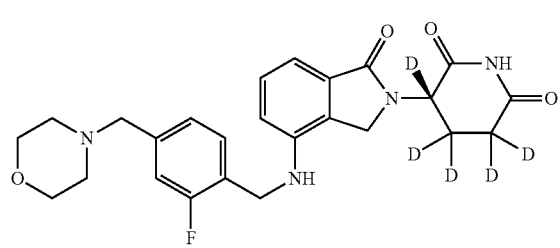
C123
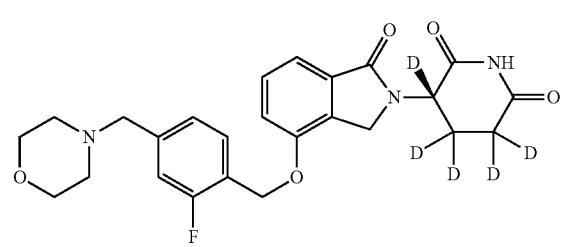
C118
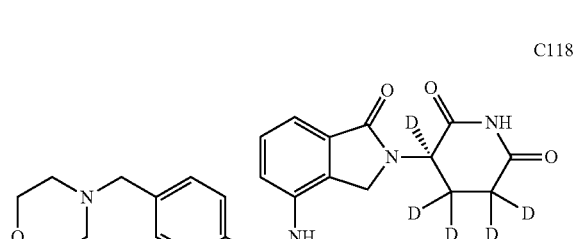
C124
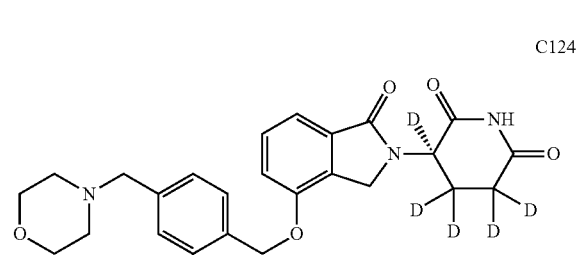

-continued

C125

C126

C127

C128

C129

C130

C131

C132

C133

C134

C135

C136

-continued
C137
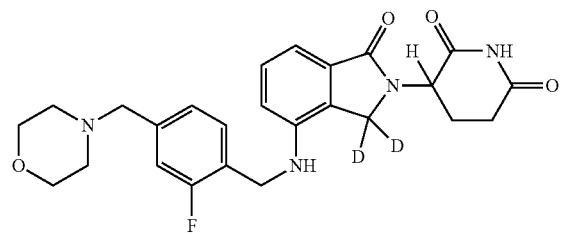
C138
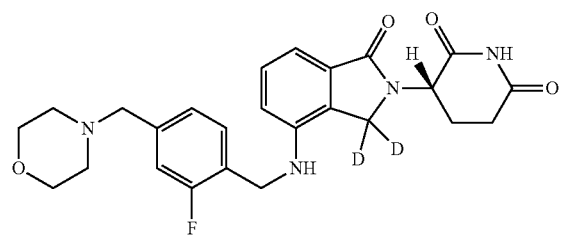
C139
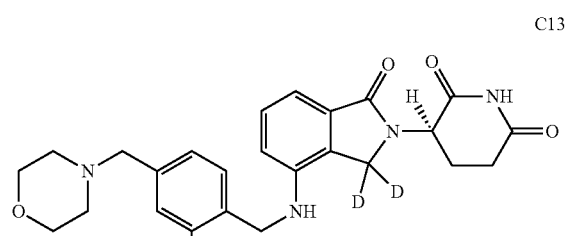
C140
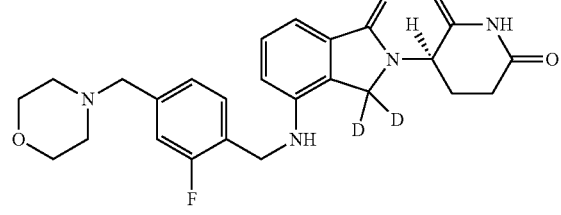
C141
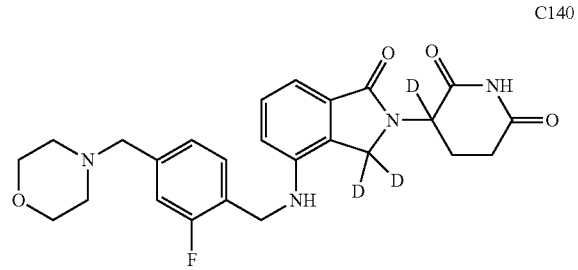
C142
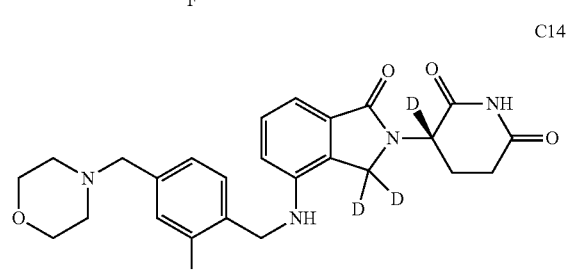
-continued
C143
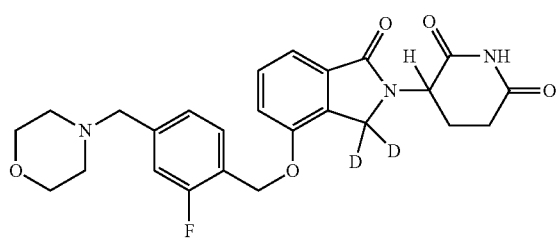
C144
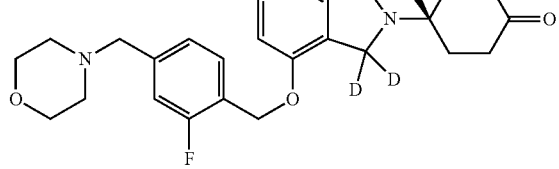
C145
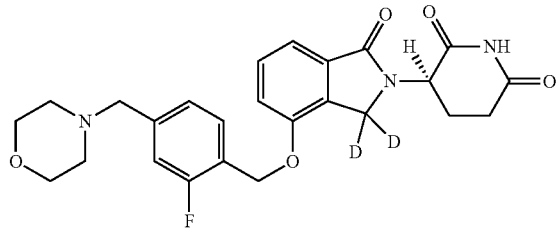
C146
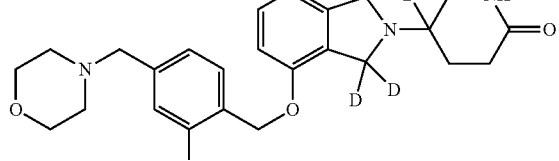
C147
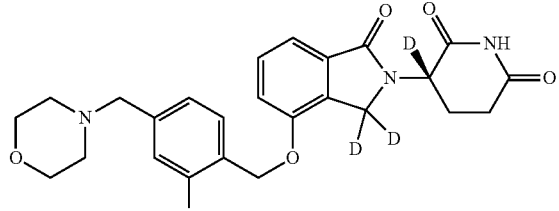
C148
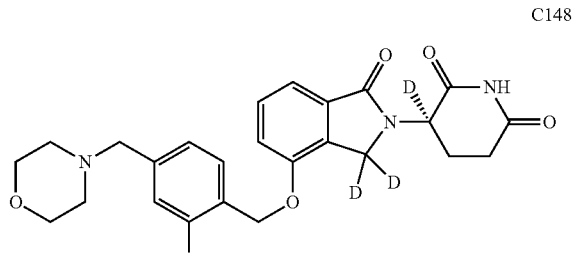

C149
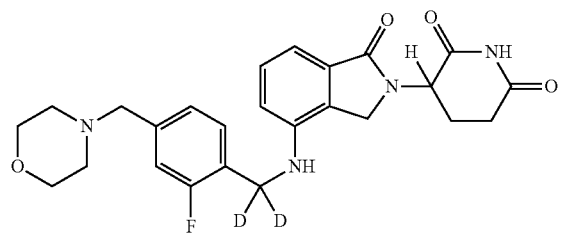
C150
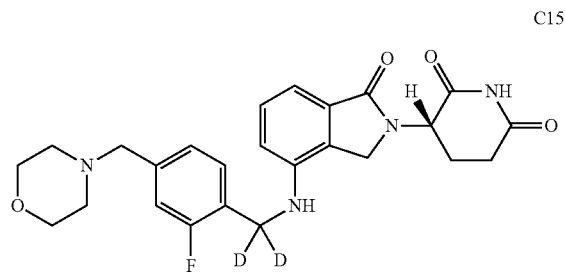
C151
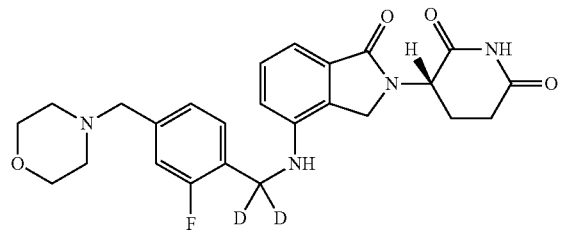
C152
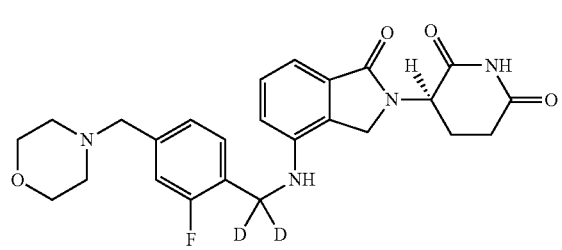
C153
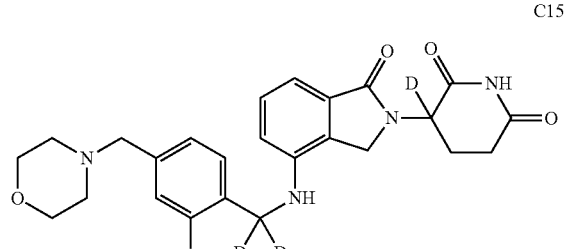
C154
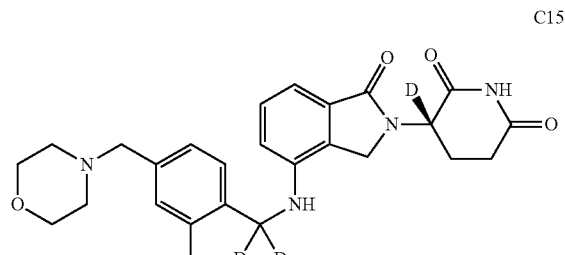
C155
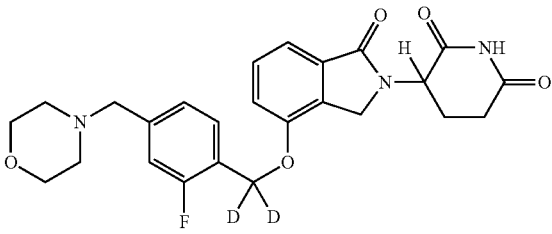
C156
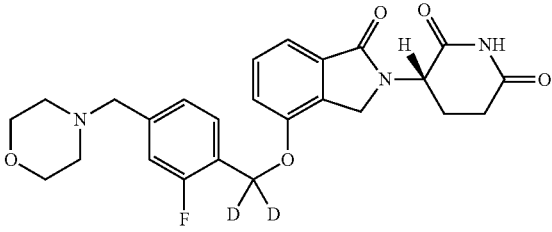
C157
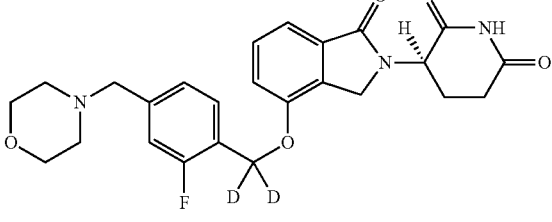
C158
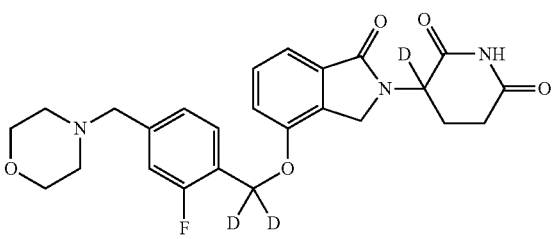
C159
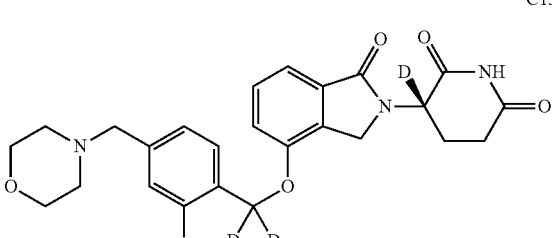
C160
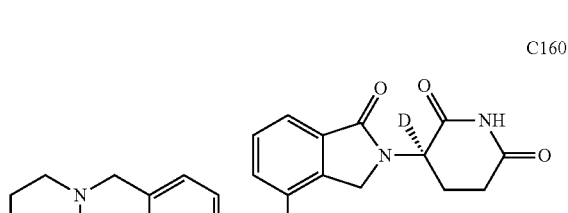

27
-continued
C161
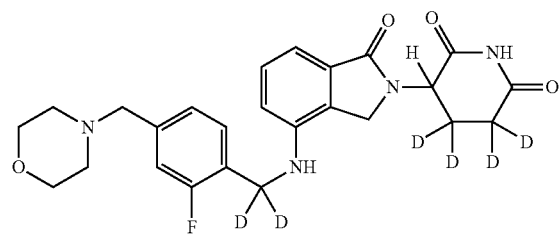
C162
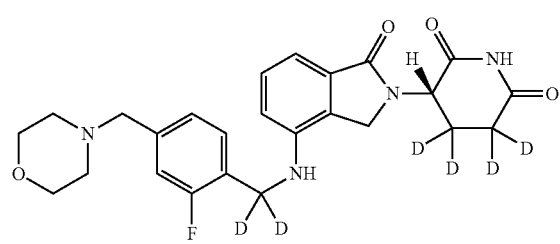
C163
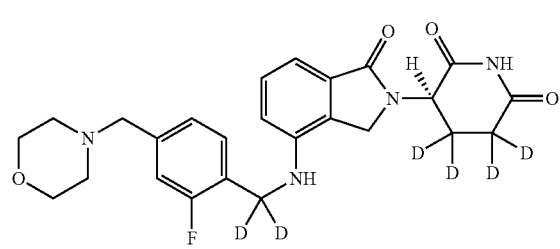
C164
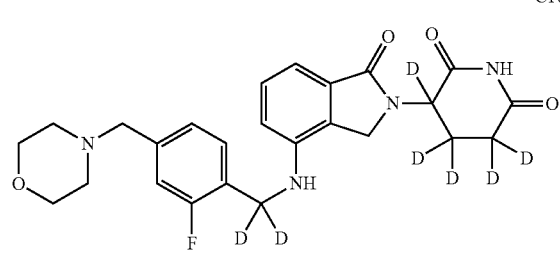
C165
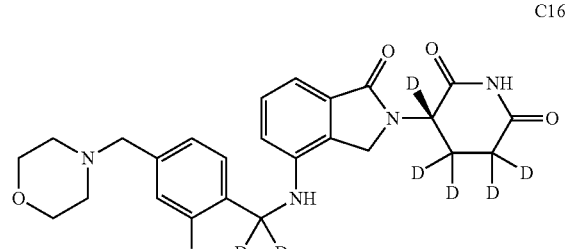
C166
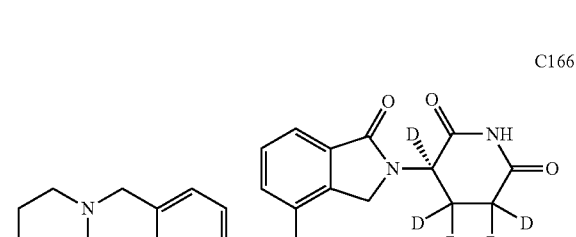
28
-continued
C167
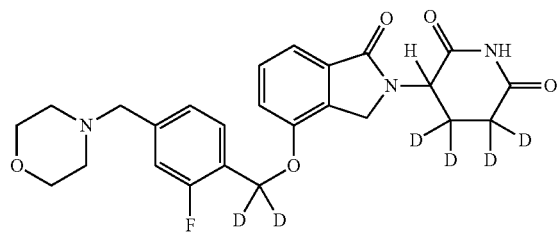
C168
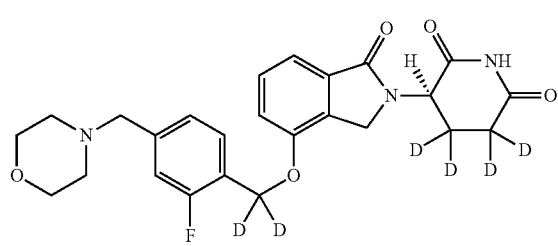
C169
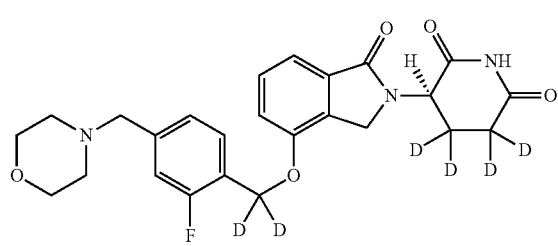
C170
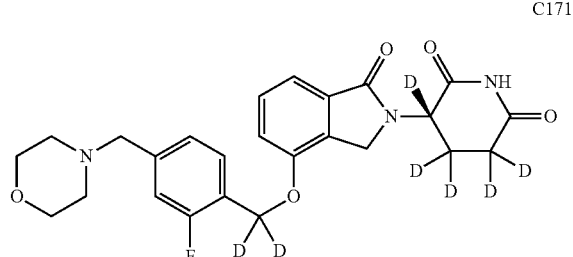
C171
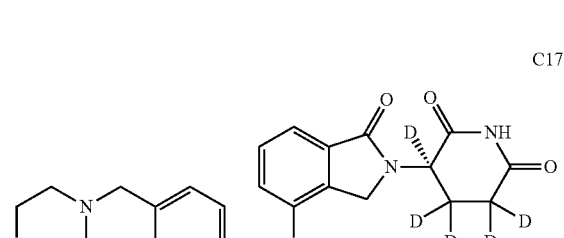
C172
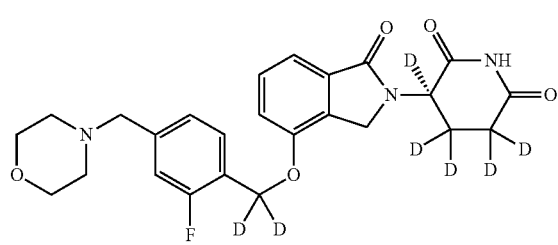

C173

C174

C175

C176

C177

C178

C179

C180

C181

C182

C183

C184

C185
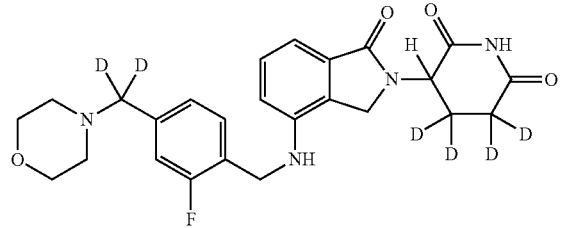
C186
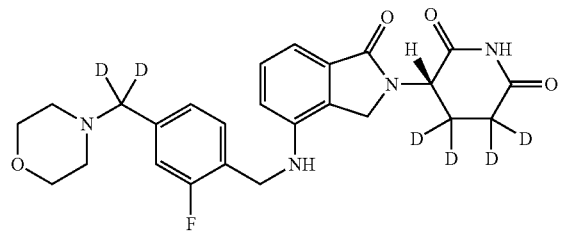
C187
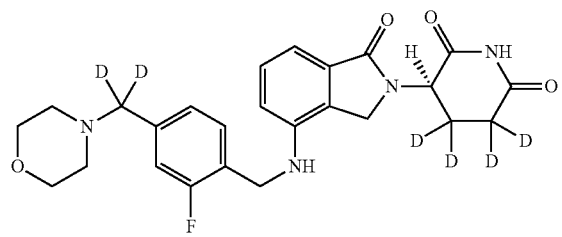
C188
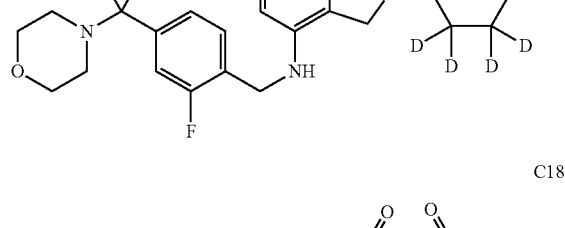
C189
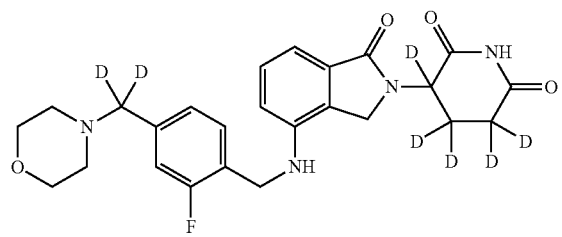
C190
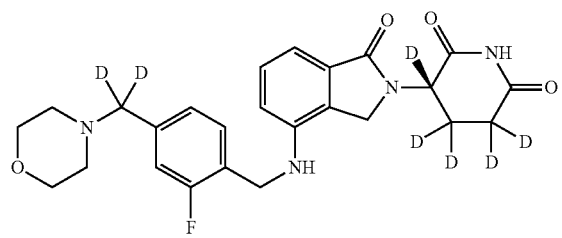
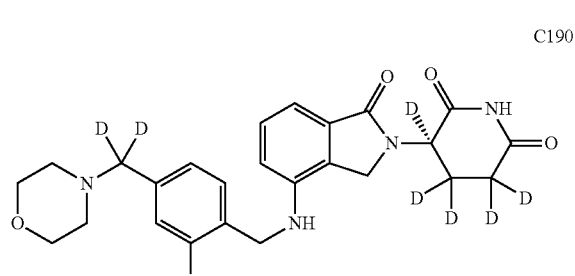
C191
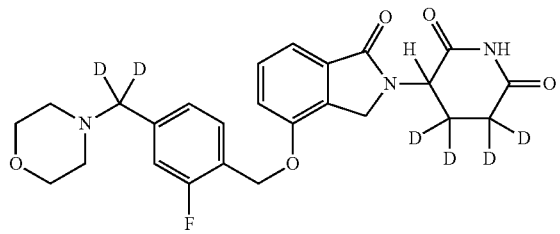
C192
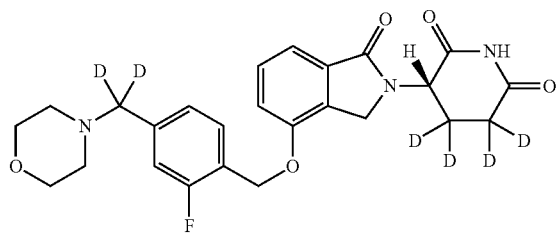
C193
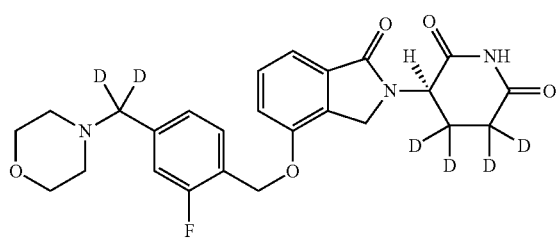
C194
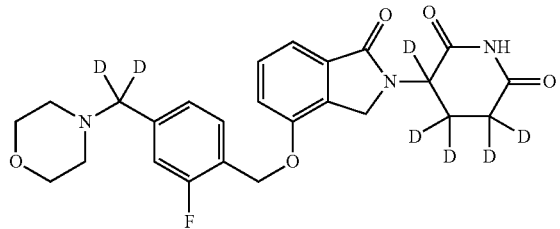
C195
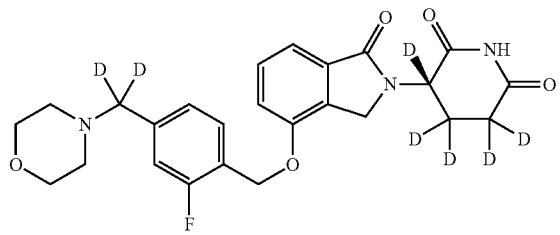
C196
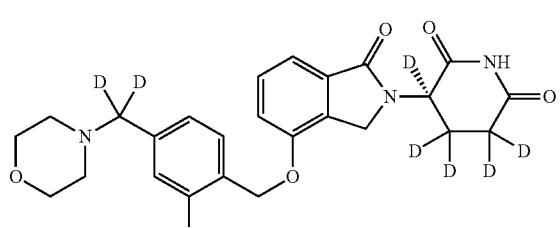

-continued
C197
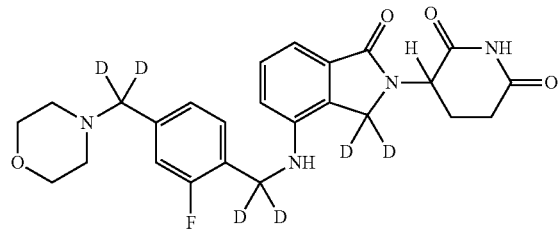
C198
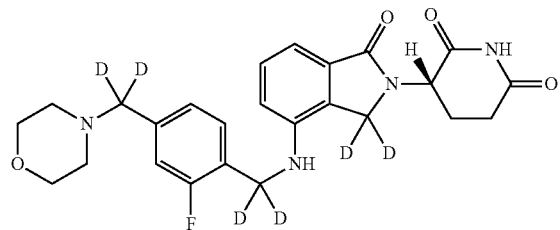
C199
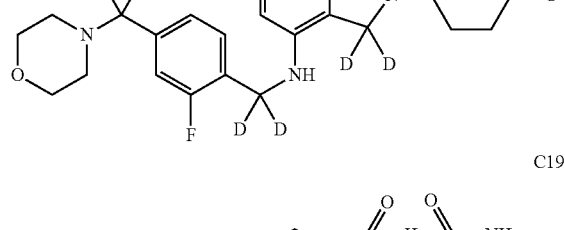
C200
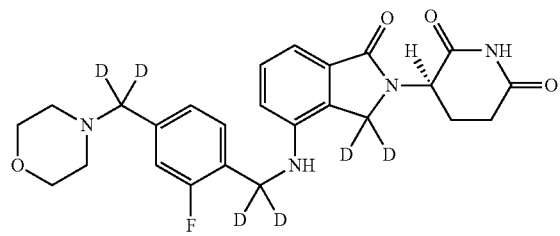
C201
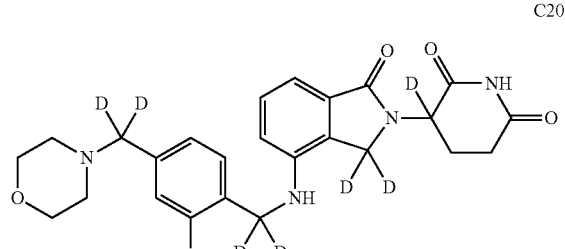
C202
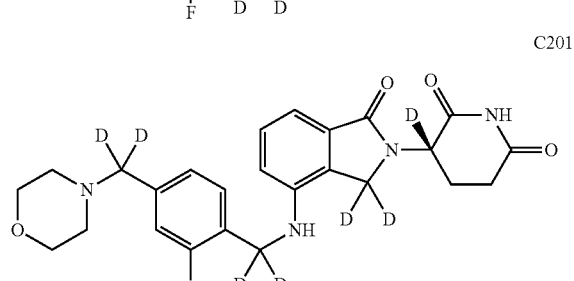
C203
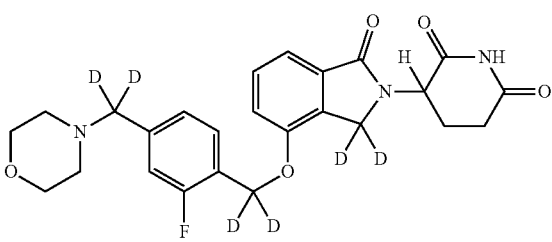
C204
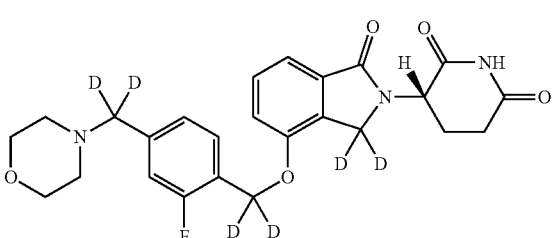
C205
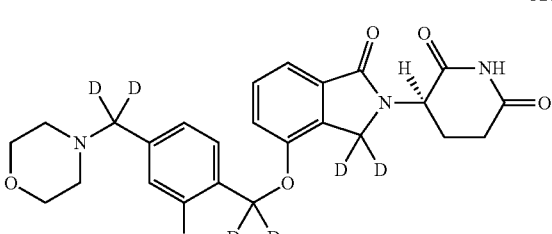
C206
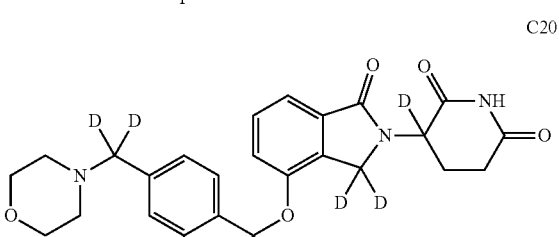
C207
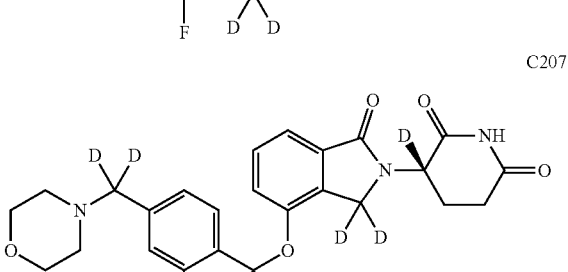
C208
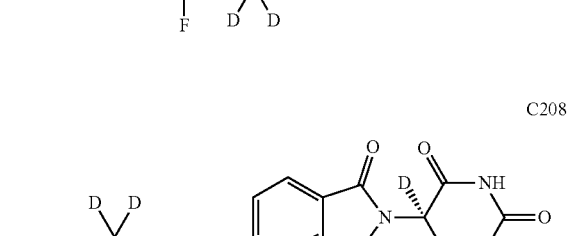

C209
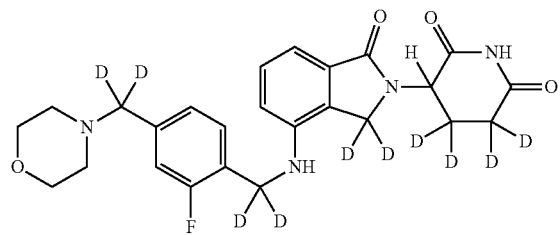
C210
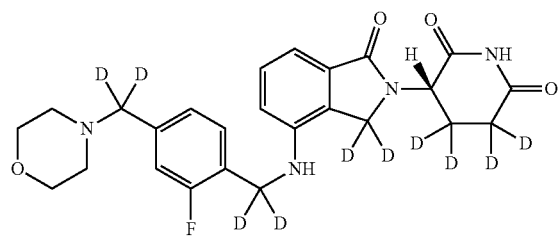
C211
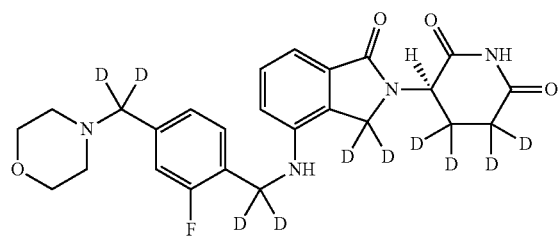
C212
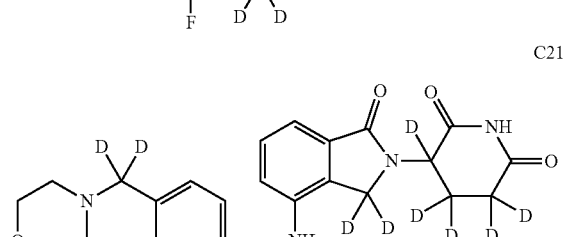
C213
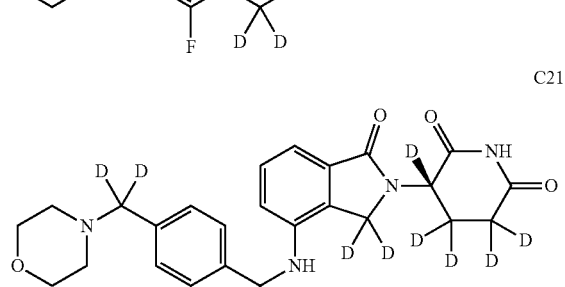
C214
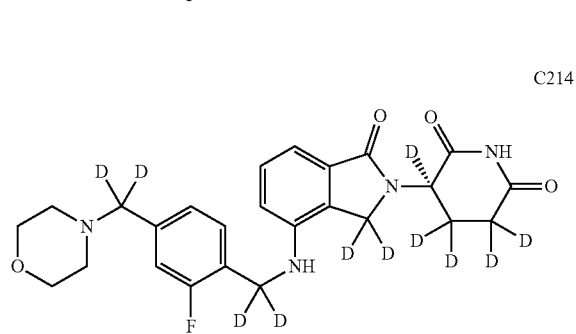
C215
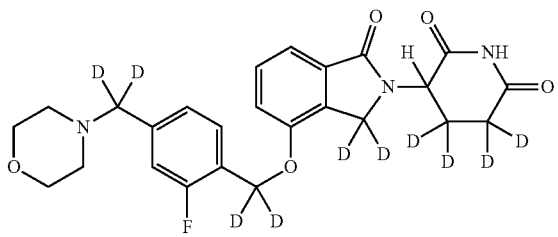
C216
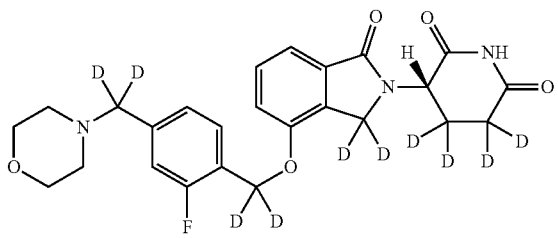
C217
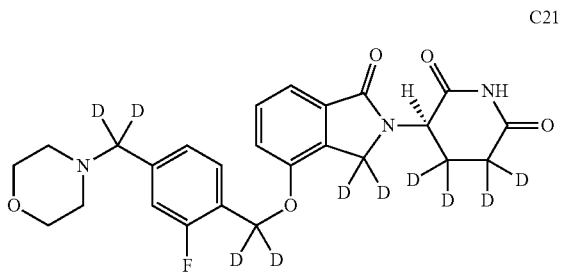
C218
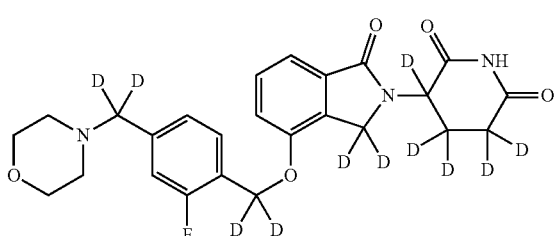
C219
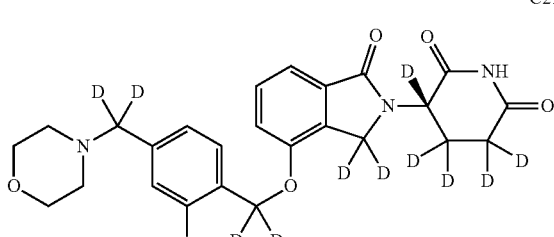
C220
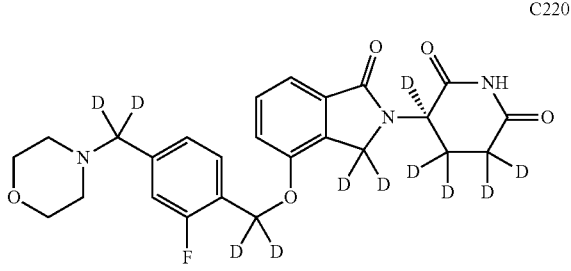

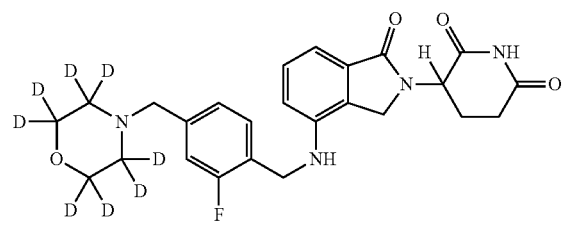
C221
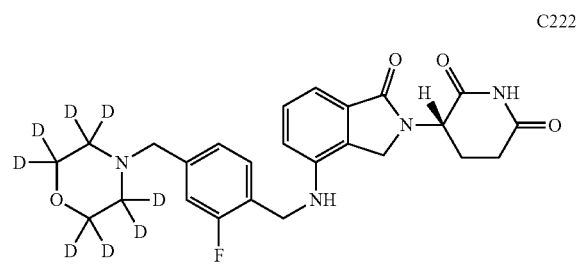
C222
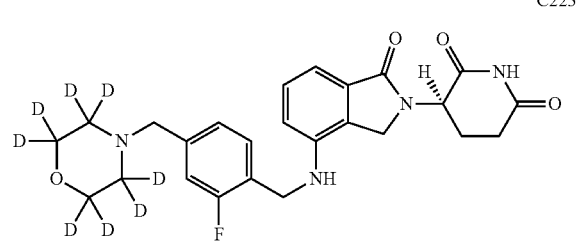
C223
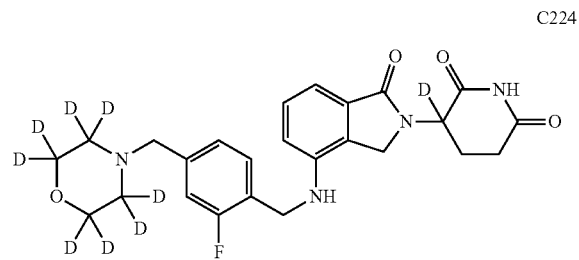
C224
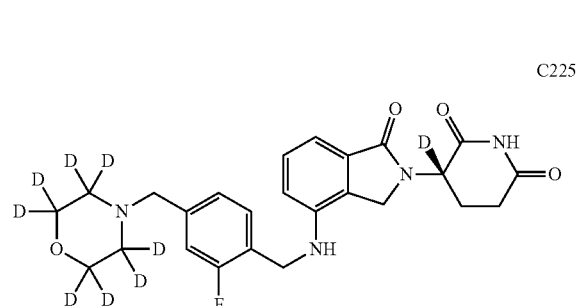
C225
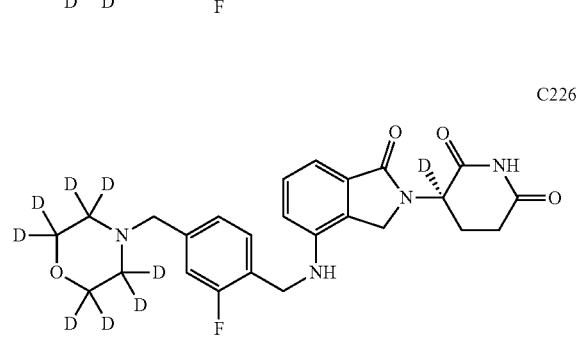
C226
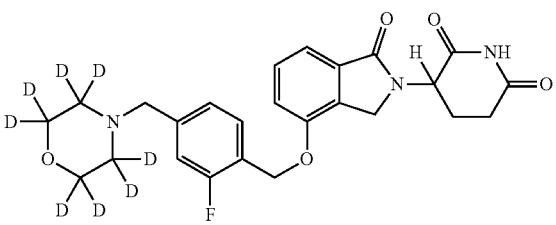
C227
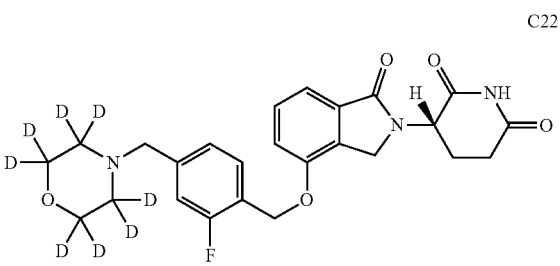
C228
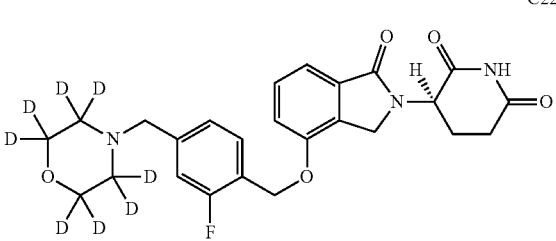
C229
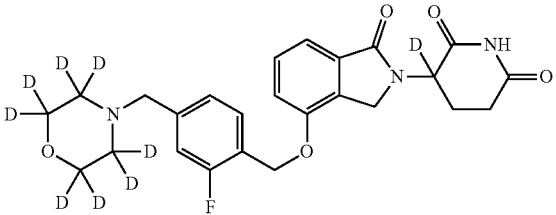
C230
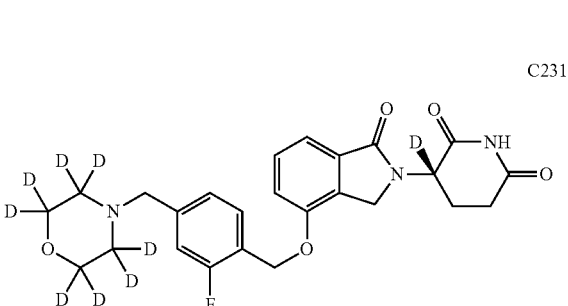
C231
C232

-continued
C233
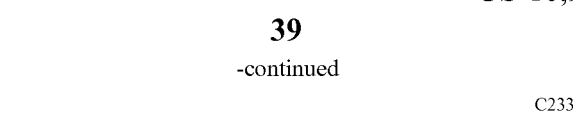
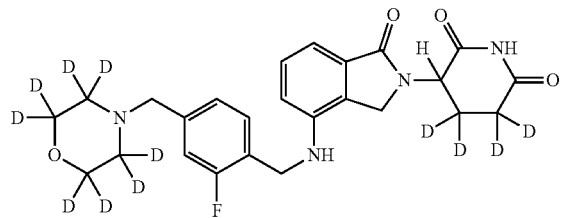
C234
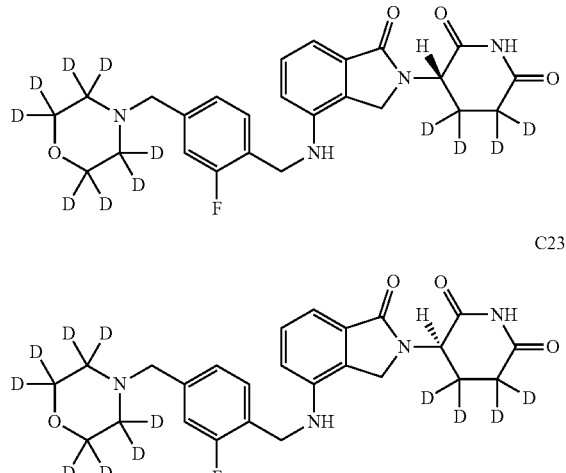
C235
C236
C237
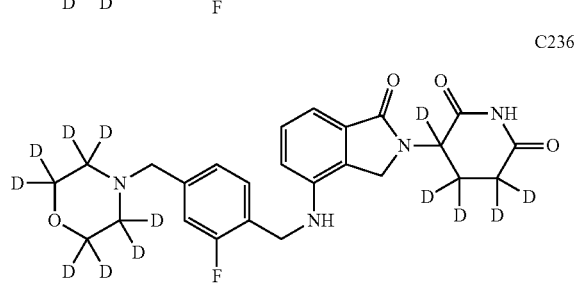
C238
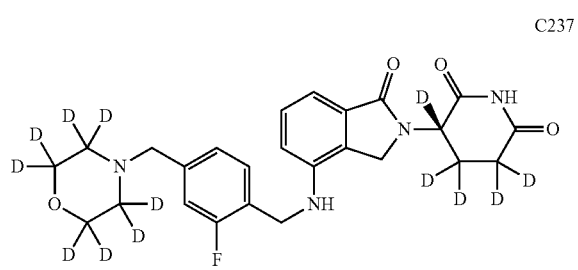
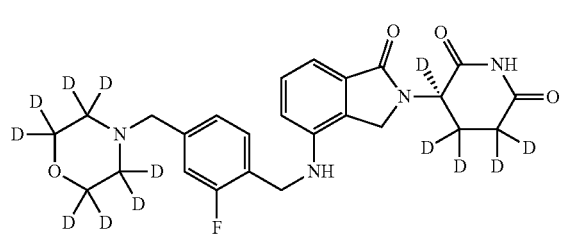
-continued
C239
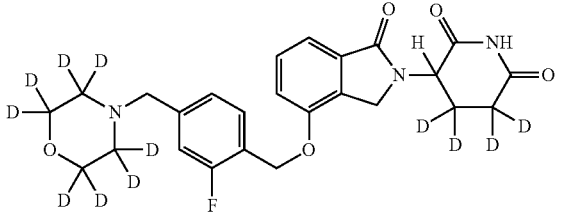
C240
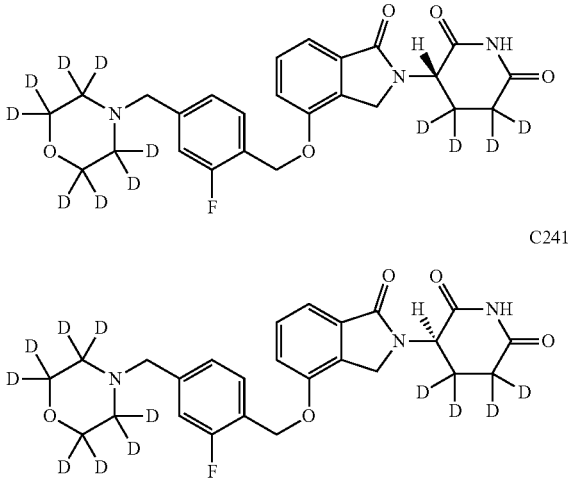
C241
C242
C243
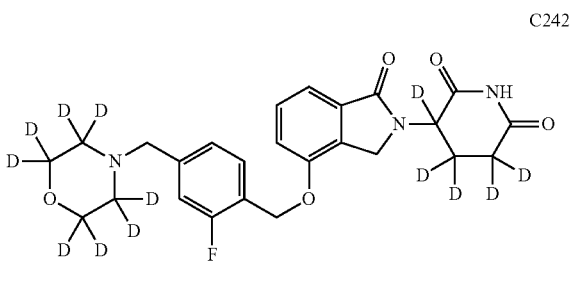
C244
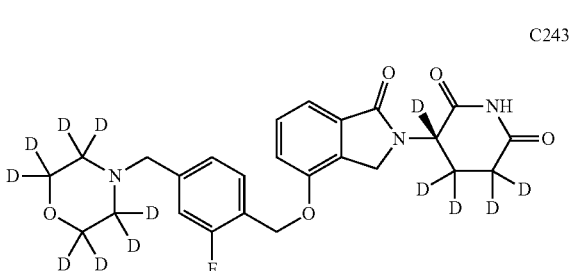
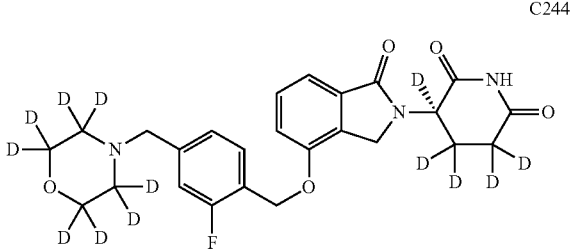

C245

C246

C247

C248

C249

C250

C251

C252

C253

C254

C255

C256

C257
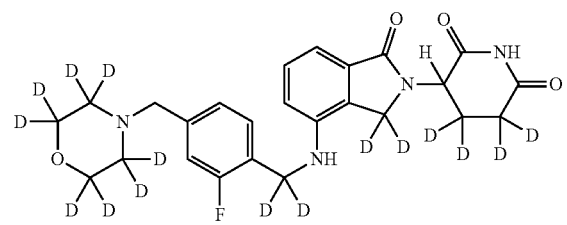
C258
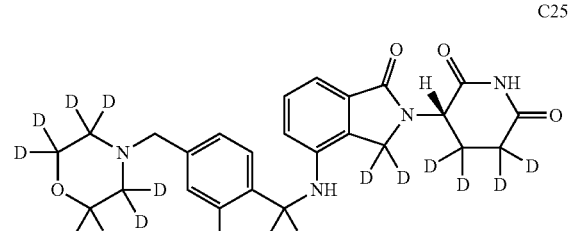
C259
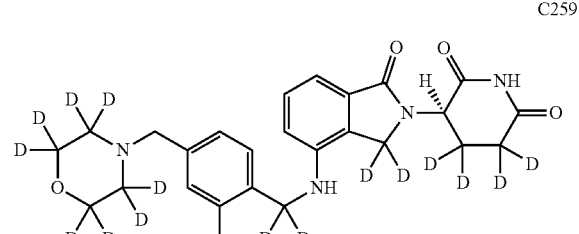
C260
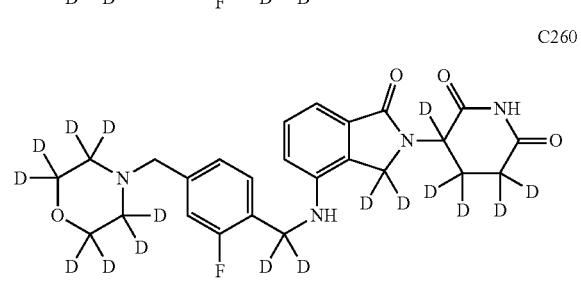
C261
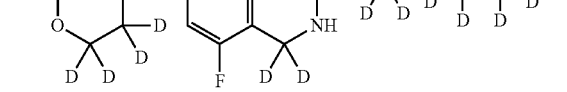
C262
C263
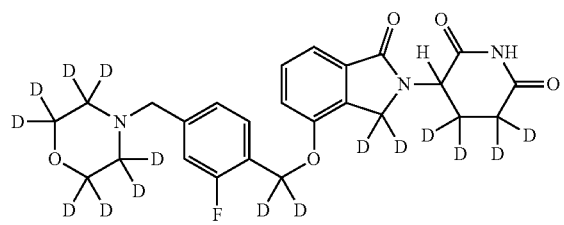
C264
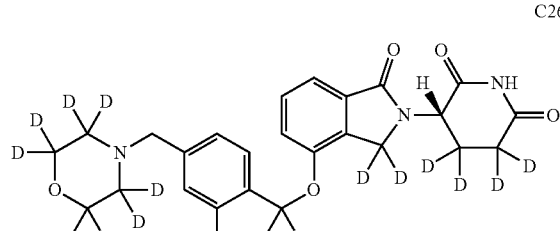
C265
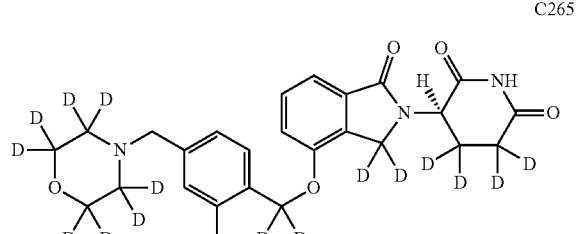
C266
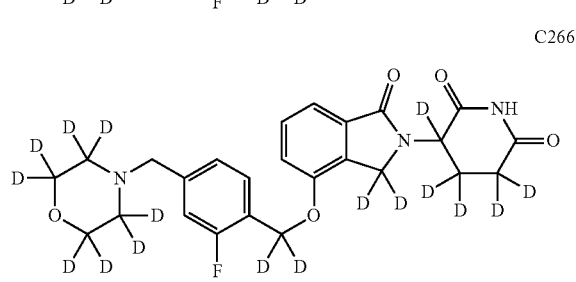
C267
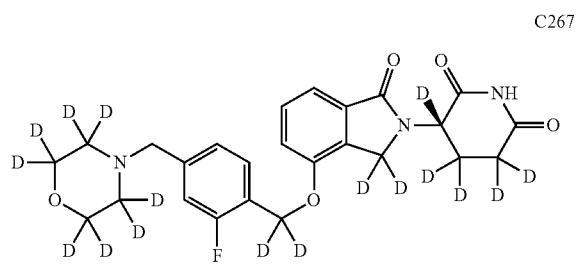
C268
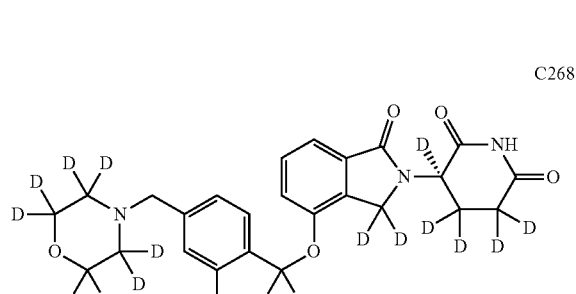

C269
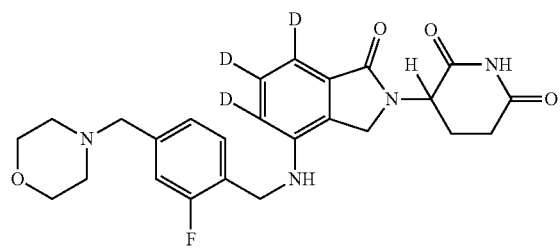
C275
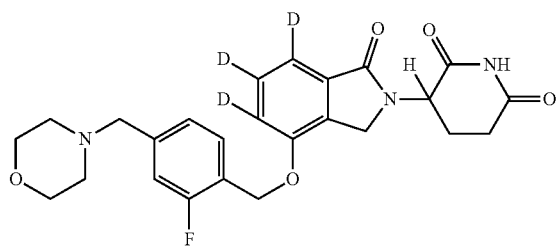
C270
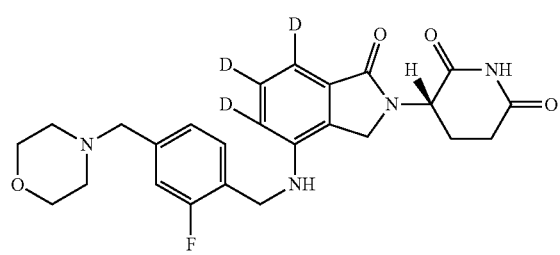
C276
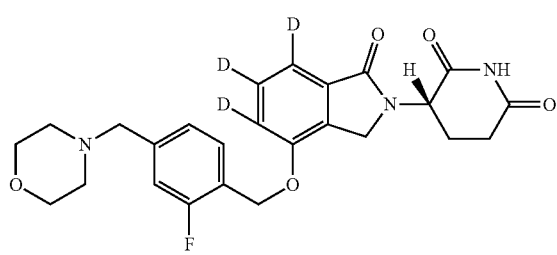
C271
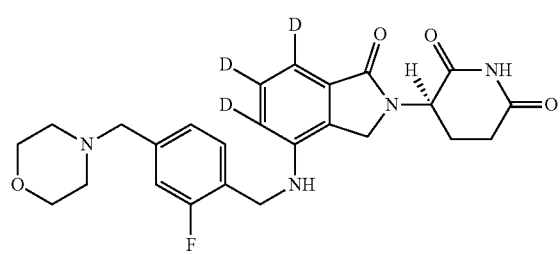
C277
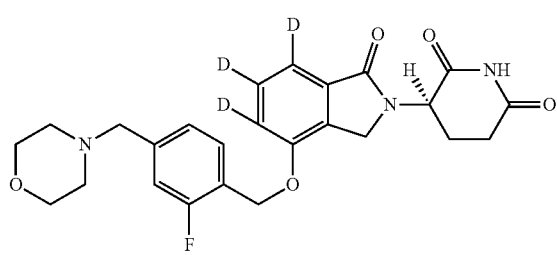
C272
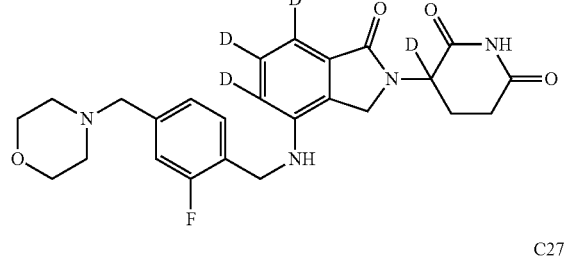
C278
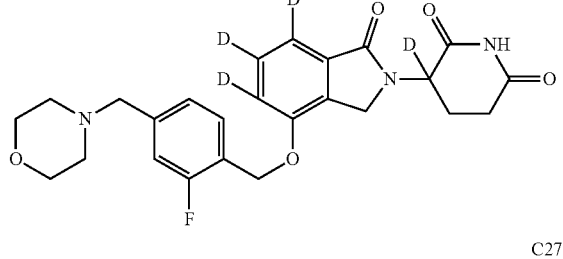
C273
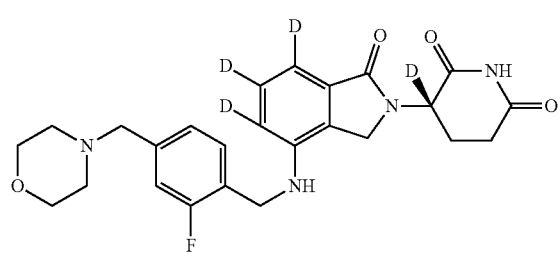
C279
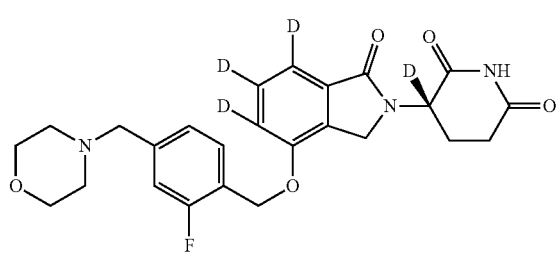
C274
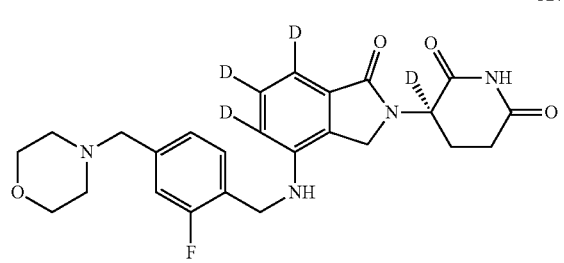
C280
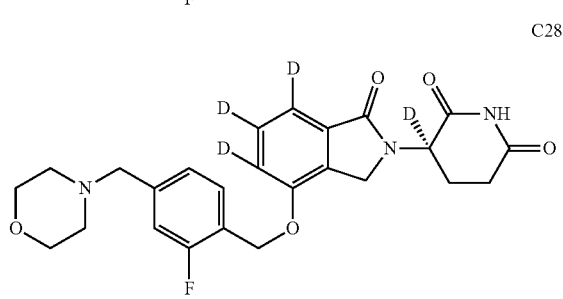

-continued

C281

C282

C283

C284

C285

C286

-continued

C287

C288

C289

C290

C291

C292

49

-continued

C293

C294

C295

C296

C297

C298

50

-continued

C299

C300

C301

C302

C303

C304

C305
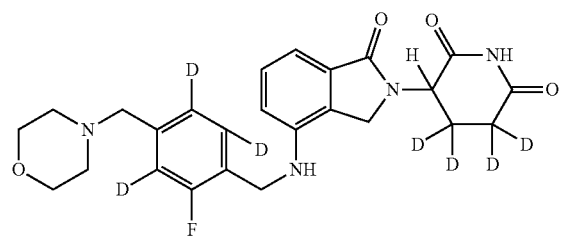
C306
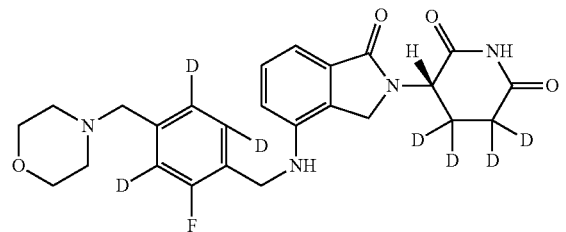
C307
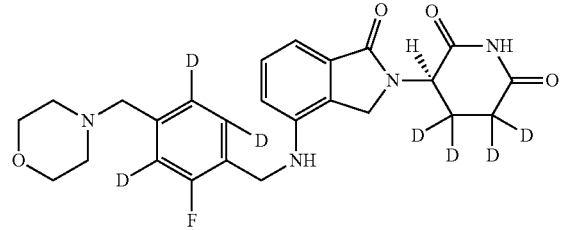
C308
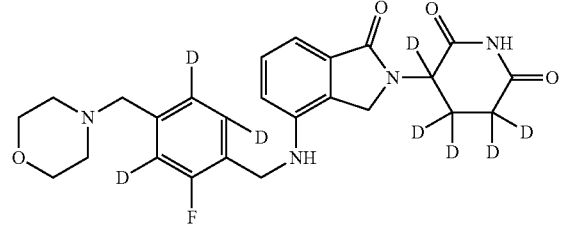
C309
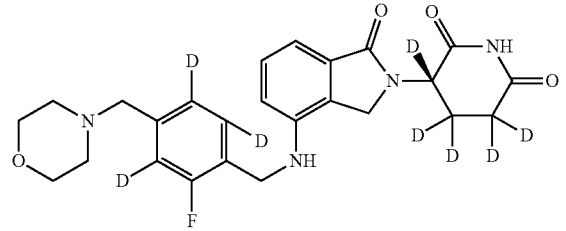
C310
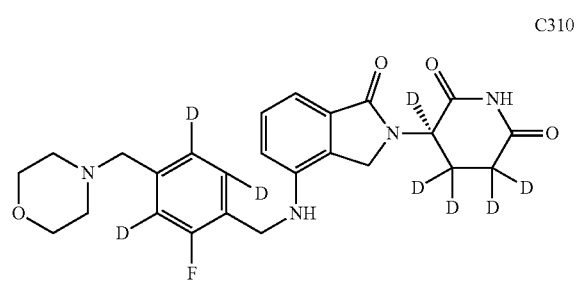
C311
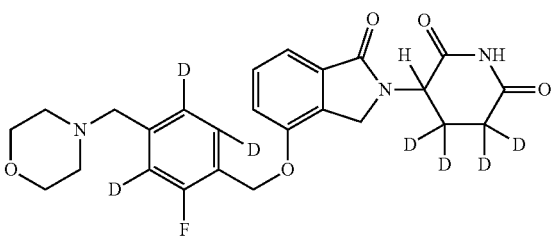
C312
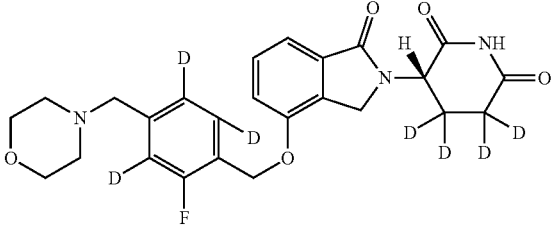
C313
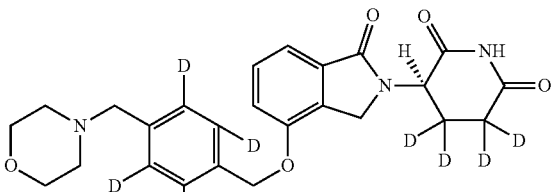
C314
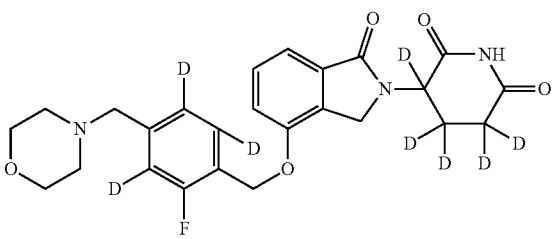
C315
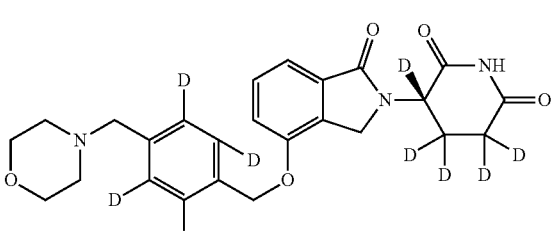
C316
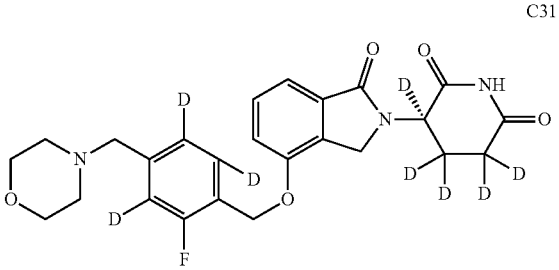

C317
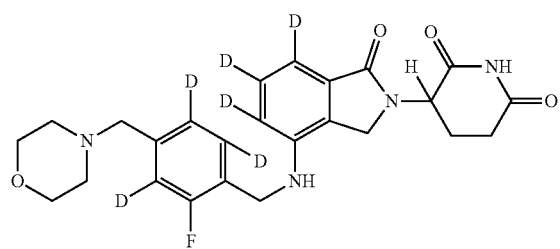
C318
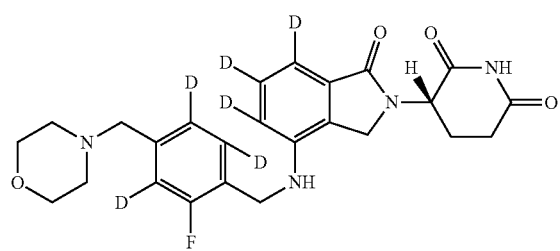
C319
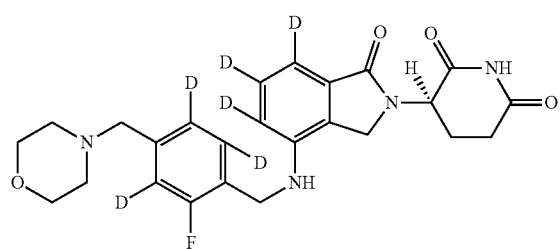
C320
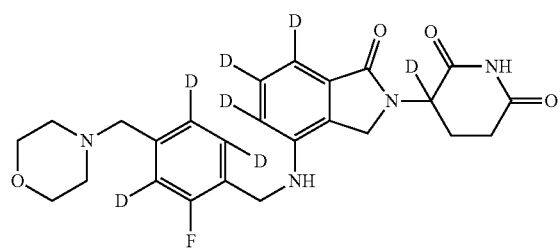
C321
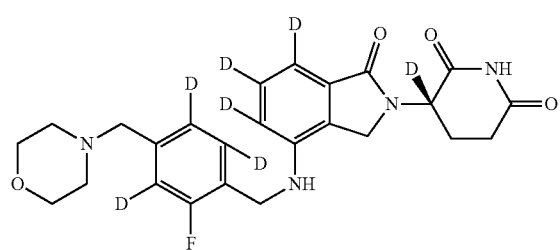
C322
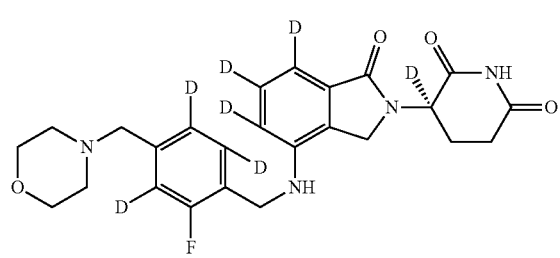
C323
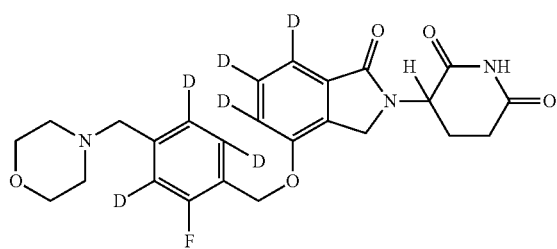
C324
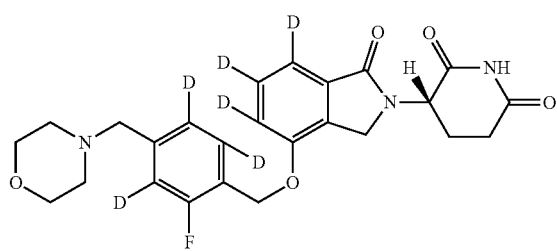
C325
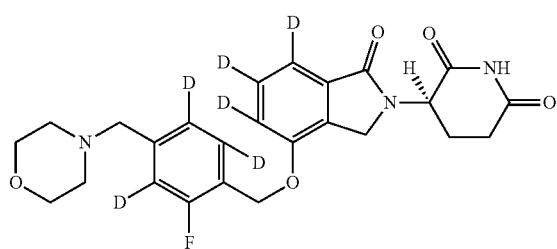
C326
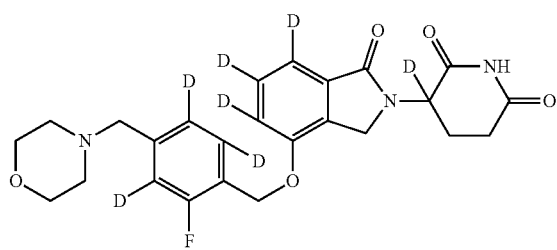
C327
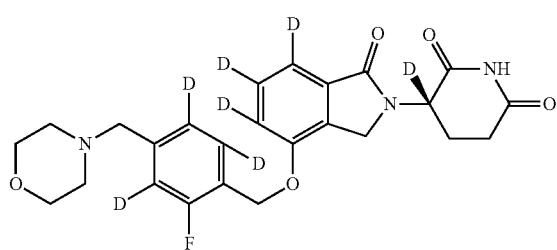
C328
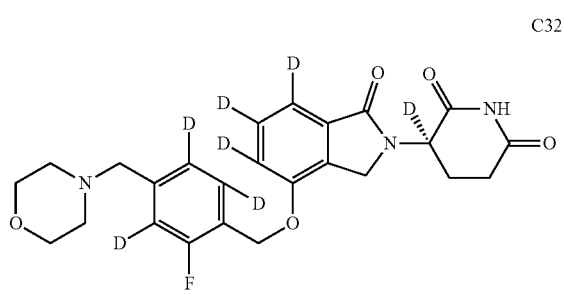

C329
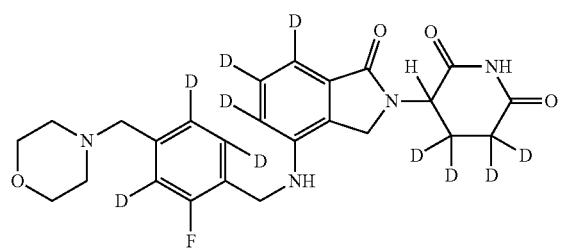
C330
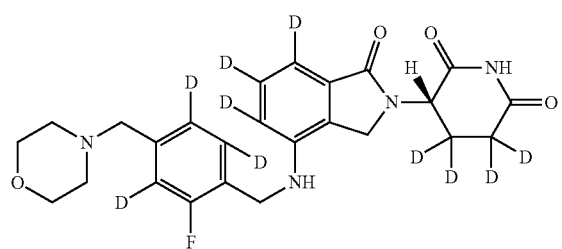
C331
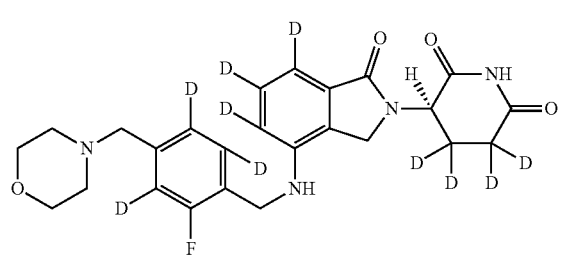
C332
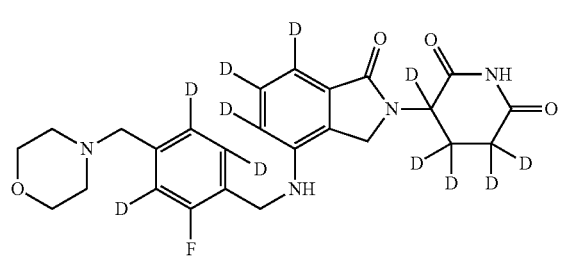
C333
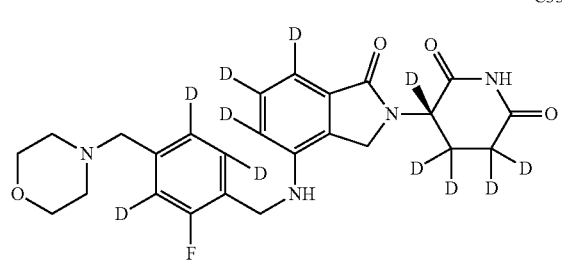
C334
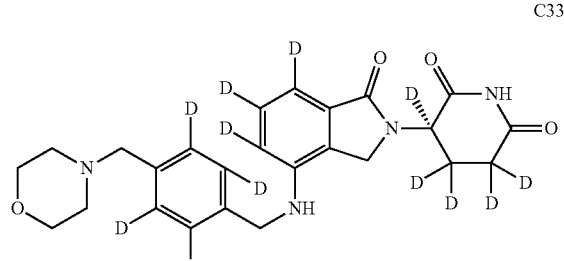
C335
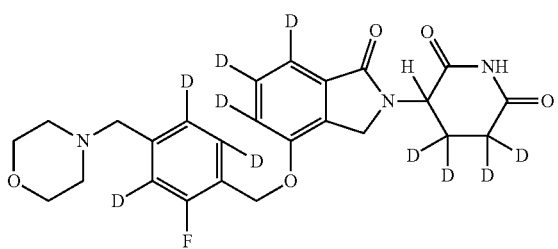
C336
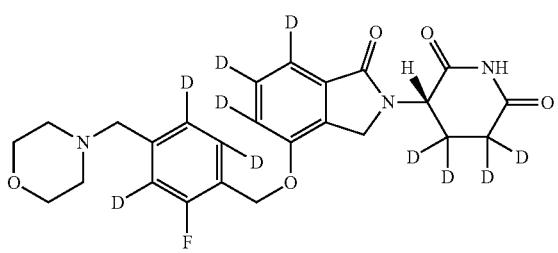
C337
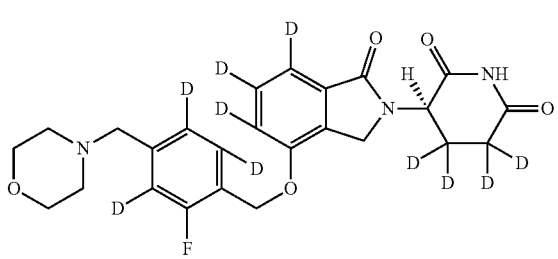
C338
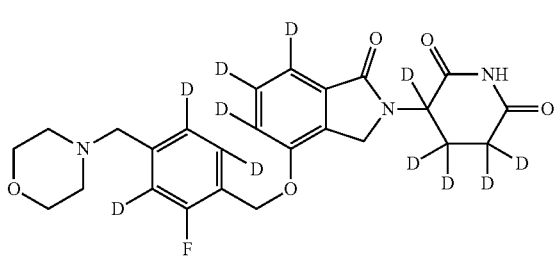
C339
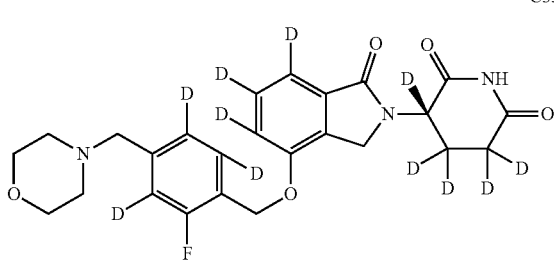
C340
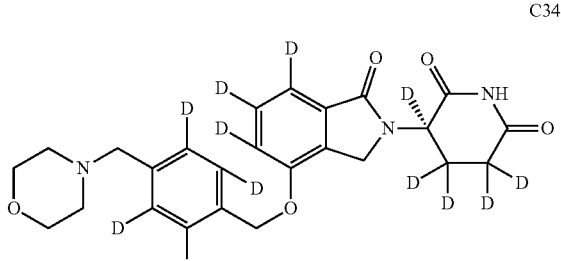

-continued
C341
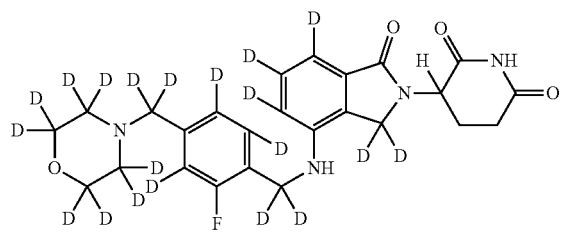
C342
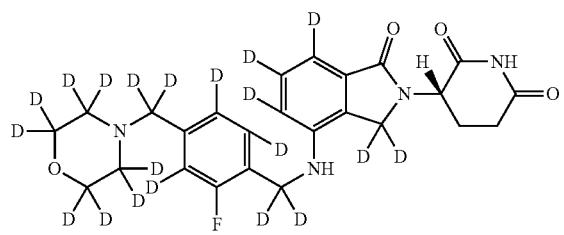
C343
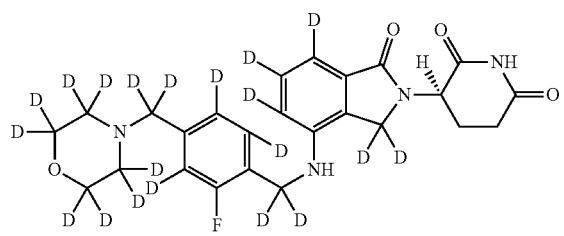
C344
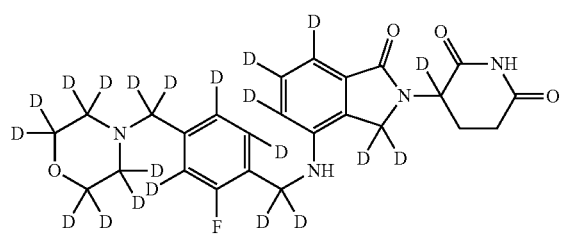
C345
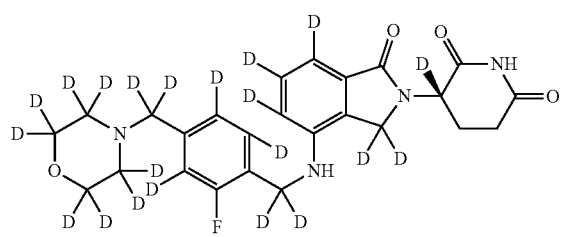
C346
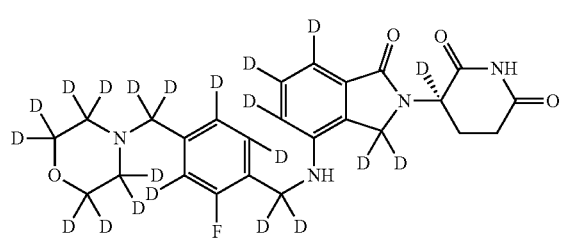
-continued
C347
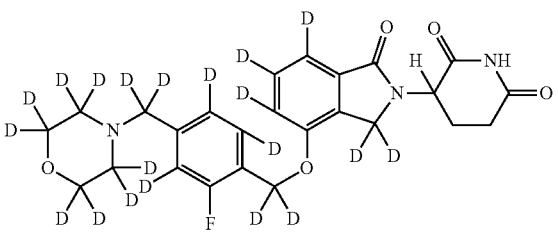
C348
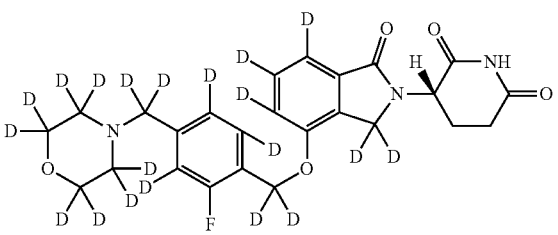
C349
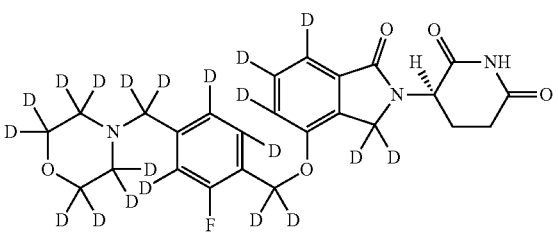
C350
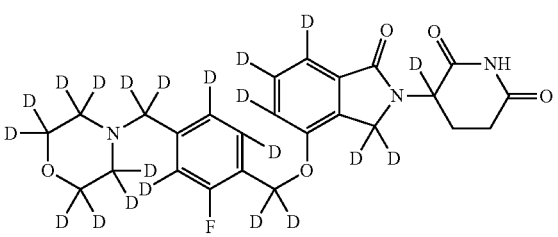
C351
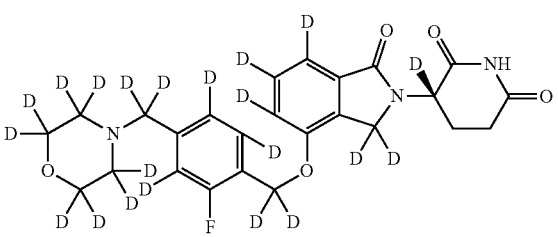
C352
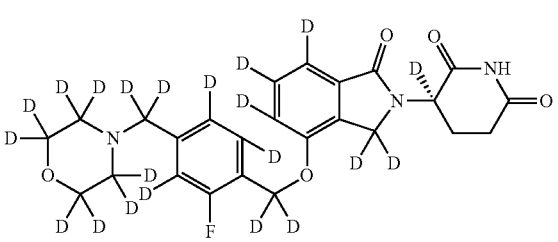

C353
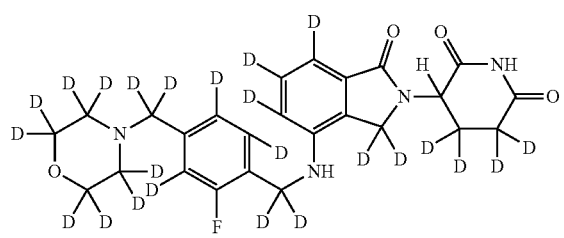
C359
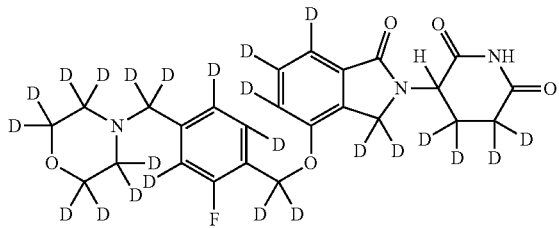
C354
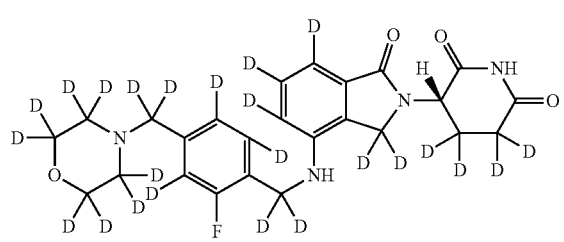
C360
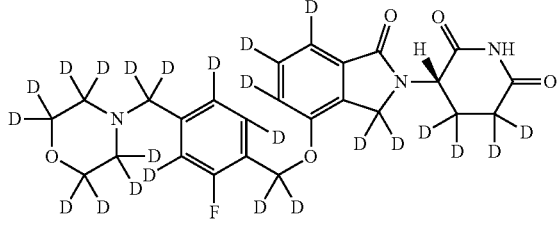
C355
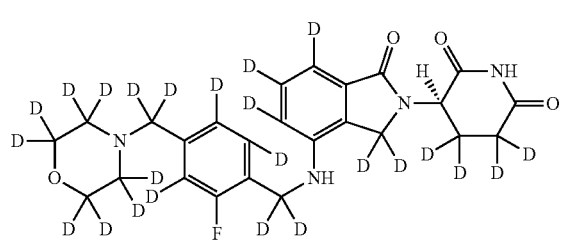
C361
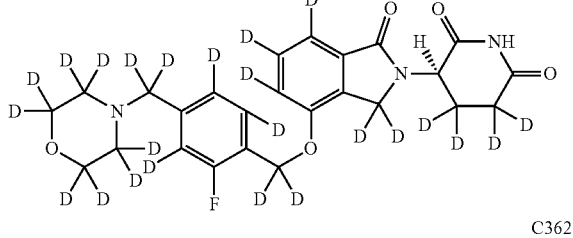
C356
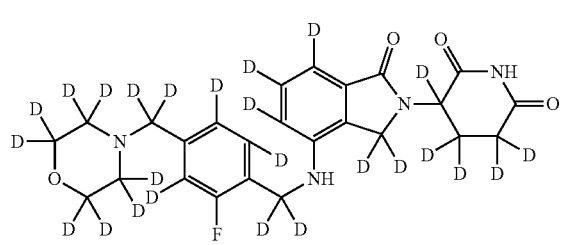
C362
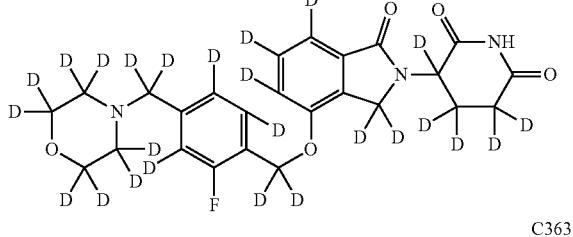
C357
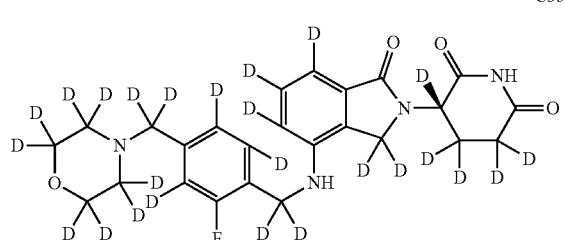
C363
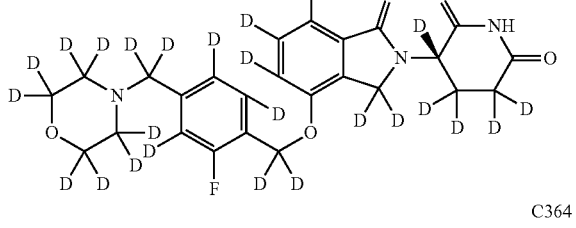
C358
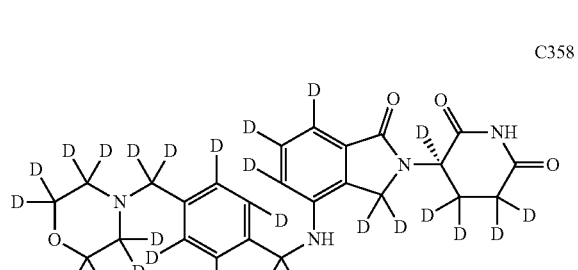
C364
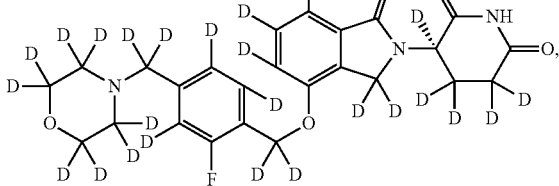
the pharmaceutically acceptable salt and the stereoisomer thereof.
In the combination, the one or more of the benzoheterocyclic compound of formula (I), the pharmaceutically acceptable salt, solvate, polymorph, co-crystal, stereoisomer, isotope compound, metabolite and prodrug thereof is more preferably any one of the following compounds: B101, B102, B103, B104, B105, B106, C107, C108, C109, C110, C111, C112, the pharmaceutically acceptable salt and the stereoisomer thereof. The one or more of the benzoheterocyclic compound of formula (I), the pharmaceutically acceptable salt, solvate, polymorph, co-crystal, stereoisomer, isotope compound, metabolite and prodrug thereof is most preferably any one of the following compounds: B101, B102, B103, B104, B105, B106, C111, the pharmaceutically acceptable salt and the stereoisomer thereof.

In the combination, the androgen receptor pathway modulator is preferably selected from one or more of Enzalutamide, ARN-509, Abiraterone, Abiraterone acetate, Galeterone, ODM-201 and ORM-15341.

In the combination, the androgen receptor pathway modulator is more preferably Enzalutamide, ARN-509, Galeterone, ODM-201, ORM-15341, Abiraterone, Abiraterone acetate, Enzalutamide and Galeterone, Enzalutamide and Abiraterone acetate, Enzalutamide and Abiraterone, Enzalutamide and ODM-201, Enzalutamide and ORM-15341, ARN-509 and Galeterone, ARN-509 and Abiraterone acetate, ARN-509 and Abirateron, ARN-509 and ODM-201, ARN-509 and ORM-15341, ODM-201 and Galeterone, ODM-201 and Abiraterone acetate, ODM-201 and Abiraterone, ORM-15341 and Galeterone, ORM-15341 and Abiraterone acetate, or ORM-15341 and Abiraterone.

In the combination, the androgen receptor pathway modulator is most preferably Enzalutamide, ARN-509, Galeterone, ODM-201, Abiraterone, Abiraterone acetate, Enzalutamide and Galeterone, Enzalutamide and Abiraterone acetate, ARN-509 and Galeterone, ARN-509 and Abiraterone acetate, ODM-201 and Enzalutamide, ODM-201 and ARN-509, ODM-201 and Galeterone, ODM-201 and Abiraterone, or ODM-201 and Abiraterone acetate.

In some embodiments, the combination of "one or more of the benzoheterocyclic compound of formula (I), the pharmaceutically acceptable salt, solvate, polymorph, co-crystal, stereoisomer, isotope compound, metabolite and prodrug thereof" and the androgen receptor pathway modulator is that: the "one or more of the benzoheterocyclic compound of formula (I), the pharmaceutically acceptable salt, solvate, polymorph, co-crystal, stereoisomer, isotope compound, metabolite and prodrug thereof" is selected from B101, B102, B103, B104, B105, B106, C107, C108, C109, C110, C111, C112, the pharmaceutically acceptable salt and the stereoisomer thereof; the androgen receptor pathway modulator is selected from one or more of Enzalutamide, ARN-509, Abiraterone, Abiraterone acetate, Galeterone, ODM-201 and ORM-15341.

In some embodiments, the combination of "one or more of the benzoheterocyclic compound of formula (I), the pharmaceutically acceptable salt, solvate, polymorph, co-crystal, stereoisomer, isotope compound, metabolite and prodrug thereof" and the androgen receptor pathway modulator is that: the "one or more of the benzoheterocyclic compound of formula (I), the pharmaceutically acceptable salt, solvate, polymorph, co-crystal, stereoisomer, isotope compound, metabolite and prodrug thereof" is selected from B101, B102, B103, B104, B105, B106, C107, C108, C109, C110, C111, C112, the pharmaceutically acceptable salt and the stereoisomer thereof; the androgen receptor pathway modulator is Enzalutamide, ARN-509, Galeterone, ODM-201, ORM-15341, Abiraterone, Abiraterone acetate, Enzalutamide and Galeterone, Enzalutamide and Abiraterone acetate, Enzalutamide and Abiraterone, Enzalutamide and ODM-201, Enzalutamide and ORM-15341, ARN-509 and Galeterone, ARN-509 and Abiraterone acetate, ARN-509 and Abirateron, ARN-509 and ODM-201, ARN-509 and ORM-15341, ODM-201 and Galeterone, ODM-201 and Abiraterone acetate, ODM-201 and Abiraterone, ORM-15341 and Galeterone, ORM-15341 and Abiraterone acetate, or ORM-15341 and Abiraterone.

In some embodiments, the combination of "one or more of the benzoheterocyclic compound of formula (I), the pharmaceutically acceptable salt, solvate, polymorph, co-crystal, stereoisomer, isotope compound, metabolite and prodrug thereof" and the androgen receptor pathway modulator is that: the "one or more of the benzoheterocyclic compound of formula (I), the pharmaceutically acceptable salt, solvate, polymorph, co-crystal, stereoisomer, isotope compound, metabolite and prodrug thereof" is selected from B101, B102, B103, B104, B105, B106, C107, C108, C109, C110, C111, C112, the pharmaceutically acceptable salt and the stereoisomer thereof; the androgen receptor pathway modulator is Enzalutamide, ARN-509, Galeterone, ODM-201, Abiraterone, Abiraterone acetate, Enzalutamide and Galeterone, Enzalutamide and Abiraterone acetate, ARN-509 and Galeterone, ARN-509 and Abiraterone acetate, ODM-201 and Enzalutamide, ODM-201 and ARN-509, ODM-201 and Galeterone, ODM-201 and Abiraterone, or ODM-201 and Abiraterone acetate.

In some embodiments, the combination of the benzoheterocyclic compound of formula (I) and the androgen receptor pathway modulator is more preferably that: B101 and Enzalutamide, B102 and Enzalutamide, B103 and Enzalutamide, B104 and Enzalutamide, B105 and Enzalutamide, B106 and Enzalutamide, C111 and Enzalutamide, B101 and ARN-509, B102 and ARN-509, B103 and ARN-509, B104 and ARN-509, B105 and ARN-509, B106 and ARN-509, C111 and ARN-509, B101 and Abiraterone, B102 and Abiraterone, B103 and Abiraterone, B104 and Abiraterone, B105 and Abiraterone, B106 and Abiraterone, C111 and Abiraterone, B101 and Abiraterone acetate, B102 and Abiraterone acetate, B103 and Abiraterone acetate, B104 and Abiraterone acetate, B105 and Abiraterone acetate, B106 and Abiraterone acetate, C111 and Abiraterone acetate, B101 and Galeterone, B102 and Galeterone, B103 and Galeterone, B104 and Galeterone, B105 and Galeterone, B106 and Galeterone, C111 and Galeterone, B101 and ODM-201, B102 and ODM-201, B103 and ODM-201, B104 and ODM-201, B105 and ODM-201, B106 and ODM-201, C111 and ODM-201, B101 and Enzalutamide and Galeterone, B102 and Enzalutamide and Galeterone, B103 and Enzalutamide and Galeterone, B104 and Enzalutamide and Galeterone, B105 and Enzalutamide and Galeterone, B106 and Enzalutamide and Galeterone, C111 and Enzalutamide and Galeterone, B101 and Enzalutamide and Abiraterone acetate, B102 and Enzalutamide and Abiraterone acetate, B103 and Enzalutamide and Abiraterone acetate, B104 and Enzalutamide and Abiraterone acetate, B105 and Enzalutamide and Abiraterone acetate, B106 and Enzalutamide and Abiraterone acetate, C111 and Enzalutamide and Abiraterone acetate, B101 and ARN-509 and Galeterone, B102 and ARN-509 and Galeterone, B103 and ARN-509 and Galeterone, B104 and ARN-509 and Galeterone, B105 and ARN-509 and Galeterone, B106 and ARN-509 and Galeterone, C111 and ARN-509 and Galeterone, B101 and ARN-509 and Abiraterone acetate, B102 and ARN-509 and Abiraterone acetate, B103 and ARN-509 and Abiraterone acetate, B104 and ARN-509 and Abiraterone acetate, B105 and ARN-509 and Abiraterone acetate, B106 and ARN-509 and Abiraterone acetate, C111 and ARN-509 and Abiraterone acetate, B101 and ODM-201 and Enzalutamide, B102 and ODM-201 and Enzalutamide, B103 and ODM-201 and Enzalutamide, B104 and ODM-201 and Enzalutamide, B105 and ODM-201 and Enzalutamide, B106 and ODM-201 and Enzalutamide, C111 and ODM-201 and Enzalutamide, B101 and ODM-201 and ARN-509, B102 and ODM-201 and ARN-509, B103 and ODM-201 and ARN-509, B104 and ODM-201 and ARN-509, B105 and ODM-201 and ARN-509, B106 and ODM-201 and ARN-509, C111 and ODM-201 and ARN-509, B101 and ODM-201 and Galeterone, B102 and ODM-201 and Galeterone, B103 and ODM-201 and Galeterone, B104 and ODM-201 and Galeterone, B105 and ODM-201 and Galeterone, B106 and ODM-201 and Galeterone, C111 and ODM-201 and Galeterone, B101 and ODM-201 and Abiraterone, B102 and ODM-201 and Abiraterone, B103 and ODM-201 and Abiraterone, B104 and ODM-201 and Abiraterone, B105 and ODM-201 and Abiraterone, B106 and ODM-201 and Abiraterone, C111 and ODM-201 and Abiraterone, B101 and ODM-201 and Abiraterone acetate, B102 and ODM-201 and Abiraterone acetate, B103 and ODM-201 and Abiraterone acetate, B104 and ODM-201 and Abiraterone acetate, B105 and ODM-201 and Abiraterone acetate, B106 and ODM-201 and Abiraterone acetate, or C111 and ODM-201 and Abiraterone acetate.

In some embodiments, the combination of the pharmaceutically acceptable salt of the benzoheterocyclic compound of formula (I) and the androgen receptor pathway modulator is preferably as any one of the combinations described in the above paragraph, with the only difference of replacing "the benzoheterocyclic compound of formula (I)" with "the pharmaceutically acceptable salt of the benzoheterocyclic compound of formula (I)". For example, the combination of B101 and Enzalutamide in the above paragraph corresponds to the pharmaceutically acceptable salt of B101 and enzalutamide in this paragraph.

In some embodiments, the combination of the stereoisomers of the benzoheterocyclic compound of formula (I) and the androgen receptor pathway modulator is preferably as any one of the combinations described in the above paragraph, with the only difference of replacing "the pharmaceutically acceptable salt of the benzoheterocyclic compound of the formula (I)" with "the stereoisomers of the benzoheterocyclic compound of formula (I)". For example, the combination of the pharmaceutically acceptable salt of B101 and Enzalutamide in the above paragraph corresponds to the stereoisomers of B101 and enzalutamide in this paragraph.

The combination may further comprise hormone compound, the hormone compound is one or more of prednisone, dexamethasone, dehydroepiandrosterone, isoandrosterone and megestrol acetate. The hormone compound is preferably prednisone. Therefore, the combination may comprise one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator and the hormone compound.

In the combination, the combination of the androgen receptor pathway modulator and the hormone compound is preferably Galeterone and prednisone, prednisone and Abiraterone acetate, Enzalutamide and prednisone, ARN-509 and prednisone, Enzalutamide and dexamethasone, Enzalutamide and Galeterone and prednisone, Enzalutamide and Galeterone and dexamethasone, Enzalutamide and ODM-201 and prednisone, Enzalutamide and ODM-201 and dexamethasone, Enzalutamide and ORM-15341 and prednisone, Enzalutamide and ORM-15341 and dexamethasone, Enzalutamide and Abiraterone acetate and prednisone, Enzalutamide and Abiraterone acetate and dexamethasone, Enzalutamide and Abiraterone and prednisone, Enzalutamide and Abiraterone and dexamethasone, ARN-509 and dexamethasone, ARN-509 and Galeterone and prednisone, ARN-509 and Galeterone and dexamethasone, ARN-509 and ODM-201 and prednisone, ARN-509 and ODM-201 and dexamethasone, ARN-509 and ORM-15341 and prednisone, ARN-509 and ORM-15341 and dexamethasone, ARN-509 and Abiraterone acetate and prednisone, ARN-509 and Abiraterone acetate and dexamethasone, ARN-509 and Abiraterone and prednisone, ARN-509 and Abiraterone and dexamethasone, ODM-201 and prednisone, ODM-201 and dexamethasone, ODM-201 and Galeterone and prednisone, ODM-201 and Galeterone and dexamethasone, ODM-201 and Abiraterone acetate and prednisone, ODM-201 and Abiraterone acetate and dexamethasone, ODM-201 and Abiraterone and prednisone, ODM-201 and Abiraterone and dexamethasone, ORM-15341 and prednisone, ORM-15341 and dexamethasone, ORM-15341 and Galeterone and prednisone, ORM-15341 and Galeterone and dexamethasone, ORM-15341 and Abiraterone acetate and prednisone, ORM-15341 and Abiraterone acetate and dexamethasone, ORM-15341 and Abiraterone and prednisone, ORM-15341 and Abiraterone and dexamethasone, Galeterone and dexamethasone or Abiraterone acetate and dexamethasone.

In the combination, the combination of the androgen receptor pathway modulator and the hormone compound is more preferably Galeterone and prednisone, prednisone and Abiraterone acetate, Enzalutamide and prednisone, ARN-509 and prednisone, Enzalutamide and Galeterone and prednisone, Enzalutamide and ODM-201 and prednisone, Enzalutamide and ORM-15341 and prednisone, Enzalutamide and Abiraterone acetate and prednisone, Enzalutamide and Abiraterone and prednisone, ARN-509 and Galeterone and prednisone, ARN-509 and ODM-201 and prednisone, ARN-509 and ORM-15341 and prednisone, ARN-509 and Abiraterone acetate and prednisone, ARN-509 and Abiraterone and prednisone, ODM-201 and prednisone, ODM-201 and Galeterone and prednisone, ODM-201 and Abiraterone acetate and prednisone, ODM-201 and Abiraterone and prednisone, ORM-15341 and prednisone, ORM-15341 and Galeterone and prednisone, ORM-15341 and Abiraterone acetate and prednisone or ORM-15341 and Abiraterone and prednisone.

In the combination, the combination of the androgen receptor pathway modulator and the hormone compound is most preferably Galeterone and prednisone, prednisone and Abiraterone acetate, Enzalutamide and prednisone, ARN-509 and prednisone, Enzalutamide and Galeterone and prednisone, Enzalutamide and Abiraterone acetate and prednisone, ARN-509 and Galeterone and prednisone, ARN-509 and Abiraterone acetate and prednisone, ODM-201 and prednisone, ODM-201 and Galeterone and prednisone, ODM-201 and Abiraterone acetate and prednisone, ODM-201 and Abiraterone and prednisone, Enzalutamide and ODM-201 and prednisone or ARN-509 and ODM-201 and prednisone.

In some embodiments of the invention, the combination of "one or more of the benzoheterocyclic compound of formula (I), the pharmaceutically acceptable salt, solvate, polymorph, co-crystal, stereoisomer, isotope compound, metabolite and prodrug thereof" and the androgen receptor pathway modulator and the hormone compound is preferably that: the "one or more of the benzoheterocyclic compound of formula (I), the pharmaceutically acceptable salt, solvate, polymorph, co-crystal, stereoisomer, isotope compound, metabolite and prodrug thereof" is selected from B101, B102, B103, B104, B105, B106, C107, C108, C109, C110, C111, C112, the pharmaceutically acceptable salt and the stereoisomer thereof; The combination of the androgen receptor pathway modulator and the hormone compound is Galeterone and prednisone, prednisone and Abiraterone acetate, Enzalutamide and prednisone, ARN-509 and prednisone, Enzalutamide and Galeterone and prednisone, Enzalutamide and Abiraterone acetate and prednisone, ARN-509 and Galeterone and prednisone, ARN-509 and Abiraterone acetate and prednisone, ODM-201 and prednisone, ODM-201 and Galeterone and prednisone, ODM-201 and Abiraterone acetate and prednisone, ODM-201 and Abiraterone and prednisone, Enzalutamide and ODM-201 and prednisone, or, ARN-509 and ODM-201 and prednisone.

In some embodiments of the invention, the combination of the benzoheterocyclic compound of formula (I) and the androgen receptor pathway modulator and the hormone compound is more preferably B101 and Enzalutamide and prednisone, B102 and Enzalutamide and prednisone, B103 and Enzalutamide and prednisone, B104 and Enzalutamide and prednisone, B105 and Enzalutamide and prednisone, B106 and Enzalutamide and prednisone, C111 and Enzalutamide and prednisone, B101 and ARN-509 and prednisone, B102 and ARN-509 and prednisone, B103 and ARN-509 and prednisone, B104 and ARN-509 and prednisone, B105 and ARN-509 and prednisone, B106 and ARN-509 and prednisone, C111 and ARN-509 and prednisone, B101 and Galeterone and prednisone, B102 and Galeterone and prednisone, B103 and Galeterone and prednisone, B104 and Galeterone and prednisone, B105 and Galeterone and prednisone, B106 and Galeterone and prednisone, C111 and Galeterone and prednisone, B101 and ODM-201 and prednisone, B102 and ODM-201 and prednisone, B103 and ODM-201 and prednisone, B104 and ODM-201 and prednisone, B105 and ODM-201 and prednisone, B106 and ODM-201 and prednisone, C111 and ODM-201 and prednisone, B101 and prednisone and Abiraterone acetate, B102 and prednisone and Abiraterone acetate, B103 and prednisone and Abiraterone acetate, B104 and prednisone and Abiraterone acetate, B105 and prednisone and Abiraterone acetate, B106 and prednisone and Abiraterone acetate, C111 and prednisone and Abiraterone acetate, B101 and Enzalutamide and Galeterone and prednisone, B102 and Enzalutamide and Galeterone and prednisone, B103 and Enzalutamide and Galeterone and prednisone, B104 and Enzalutamide and Galeterone and prednisone, B105 and Enzalutamide and Galeterone and prednisone, B106 and Enzalutamide and Galeterone and prednisone, C111 and Enzalutamide and Galeterone and prednisone, B101 and Enzalutamide and Abiraterone acetate and prednisone, B102 and Enzalutamide and Abiraterone acetate and prednisone, B103 and Enzalutamide and Abiraterone acetate and prednisone, B104 and Enzalutamide and Abiraterone acetate and prednisone, B105 and Enzalutamide and Abiraterone acetate and prednisone, B106 and Enzalutamide and Abiraterone acetate and prednisone, C111 and Enzalutamide and Abiraterone acetate and prednisone, B101 and ARN-509 and Galeterone and prednisone, B102 and ARN-509 and Galeterone and prednisone, B103 and ARN-509 and Galeterone and prednisone, B104 and ARN-509 and Galeterone and prednisone, B105 and ARN-509 and Galeterone and prednisone, B106 and ARN-509 and Galeterone and prednisone, C111 and ARN-509 and Galeterone and prednisone, B101 and ARN-509 and Abiraterone acetate and prednisone, B102 and ARN-509 and Abiraterone acetate and prednisone, B103 and ARN-509 and Abiraterone acetate and prednisone, B104 and ARN-509 and Abiraterone acetate and prednisone, B105 and ARN-509 and Abiraterone acetate and prednisone, B106 and ARN-509 and Abiraterone acetate and prednisone, C111 and ARN-509 and Abiraterone acetate and prednisone, B101 and ODM-201 and Enzalutamide and prednisone, B102 and ODM-201 and Enzalutamide and prednisone, B103 and ODM-201 and Enzalutamide and prednisone, B104 and ODM-201 and Enzalutamide and prednisone, B105 and ODM-201 and Enzalutamide and prednisone, B106 and ODM-201 and Enzalutamide and prednisone, C111 and ODM-201 and Enzalutamide and prednisone, B101 and ODM-201 and ARN-509 and prednisone, B102 and ODM-201 and ARN-509 and prednisone, B103 and ODM-201 and ARN-509 and prednisone, B104 and ODM-201 and ARN-509 and prednisone, B105 and ODM-201 and ARN-509 and prednisone, B106 and ODM-201 and ARN-509 and prednisone, C111 and ODM-201 and ARN-509 and prednisone, B101 and ODM-201 and Galeterone and prednisone, B102 and ODM-201 and Galeterone and prednisone, B103 and ODM-201 and Galeterone and prednisone, B104 and ODM-201 and Galeterone and prednisone, B105 and ODM-201 and Galeterone and prednisone, B106 and ODM-201 and Galeterone and prednisone, C111 and ODM-201 and Galeterone and prednisone, B101 and ODM-201 and Abiraterone and prednisone, B102 and ODM-201 and Abiraterone and prednisone, B103 and ODM-201 and Abiraterone and prednisone, B104 and ODM-201 and Abiraterone and prednisone, B105 and ODM-201 and Abiraterone and prednisone, B106 and ODM-201 and Abiraterone and prednisone, C111 and ODM-201 and Abiraterone and prednisone, B101 and ODM-201 and Abiraterone acetate and prednisone, B102 and ODM-201 and Abiraterone acetate and prednisone, B103 and ODM-201 and Abiraterone acetate and prednisone, B104 and ODM-201 and Abiraterone acetate and prednisone, B105 and ODM-201 and Abiraterone acetate and prednisone, B106 and ODM-201 and Abiraterone acetate and prednisone, or, C111 and ODM-201 and Abiraterone acetate and prednisone.

In some embodiments, the combination of the pharmaceutically acceptable salt of the benzoheterocyclic compound of formula (I) and the androgen receptor pathway modulator and the hormone compound is more preferably as any one of the combinations described in the above paragraph, with the only difference of replacing "the benzoheterocyclic compound of formula (I)" with "the pharmaceutically acceptable salt of the benzoheterocyclic compound of formula (I)". For example, the combination of B101 and Enzalutamide and prednisone in the above paragraph corresponds to the pharmaceutically acceptable salt of B101 and enzalutamide and prednisone in this paragraph.

In some embodiments, the combination of the stereoisomers of the benzoheterocyclic compound of formula (I) and the androgen receptor pathway modulator and the hormone compound is more preferably as any one of the combinations described in the above paragraph, with the only difference of replacing "the pharmaceutically acceptable salt of the benzoheterocyclic compound of formula (I)" with "the stereoisomer of the benzoheterocyclic compound of formula (I)". For example, the combination of the pharmaceutically acceptable salt of B101 and Enzalutamide and prednisone in the above paragraph corresponds to the stereoisomer of B101 and enzalutamide and prednisone in this paragraph.

Each of the components in the combination may be administered simultaneously or separately (eg, sequentially); when the components in the combination are administered simultaneously, the components in the combination may be uniformly mixed (ie, the mixture of components).

The components in the combination may be formulated into a single pharmaceutical composition for simultaneous administration, or each of the components may be individually formulated into a single independent pharmaceutical composition which may be administered simultaneously or separately (eg, sequentially).

In the invention, the term "component" refers to a component in the combination of the invention, that is one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator or the hormone compound.

The present invention further provides a pharmaceutical composition, comprising the above combination and one or more pharmaceutically acceptable excipients.

In one aspect, the pharmaceutical composition of the invention may comprise the above one or more of the benzoheterocyclic compound of formula (I), the pharmaceutically acceptable salt, solvate, polymorph, co-crystal, stereoisomer, isotope compound, metabolite and prodrug thereof, the above androgen receptor pathway modulator, and one or more pharmaceutically acceptable excipients.

In another aspect, the pharmaceutical composition of the invention may comprise the above one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator mentioned above, the above hormone compound, and one or more pharmaceutically acceptable excipients.

The pharmaceutically acceptable excipients can be those widely used in drug manufacture field. The excipient is mainly used to provide a safe, stable and functionalized pharmaceutical composition, and can also provide a method which makes the active ingredients dissolved at a desired rate after the subject receives administration or promotes the efficacy of absorption of the active ingredients after the subject is administered with the composition. The excipient can be an inert filler, or provide a certain function, such as stabilizing the overall pH value of the composition or preventing the degradation of the active ingredients of the composition. The pharmaceutically acceptable excipient may comprise one or more of the following excipients: binder, suspending agent, emulsifier, diluent, filler, granulating agent, adhesive, disintegrating agent, lubricant, anti-adhesive agent, glidant, wetting agent, gelling agent, absorption retarder, dissolution inhibitor, reinforcing agent, adsorbent, buffer, chelating agent, preservative, colorant, flavoring agent and sweetening agent.

The pharmaceutical composition may consist of the combination and one or more pharmaceutically acceptable excipients.

The methods of preparing pharmaceutical compositions known to people skilled in the art include but not limited to conventional mixing, dissolving, granulating, emulsifying, grinding, encapsulating, embedding or lyophilization. For example, the pharmaceutical composition of the present invention can be prepared by mixing one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator and the pharmaceutically acceptable excipient, or by mixing one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator, the hormonal compound and the pharmaceutically acceptable excipient.

The pharmaceutical composition of the present invention may be formulated into any form for administration, including injection (intravenous), mucosal, oral administration (solid and liquid preparation), inhalation, ocular administration, rectal administration, topical or parenteral (infusion, injection, implantation, subcutaneous, vein, artery, intramuscular) administration. The pharmaceutical composition of the present invention can also be a controlled release or delayed release preparation. Examples of solid oral preparations include but not limited to powder, capsule, caplet, soft capsule, pill and tablet. Examples of liquid preparations for oral or mucosal administration include but not limited to suspension, emulsion, elixir and solution. Examples of preparations for topical administration include but not limited to emulsion, gel, ointment, cream, patch, paste, foam, lotion, drops or serum preparation. Examples of preparations for parenteral administration include but not limited to injection solution, dry preparation which can be dissolved or suspended in a pharmaceutically acceptable carrier, injection suspension and injection emulsion. Examples of other suitable preparations of the pharmaceutical composition, include but not limited to eye drops and other ophthalmic preparations; aerosol, such as nasal spray or inhalation; liquid dosage forms suitable for parenteral administration; suppository and pastille.

In some embodiments, the pharmaceutical composition of the present invention relates to a controlled release preparation. As used herein, "controlled release preparation" refers to a preparation, wherein the therapeutic active ingredient of the pharmaceutical composition has a controlled release rate, or a specific delay to control the release site of the therapeutic active ingredient in the subject administered with the pharmaceutical composition. One controlled release preparation may comprise a controlled release agent, such as a sustained release agent (sustained release) and/or a delayed release agent (delayed release).

As used herein, the term "sustained release" refers to prolonging the release of the therapeutic active ingredient from the pharmaceutical formulation. As used herein, the term "delayed release" refers to that the therapeutic active ingredient releases from the pharmaceutical composition at a specific site or in a desired environment when the composition reaches the desired environment in the subject who has received administration or after a specific period of time since the subject receives administration.

As used herein, the terms "sustained release agent" and "delayed release agent" refer to a compound or an additive which controls the releasing of the therapeutic active ingredient from the composition, so as to make the release gradually and prolong the time of release. The sustained or delayed release agent may make the therapeutic active ingredient released within a specific period of time after the composition was administered to a subject.

The "controlled release" from the controlled release preparation of the pharmaceutical composition of the present invention can be achieved by a variety of conditions, including but not limited to pH, temperature, enzymes, water, or other physiological conditions or compounds. The pharmaceutical composition of the present invention may further comprise an enteric coating which controls the release of the active ingredient in the pharmaceutical composition, making it released gradually and continuously from the composition in a desired period of time, so that the active ingredient can play a therapeutic or preventive role for an extended period of time. One skilled in the art may be familiar with those appropriate controlled release agents, sustained and delayed release agents based on the disclosed contents. Unrestrictive examples of the controlled release agents which can be incorporated into the pharmaceutical composition of the present invention in order to provide a controlled release composition include polymers (such as hydroxypropyl methyl cellulose), gel, permeable membrane, particle, liposome, microsphere and the combination thereof. Any composition described herein may be suitable for the controlled release preparation, such as tablet, capsule, soft capsule and caplet.

In another aspect, the invention provides a kit, comprising pharmaceutical composition A and pharmaceutical composition B;

The pharmaceutical composition A comprises one or more of the benzoheterocyclic compound of formula (I), the pharmaceutically acceptable salt, solvate, polymorph, co-crystal, stereoisomer, isotope compound, metabolite and prodrug thereof and one or more pharmaceutically acceptable excipients; The pharmaceutical composition B comprises the androgen receptor pathway modulator and one or more pharmaceutically acceptable excipients.

The kit may consist of the pharmaceutical composition A and the pharmaceutical composition B. The pharmaceutical composition A may consist of one or more of the benzoheterocyclic compound of formula (I), the pharmaceutically acceptable salt, solvate, polymorph, co-crystal, stereoisomer, isotope compound, metabolite and prodrug thereof and one or more pharmaceutically acceptable excipients; The pharmaceutical composition B may consist of the androgen receptor pathway modulator and one or more pharmaceutically acceptable excipients. The one or more of the benzoheterocyclic compound of formula (I), the pharmaceutically acceptable salt, solvate, polymorph, co-crystal, stereoisomer, isotope compound, metabolite and prodrug thereof in the pharmaceutical composition A, the androgen receptor pathway modulator in the pharmaceutical composition B, and the combination thereof are preferably as described above.

The kit may further comprise a pharmaceutical composition C, which comprises the hormone compound as described above and one or more pharmaceutically acceptable excipients.

The kit may consist of the pharmaceutical composition A, the pharmaceutical composition B and the pharmaceutical composition C. The pharmaceutical composition C may consist of the hormone compound as described above and one or more pharmaceutically acceptable excipients; Preferably, the one or more of the benzoheterocyclic compound of formula (I), the pharmaceutically acceptable salt, solvate, polymorph, co-crystal, stereoisomer, isotope compound, metabolite and prodrug thereof in the pharmaceutical composition A, the androgen receptor pathway modulator in the pharmaceutical composition B, the hormone compound in the pharmaceutical composition C, and the combination thereof are as described above.

The pharmaceutical compositions in the kit may be administered simultaneously or separately (eg, sequentially).

In the kit, the term "pharmaceutically acceptable excipients" has the same definition as above.

In the invention, the term "active ingredient" refers to the active ingredient in the pharmaceutical composition or the kit of the invention, that is, one or more of the compound of formula (I), the pharmaceutically acceptable salt, solvate, polymorph, co-crystal, stereoisomer, isotope compound, metabolite and prodrug thereof, the androgen receptor pathway modulator, the hormone compound, or the above combination thereof.

The above combination, the above pharmaceutical composition or the above kit can be used for the prevention and/or treatment of prostate cancer. The prostate cancer is preferably castration-resistant prostate cancer.

In another aspect, the invention provides use of the above one or more of the benzoheterocyclic compound of formula (I), the pharmaceutically acceptable salt, solvate, polymorph, co-crystal, stereoisomer, isotope compound, metabolite and prodrug thereof, in the manufacture of a medicament for the prevention and/or treatment of prostate cancer in combination with the above androgen receptor pathway modulator.

In another aspect, the invention provides use of the above one or more of the benzoheterocyclic compound of formula (I), the pharmaceutically acceptable salt, solvate, polymorph, co-crystal, stereoisomer, isotope compound, metabolite and prodrug thereof, in the manufacture of a medicament for the prevention and/or treatment of prostate cancer in combination with the above androgen receptor pathway modulator and the above hormone compound.

The invention provides use of the above androgen receptor pathway modulator, in the manufacture of a medicament for the prevention and/or treatment of prostate cancer in combination with the above one or more of the benzoheterocyclic compound of formula (I), the pharmaceutically acceptable salt, solvate, polymorph, co-crystal, stereoisomer, isotope compound, metabolite and prodrug thereof.

The invention provides use of the above androgen receptor pathway modulator, in the manufacture of a medicament for the prevention and/or treatment of prostate cancer in combination with the above one or more of the benzoheterocyclic compound of formula (I), the pharmaceutically acceptable salt, solvate, polymorph, co-crystal, stereoisomer, isotope compound, metabolite and prodrug thereof and the above hormone compound.

The invention provides use of the above hormone compound, in the manufacture of a medicament for the prevention and/or treatment of prostate cancer in combination with the above one or more of the benzoheterocyclic compound of formula (I), the pharmaceutically acceptable salt, solvate, polymorph, co-crystal, stereoisomer, isotope compound, metabolite and prodrug thereof and the above androgen receptor pathway modulator.

In the use of the invention, the above one or more of the benzoheterocyclic compound of formula (I), the pharmaceutically acceptable salt, solvate, polymorph, co-crystal, stereoisomer, isotope compound, metabolite and prodrug thereof, the above androgen receptor pathway modulator and the above hormone compound may be administered simultaneously or separately (eg, sequentially).

In the above use, the one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator, the hormone compound and the combination thereof are as described above.

In another aspect, the invention provides a method of prevention and/or treatment of prostate cancer, comprising administration of a therapeutically or prophylactically effective amount of the above combination to the patients in need. The prostate cancer can be castration-resistant prostate cancer.

In an embodiment, the method of prevention and/or treatment of prostate cancer, comprises administration of a therapeutically or prophylactically effective amount of the above one or more of the benzoheterocyclic compound of formula (I), the pharmaceutically acceptable salt, solvate, polymorph, co-crystal, stereoisomer, isotope compound, metabolite and prodrug thereof and a therapeutically or prophylactically effective amount of the above androgen receptor pathway modulator to the patients in need;

Wherein, the above one or more of the benzoheterocyclic compound of formula (I), the pharmaceutically acceptable salt, solvate, polymorph, co-crystal, stereoisomer, isotope compound, metabolite and prodrug thereof and the above androgen receptor pathway modulator may be administered simultaneously or separately (eg, sequentially).

In some embodiments of the invention, the method of prevention and/or treatment of prostate cancer preferably comprises administration of a therapeutically or prophylactically effective amount of the above one or more of the benzoheterocyclic compound of formula (I), the pharmaceutically acceptable salt, solvate, polymorph, co-crystal, stereoisomer, isotope compound, metabolite and prodrug thereof, a therapeutically or prophylactically effective amount of the above androgen receptor pathway modulator and a therapeutically or prophylactically effective amount of the above hormone compound to the patients in need.

Wherein, the above one or more of the benzoheterocyclic compound of formula (I), the pharmaceutically acceptable salt, solvate, polymorph, co-crystal, stereoisomer, isotope compound, metabolite and prodrug thereof, the above androgen receptor pathway modulator and the above hormone compound may be administered simultaneously or separately (eg, sequentially).

In the method of prevention and/or treatment of prostate cancer, the one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator, the hormone compound and the combination thereof are as described above.

In some embodiments, the therapeutically or prophylactically effective amount of the compound (herein referred as to one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator, or the hormone compound) administered to each subject is from about 0.005 to about 1000 mg/day, from about 0.01 to about 500 mg/day, from about 0.01 to about 250 mg/day, from about 0.01 to about 100 mg/day, from about 0.1 to about 100 mg/day, from about 0.5 to about 100 mg/day, from about 1 to about 100 mg/day, from about 0.01 to about 50 mg/day, from about 0.1 to about 50 mg/day, from about 0.5 to about 50 mg/day, from about 1 to about 50 mg/day, from about 0.02 to about 25 mg/day, or from about 0.05 to about 10 mg/day.

In some embodiments, the therapeutically or prophylactically effective amount (herein referred as to the therapeutically or prophylactically effective amount of one or more of the benzoheterocyclic compound of formula (I), the pharmaceutically acceptable salt, solvate, polymorph, co-crystal, stereoisomer, isotope compound, metabolite and prodrug thereof, the androgen receptor pathway modulator, or the hormone compound) is about 0.01, about 0.05, about 0.1, about 0.2, about 0.3, about 0.4, about 0.5, about 0.6, about 0.8, about 1, about 2, about 5, about 10, about 15, about 20, about 25, about 30, about 40, about 45, about 50, About 60, about 70, about 80, about 90, about 100, about 150, about 200, about 250, about 300, about 350, about 400, about 450, about 500, about 550, about 600, about 650, about 700 About 750, about 800, about 850, about 900, or about 1000 mg/day/subject.

In the combination, the pharmaceutical composition, the kit, the use or the method of prevention and/or treatment of prostate cancer of the invention, the mole ratio of the benzoheterocyclic compound of formula (I) and the androgen receptor pathway modulator, can be selected in accordance with the conventional art, for example, 1:0.0002-1:300, for example, 1:0.0005-1:222 (1:0.0002, 1:0.0005, 1:0014, 1:0.0041, 1:0.012, 1:0.0037, 1:0.11, 1:0.33, 1:1, 1:3, 1:9, 1:27, 1:79, 1:222), for example, 1:0.1-1:222.

In the combination, the pharmaceutical composition, the kit, the use or the method of prevention and/or treatment of prostate cancer of the invention, the amount of the benzoheterocyclic compound of formula (I) and the androgen receptor pathway modulator is not particularly limited, which can be selected in accordance with the conventional art, the amount of the benzoheterocyclic compound of formula (I) can be for example, 0.001-300 µM, for example, 0.05-300 µM (for example, 300.00 µM, 100.00 µM, 33.33 µM, 11.11 µM, 3.70 µM, 1.23 µM, 0.41 µM, 0.14 µM or 0.05 µM); the amount of the androgen receptor pathway modulator can be 0.01-300 µM, for example, 0.05-50 µM, for example, 0.05-11.11 µM.

In the combination, the pharmaceutical composition, the kit, the use or the method of prevention and/or treatment of prostate cancer of the invention, when the hormone compound is further comprised, the amount of the hormone compound is not particularly limited, for example, the mole ratio of the hormone compound and the androgen receptor pathway modulator can be 1:0.01-1:100, for another example, 1:0.1-1:10 (for another example, 1:0.1, 1:1, 2:1, 1:10).

In the combination, the pharmaceutical composition, the kit, the use or the method of prevention and/or treatment of prostate cancer of the invention, when the hormone compound is further comprised, the amount of the hormone compound is not particularly limited, for example, the amount of the hormone compound and the androgen receptor pathway modulator can be individually 0.01-300 µM, for another example, 0.05-50 µM, for another example, 0.1-10 µM.

When each of the components in the combination of the present invention is administered to a subject for the purpose of treating or preventing a disease, disorder or condition, each component in the combination may be administered by the same route or by a different route. The route of administration may be any route described herein, including but not limited to oral, inhalation, injection, ophthalmic, mucosal, rectal, emulsion, liposome, long-acting implant or sustained controlled release method. The specific route of administration will depend on the therapeutic agent itself and the preparation, as well as the disease, disorder or condition to be prevented or treated. According to the present disclosure, the skill level of an ordinary person skilled in the art is sufficient to determine the route of administration. Each of the components in the combination of the present invention may be administered to the subject within a period of time (administration period) followed by a period of no administration of the compound (non-administration period). The administration period and non-administration period can be repeated for desired times. The desired length and times of the administration period or non-administration period will depend on the type and/or severity of the disease, disorder or condition being treated or prevented, as well as the sex, age, weight, and other parameters (e.g. the individual subject's biological, physical, and physiological status, etc.) of the individual subject. Each of the components in the combination of the present invention may be administered simultaneously to the subject in a period of time and may also be administered to the subject sequentially in a period of time. According to the present disclosure, the skill level of an ordinary person skilled in the art is sufficient to determine the appropriate length and times of administration period and/or non-administration period.

The therapeutic method in the present invention comprises administering each of the components in the combination of the present invention to a subject by any suitable methods, such as injection, mucosal, oral, inhalation, ocular, rectal, long-acting implant, liposome, emulsion or sustained release process.

One skilled in the art will understand that the therapeutically or prophylactically effective amount of each of the components or the active ingredients in the combination, pharmaceutical composition or the kit of the present invention may vary with factors, for a specific subject, such as age, diet, health, etc., the symptom or disease to be treated or prevented, the severity of the disorder or condition, and the complications and types, and the preparations used etc. According to the disclosures in present invention, one skilled in the art can easily determine the desired therapeutically or prophylactically effective amount administered to the subject, so as to induce the desired biological or medical response in the subject.

The combined use of each of the components or the active ingredients in the combination, pharmaceutical composition or the kit according to the present invention may play a synergistic effect in the treatment or prevention of any disease, disorder or condition (such as prostate cancer).

In any of the methods described herein, including but not limited to the above therapeutic methods, applications etc., the combination, the pharmaceutical composition or the kit according to the present invention may be used alone or in combination with ultrasound therapy, radiation therapy (referred to as radiotherapy) or radioimmunotherapy etc., and may also be used in combination with one or more of other pharmacologically active therapeutic agents (hereinafter referred to as "other therapeutic agents"). The amount and type of other therapeutic agents will depend on the disease, disorder or condition to be treated or prevented; the severity of the disease, disorder or condition; factors of the subject administrated with the composition, such as age, weight, physical conditions, etc.; the route of administration, and so on. According to the embodiments of the present invention, the other therapeutic agent may be a natural, semi-synthetic or synthetic compound. In another embodiment, the other therapeutic agent may be a small molecule, such as a synthetic organic or inorganic molecule; or a larger molecule or biomolecule, such as a protein or nucleic acid with pharmacological activity. In another embodiment, the other therapeutic agent may be one or more of a chemotherapeutant, an antiangiogenic drug (also known as an angiogenesis inhibitor), an immunomodulatory agent, an immunotherapeutic agent, a monoclonal antibody, a polyclonal antibody, and a kinase inhibitor.

The chemotherapeutant (chemotherapeutic agent), is a chemically synthesized drug. Currently, the chemotherapeutant is the main drug in the treatment of cancer and some autoimmune diseases, what commonly used are: epirubicin, doxorubicin, daunorubicin, mitomycin, fluorouracil deoxynucleotides and so on.

The antiangiogenic drug inhibits angiogenesis by inhibiting pro-angiogenic growth factor, growth factor receptor or signaling pathway downstream etc., so as to inhibit the growth and metastasis of the tumors, and it mainly includes vascular endothelial growth inhibitor, receptor tyrosine kinase inhibitor, PI3K/AKT/mTOR pathway inhibitor, recombinant fusion protein (e.g. aflibercept) acting on VEGF-A, VEGF-B and placental growth factor, recombinant human endostatin and so on.

The immunomodulatory agent is a drug which can enhance, promote and regulate immune functions and have a certain effect on immune dysfunction, some secondary immunodeficiency diseases and some malignant tumors. In accordance with the functions of the immunomodulatory agent, the immunomodulatory agent is mainly divided into immunosuppressant and immunopotentiator. The former is used for anti-inflammatory, anti-autoimmune reactions, anti-allergy, anti-transplant rejection and anti-tumor, and the latter is for anti-infection, anti-allergy, and anti-tumor. Various kinds of drugs belong to immunosuppressant, including antimetabolic drugs (cyclosporin A, azathioprine, cyclophosphamide, methotrexate, mycophenolate, tacrolimus, mizoribine etc.), glucocorticoid, monoclonal antibody (anti-TNF-alpha/receptor, anti-IFN-γ, and anti-CD25 monoclonal antibody, etc.), cytokines IFN-β, IL-10 and TGF-β, chemicals (leflunomide and 5-HT3 receptor antagonist), non-steroid anti-inflammatory drugs, nucleic acids, statins anti-lipid drugs, HMG coenzyme A reductase inhibitor, plants (*Tripterygium wilfordii*, extract of *Cordyceps sinensis* FTY720, artemisinin and Parviline etc.) and other biological products (cholera toxin B subunit, sNTB-A-Fc fusion protein, CMV-IkappaBa carrier inhibitor and B7-HI inhibitor etc.). There are also various kinds of immunopotentiators, including cytokines (interferon α, interferon γ, thymic peptide, Thymopentin, G-CSF/GM-CSF, IL-2, IL-12, recombinant human erythropoietin, epidermal growth factor, chemokine intercellular adhesion molecule-1, vascular cell adhesion molecule-1, P-selectin, and other intercellular adhesion molecules, etc.), biological products [IVIG, transfer factor, immune riboncleic acid, bacteria and its extract (*Bacillus* Calmette Guerin and its extract, defatted and deactivated *mycobacterium* vaccine, other bacterial extracts, low calcium response V or V antigen LcrV, *Vibrio cholerae* products Zot and *mycobacterium* etc.)], plant drugs (polysaccharides, saponins and other plant ingredients), chemicals (Levamisole, Tagamet, Pidotimod, NS-398 Imiquimod, Propagermanium and liposome etc.), micronutrients (vitamin A/C/D, trace elements iron, zinc, selenium) and others (macrolide antibiotics, aminophylline).

Immunotherapy refers to the modulation of the immune response of a subject to produce the desired therapeutic effect, the immunotherapeutic agent refers to a drug that when administered to a subject modulates the immune system of the subject so as to be sufficient to ultimately reduce the symptoms associated with an adverse immune response or ultimately reduce the symptoms caused by the increase of the required immune response.

The monoclonal antibody refers to a highly uniform antibody, produced by a single B cell clone, targeting only a specific epitope.

The polyclonal antibody refers to different antibodies produced by using an antigen immune receptor that contains multiple antigenic determinants to stimulate multiple B cell clones in the body, targeting multiple antigenic epitopes.

In biochemistry, kinases are enzymes that transfer phosphate groups from high-energy donor molecules (such as ATP) to specific target molecules (substrates); and this process is called phosphorylation; the kinase inhibitor refers to a class of molecules that may bind with kinases and reduce their activity.

The other therapeutic agent includes but not limited to one or more of daratumumab, elotuzumab, palbociclib, panobinostat, nivolumab, pembrolizumab, pemetrexed, topotecan, doxorubicin, bortezomib, gemcitabine, dacarbazine, biaxin, vincristine, azacitidine, CAR-T, rituximab, trastuzumab, PD-1 inhibitor, PD-L1 inhibitor, HDAC inhibitor, androgen receptor pathway regulators other than the aforementioned androgen receptor pathway regulators, docetaxel, clofarabine injection, Ublituximab, romidepsin, BTK inhibitor, erythropoietin, eltrombopag, minocycline and melphalan.

In another embodiment, the therapeutically or prophylactically effective amount of the androgen receptor pathway modulator or the hormone compound in the pharmaceutical composition or the kit of the present invention may be lower than the effective amount when the compound of formula (I), the pharmaceutically acceptable salt, solvate, polymorph, co-crystal, stereoisomer, isotope compound, metabolite and prodrug thereof of the present invention is not administered.

In the present invention, the amount of the compound administered, the therapeutically or prophylactically effective amount, the dosage, the starting dosage and the like are all referred to the amount of a specific compound, for example, a specific heterocyclic compound of formula (I), the pharmaceutically acceptable salt, solvate, polymorph, co-crystal, stereoisomer, isotope compound, metabolite and prodrug thereof, a specific androgen receptor pathway modulator or a specific hormone, rather than a combination of multiple compounds.

In the present invention, the therapeutically or prophylactically effective amount of the androgen receptor pathway modulator or the hormone compound in the method and the guidance for administration can be found in the patents and published patent applications cited herein, and Wells et al, eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000) and other medical literatures.

The term "androgen receptor pathway modulator" in the present invention comprises androgen inhibitor, androgen receptor inhibitor, androgen biosynthesis inhibitor and other drugs that affect the androgen receptor pathway.

The term "hormones" are a class of chemicals that are produced by certain tissues of a normal body, and then diffuse into the blood, and are transported to other tissues in the body by blood circulation to exert special physiological functions. Hormonal compounds include synthetic or natural hormonal chemicals.

As used herein, when referring to a specific salt, composition, and excipient etc. as "pharmaceutically acceptable", it means that the salt, the composition, the excipient etc. are generally non-toxic, safe, and suitable for use in a subject, preferably a mammalian subject, more preferably a human subject The term "pharmaceutically acceptable salt" herein refers to a pharmaceutically acceptable organic or inorganic salt. Examples of the salt include but are not limited to: sulfate, citrate, acetate, oxalate, chloride, bromide, iodide, nitrate, hydrosulfate, phosphate, acid phosphate, isonicotinic acid salt, lactate, salicylic acid salt, acid citrate, tartrate, oleate, tannate, pantothenate, bitartrate, ascorbate, succinate, maleate, gentisinate, fumarate, gluconate, glucuronate, saccharate, formate, benzoate, glutamate, methane sulfonate, ethane sulfonate, benzene sulfonate, p-toluene sulfonate, and embonate (i.e. 1-1-methylene-bis(2-hydroxy-3-naphthoate)). The compounds of the present invention may form pharmaceutically acceptable salts with various amino acids. Suitable alkali salts include but are not limited to, aluminum salt, calcium salt, lithium salt, magnesium salt, potassium salt, sodium salt, zinc salt, bismuth salt and diethanolamine salt. For a review of the pharmaceutically acceptable salts, see Handbook of Pharmaceutical Salts: Properties, Selection, and Use (P. Heinrich Stahl and Camille G. Wermuth, ed., Wiley-VCH, 2002).

As used herein, the term "metabolite" refers to an active substance produced by changes in chemical structure that a drug molecule undergoes in vivo, the active substance is generally a derivative of the aforementioned drug molecule, and can also be chemically modified.

As used herein, the term "polymorph" refers to one or more crystal structures formed by the different arrangement of molecules in the lattice space when crystallized.

As used herein, the term "co-crystal" refers to a multi-component system comprising one or more API (active pharmaceutical ingredient) molecules and one or more object (or ligand) molecules. In the co-crystal, API molecules and object (or ligand) molecules exist as solids at room temperature when they are used as their pure form alone (in order to distinguish co-crystal from solvate or hydrate). From this particular definition, salts in which significant or complete proton exchange occurs between API molecules and guest molecules are excluded. In the co-crystal, API and ligands interact through hydrogen bonds and other possible non-covalent interactions. It is noted that the co-crystal itself may form solvates, including hydrates. The object (or ligand) refers to other physiologically acceptable acids, bases or non-ionic compounds.

As used herein, the term "solvate" refers to a crystal form of the compound of formula (I), the pharmaceutically acceptable salt, polymorph, co-crystal, stereoisomer, isotopic compound, metabolite or prodrug thereof, which further comprises one or more solvent molecule(s) incorporated into the crystal structure. The solvate may include a stoichiometric amount or a non-stoichiometric amount of solvent, and the solvent molecule in the solvent may exist in an ordered or non-ordered arrangement. The solvate containing a non-stoichiometric amount of solvent molecules may be obtained by the loss of at least one solvent molecule (but not all) from the solvate. In a particular embodiment, a solvate refers to a hydrate, which means the crystal of the compound further comprises water molecules, with water molecules as the solvent.

As used herein, the term "prodrug" refers to a derivative of the compound comprising a biologically reactive functional group such that the biological reactive functional group can be cleaved from the compound or react in other ways to give the compound under biological conditions (in vivo or in vitro). Usually, the prodrug is inactive, or at least has lower activity than the compound itself, so that the compound exhibits its activity until it is cleaved from the biologically reactive functional group. The biologically reactive functional group can be hydrolyzed or oxidized under biological conditions to give the compound. For instance, the prodrug may contain a biologically hydrolysable group. Examples of the biologically hydrolysable group include but are not limited to: a biologically hydrolysable phosphate, a biologically hydrolysable ester, a biologically hydrolysable amide, a biologically hydrolysable carbonic ester, a biologically hydrolysable carbamate and a biologically hydrolysable ureide. For a review of the prodrug, see, for example, J. Rautio et al., Nature Reviews Drug Discovery (2008) 7, 255-270 and Prodrugs: Challenges and Rewards (V. Stella et al. ed., Springer, 2007).

The compound of formula (I), the pharmaceutically acceptable salt, solvate, polymorph, co-crystal, stereoisomer, isotope compound, metabolite or prodrug thereof in the combination of the present invention, may contain one or more asymmetric centers ("stereoisomer"). As used herein, the term "stereoisomer" refers to all stereoisomers including enantiomers, diastereoisomers, epimers, endo-exo isomers, atropisomers, regioisomers, cis- and trans-isomers. The "stereoisomer" herein also includes "pure stereoisomer" and "enriched stereoisomer" or "racemic isomer" of the various aforementioned stereoisomers. These stereoisomers can be prepared according to an asymmetric synthesis process, or separated, purified and enriched by a chiral separation process (including but not limited to thin layer chromatography, rotating chromatography, column chromatography, gas chromatography, high pressure liquid chromatography, etc.), and can also be obtained through chiral separation by means of bonding (chemical binding etc.) or salifying (physical binding etc.) with other chiral compound(s). The term "pure stereoisomer" herein refers to a stereoisomer of the compound with the mass content of no less than 95% relative to other stereoisomers of the compound. The term "enriched stereoisomer" herein refers to a stereoisomer of the compound with the mass content of no less than 50% relative to other stereoisomers of the compound. The term "racemic isomer" herein refers to a stereoisomer of the compound with the mass content equal to that of other stereoisomers of the compound.

As used herein, D represents deuterium-enriched hydrogen, and H represents non-deuterium-enriched hydrogen. "Deuterium-enriched" compound means that abundance of deuterium at any relevant site in the compound of formula (I), the pharmaceutically acceptable salt, solvate, polymorph, co-crystal, stereoisomer, isotope compound, metabolite or prodrug thereof is greater than its natural abundance at that site (0.0156%). So, in the "deuterium-enriched" compounds, the abundance of deuterium at any of its related sites may be in the range of 0.0156% to 100%. An example of a process for obtaining deuterium-enriched compounds is to exchange hydrogen with deuterium or to synthesize the compound from deuterium-enriched starting material.

Based on the general knowledge in the art, the symbol H may be omitted in the non-deuterium-enriched site. "Non-deuterium enriched" refers to hydrogen in nature, i.e., in the form of isotopic mixture of H (hydrogen or protium), D ($^2$H or deuterium) and T ($^3$H or tritium).

The term "isotopic compound" used herein refers to the compound as shown in formula (I), the pharmaceutically acceptable salt, the solvate, the polymorph, the co-crystal, the stereoisomer, the isotopic compound, the metabolite or the prodrug thereof containing one or more atomic isotope(s) with natural or non-natural abundance. Atomic isotopes with non-natural abundance include, but are not limited to: deuterium ($^2$H or D), tritium ($^3$H or T), iodine-125 ($^{125}$I), phosphorus-32 ($^{32}$P), carbon-13 ($^{13}$C) or carbon-14 ($^{14}$C). The aforementioned isotopic compound can also be used as a therapeutic or diagnostic agent (i.e., internal developing agent) or a research tool. All the isotopic variants of the compound of the present invention, whether radioactive or not, are included in the scope of the present invention.

The term "isotope enriched" used herein refers to the compound of formula (I), the pharmaceutically acceptable salt, solvate, polymorph, co-crystal, stereoisomer, metabolite or prodrug thereof containing one or more atomic isotope(s) with non-natural abundance. The term "isotope enriched" also refers to the compound as shown in formula (I), the pharmaceutically acceptable salt, the solvate, the polymorph, the co-crystal, the stereoisomer, the isotopic compound, the metabolite or the prodrug thereof containing at least one isotopic atom with non-natural abundance.

As used herein, the term "subject" or "patient" refers to any animal to be treated or treated with the compound or the composition according to the embodiments of the present invention, preferably mammal, and most preferably human. The term "mammal" used herein includes any mammal. Examples of mammals include but not limited to cattle, horse, sheep, pig, cat, dog, mouse, rat, rabbit, guinea pig, monkey, human and the like, most preferably human. In an embodiment, the terms "treat" and "treating" refers to an improvement, prevention or reversal of a disease or condition or at least one of identifiable symptoms thereof, such as treating cancer by reducing or stabilizing the symptoms of the cancer or the condition. In another embodiment, "treat" or "treating" refers to an improvement, prevention or reversal of at least one measurable body parameter of a disease or condition which is being treated, but may not be identified in mammal. However, in another embodiment, the term "treat" or "treating" refers to slowing the progression of a disease or condition, in physical, such as stabilizing identifiable symptoms, or in physiological, such as stabilizing physical parameters, or in both. In another embodiment, the term "treat" or "treating" refers to delaying the development of a disease or symptom.

In some embodiments, the combination, pharmaceutical composition or kit is administered for a prevention purpose. As used herein, "prevent" or "preventing" refers to a reduction in a risk of obtaining a given disease or condition. In a preferred embodiment, the designated combination, pharmaceutical composition or kit is administered for a prevention purpose to a subject, such as a subject with family history or tendency of cancer or autoimmune disease.

As used herein, "therapeutically effective amount" refers to an amount of the compound or the composition (which is sought by researchers, veterinarians, physicians, or other clinicians) that can cause a biological or medical response in a tissue system, an animal or a person, which may include relieving symptoms of the disease or symptom which is being treated. In a preferred embodiment, the therapeutically effective amount is an amount which is enough to effectively treat, improve or prevent cancer, condition or undesirable angiogenesis.

The term "prophylactically effective amount" refers to an amount of the active compound or medicament (sought by researchers, veterinarians, physicians or other clinicians) that can inhibit the development of a disease in a subject. A prophylactically effective amount of the compound refers to an amount of the therapeutic agent used alone or in combination with other active compound, which can provide a therapeutic benefit for treating or preventing the disease, condition or disorder.

Each preferred conditions aforementioned can be combined randomly without departing from the common knowledge in the art thereby forming various preferred embodiments of the present invention.

Unless otherwise specified, the singular form of the term used herein, "a" or "an", also includes a plural meaning.

Unless otherwise specified, the term "or" or "and" used herein refers to "and/or".

Various publications, articles, and patents are cited or described herein. The citation or description of these references or the incorporation in their entirety or the discussion about them intends to illustrate the background of the present invention, but not to mean that the contents thereof form a part of the prior art of the present invention.

Unless defined otherwise, all technical and scientific terms used herein have the same meaning as commonly understood by an ordinary person skilled in the art to which this invention belongs. Otherwise, the meaning of certain terms used herein has the meaning set forth in this description.

In the present invention, the structures of the androgen receptor pathway modulator and the hormone compound are as follows:

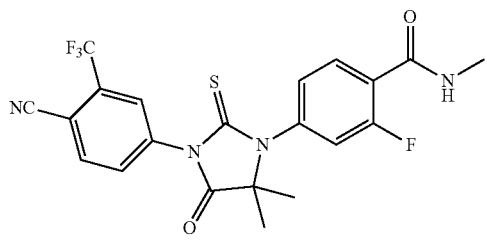
Enzalutamide

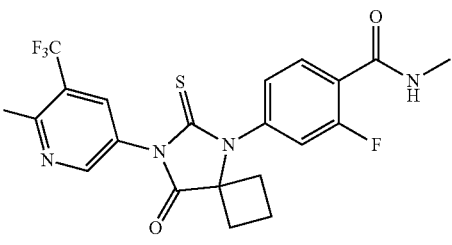
ARN-509 (Apalutamide)

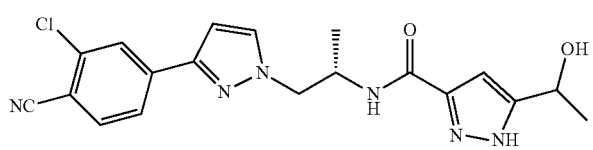
ODM-201 (BAY-1841788)

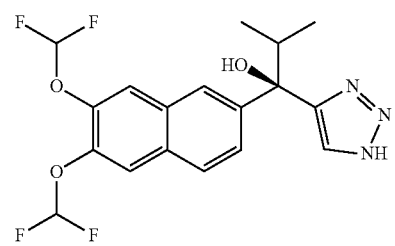
VT-464

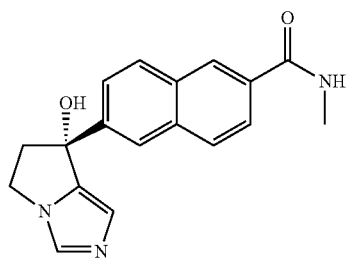
Orteronel (TAK-700)

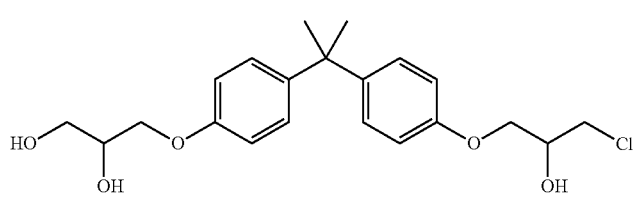
EPI-001

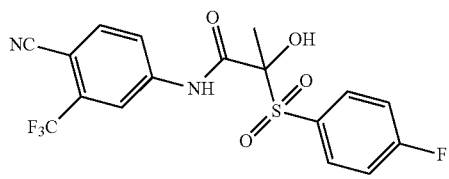
Bicalutamide

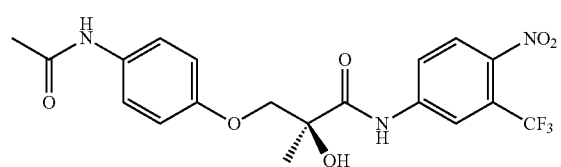
Andarine (GTx-007)

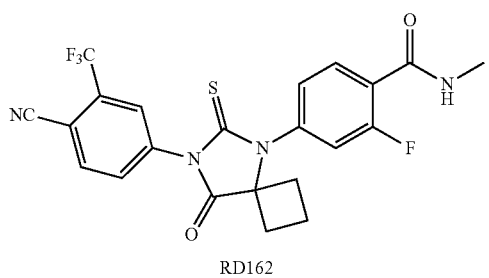
RD162

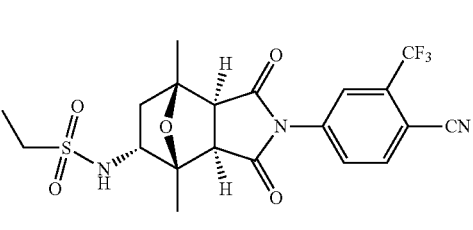
BMS-641988

-continued
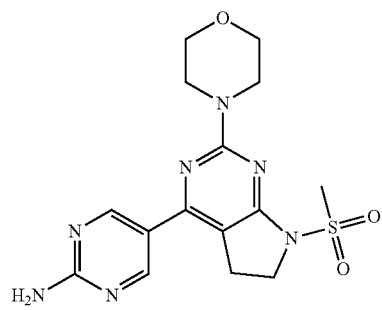
CH5137291
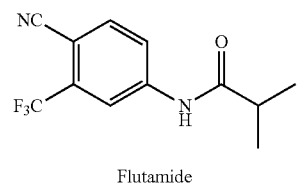
Flutamide
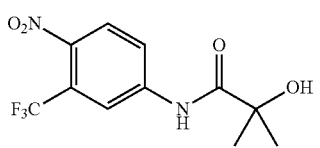
Hydroxyflutamide
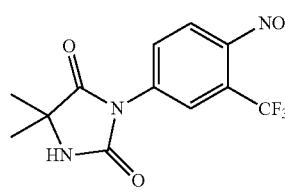
Nilutamide
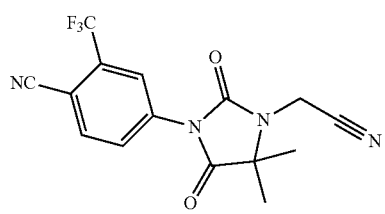
RU58642
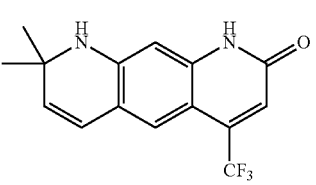
LG120907
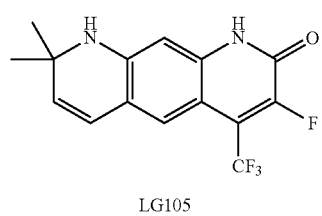
LG105
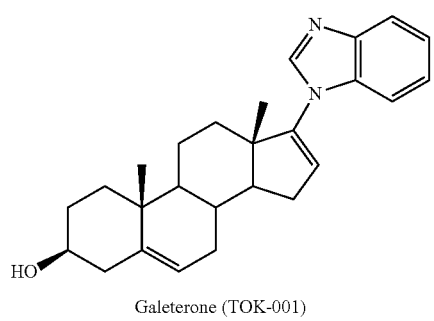
Galeterone (TOK-001)
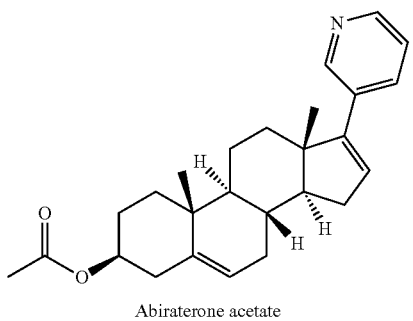
Abiraterone acetate
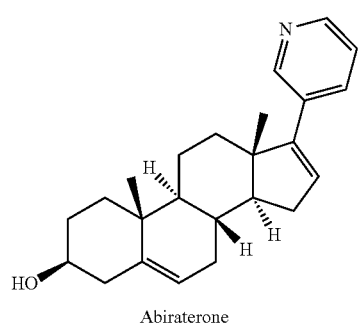
Abiraterone
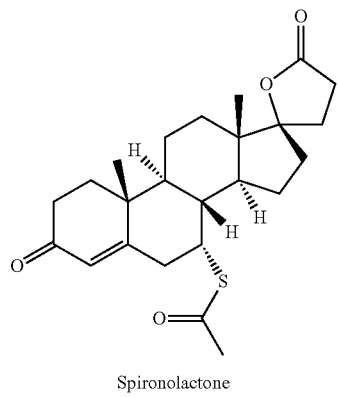
Spironolactone
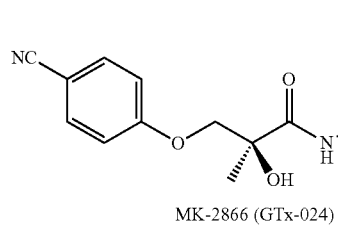
MK-2866 (GTx-024)
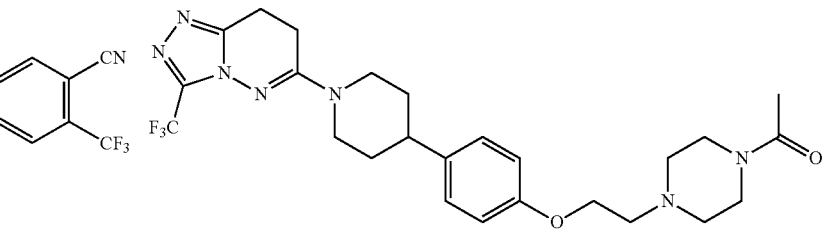
AZD3514

-continued
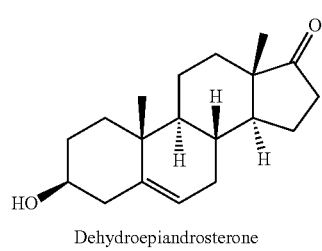
Dehydroepiandrosterone
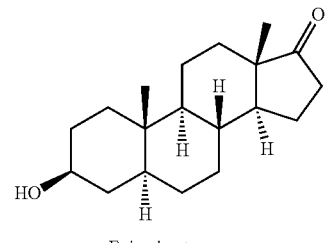
Epiandrosterone
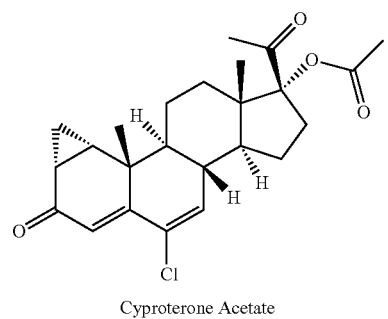
Cyproterone Acetate
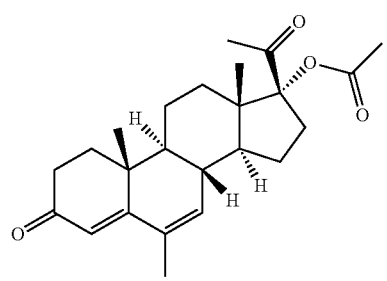
Megestrol Acetate
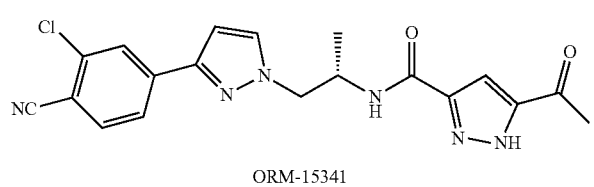
ORM-15341
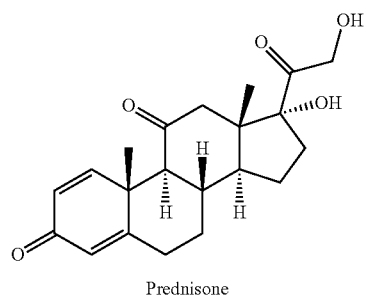
Prednisone
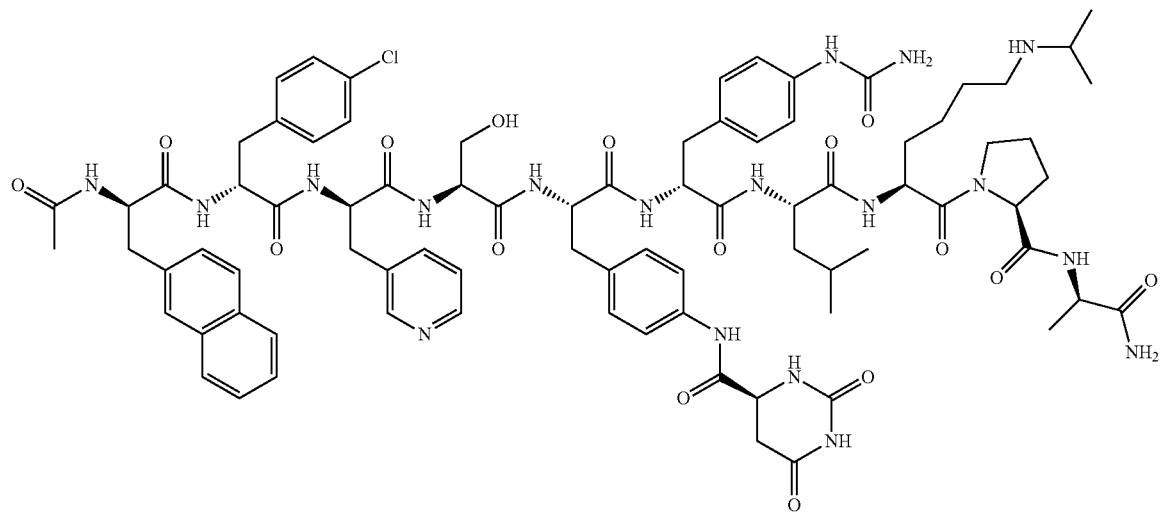
Degarelix

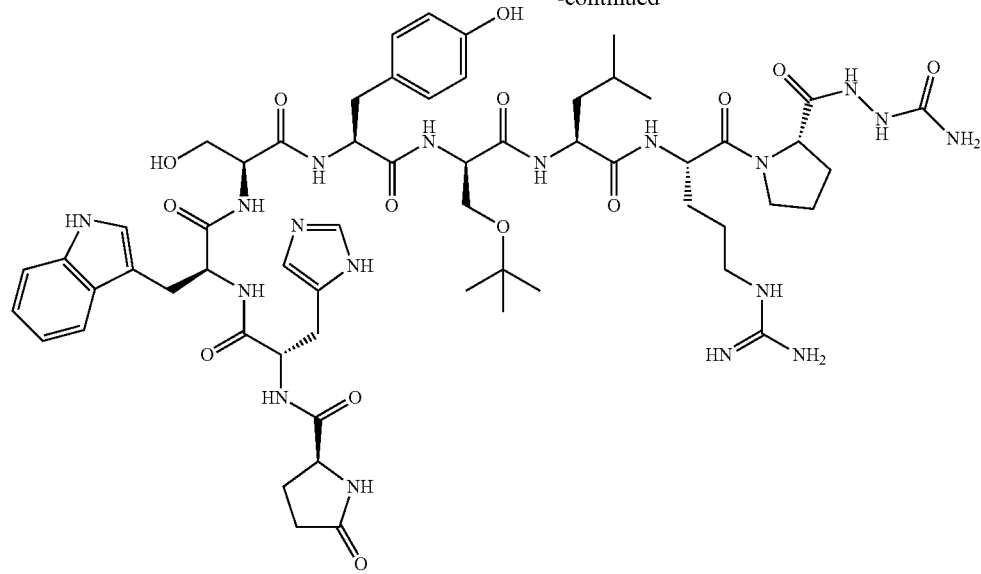

Goserelin acetate

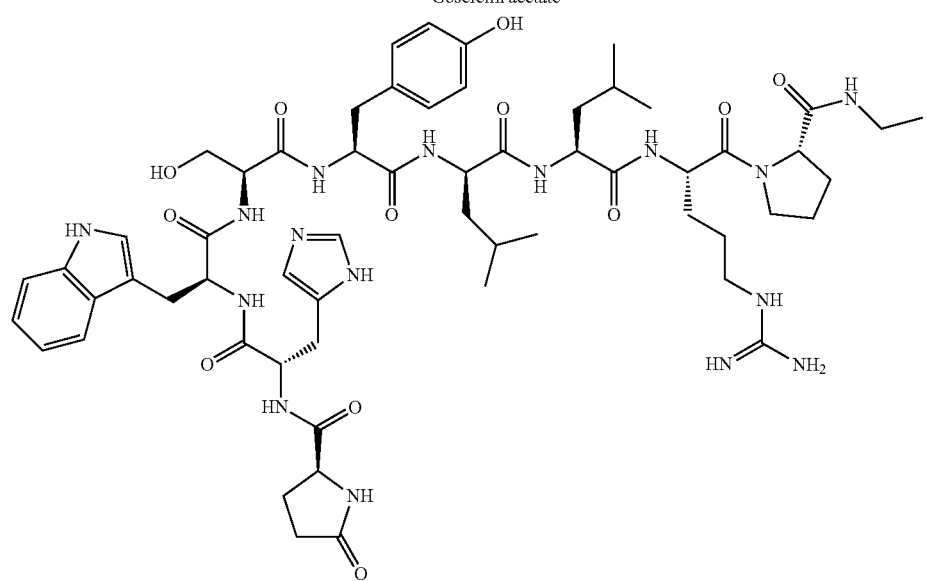

Leuprolide acetate

The reagents used in the present invention are all commercially available. The compound of formula (I) and the androgen receptor pathway modulator in the present invention may be prepared by people skilled in the art according to synthetic methods well known in the art, or readily synthesized according to the published literatures or patents, such as WO2016065980, WO9803502, WO2010056344, WO2012079022, WO2012015986, WO2011100380, WO2014116573, WO2008039489, WO2014110558, WO2014039421, WO2006124118 and so on.

The positive effect of the present invention is that the combination of the present invention can inhibit the growth of prostate cancer cells more effectively. There is a synergistic effect between each of the components in the combination.

DETAILED DESCRIPTION OF THE EMBODIMENTS

The invention will be further illustrated by the following examples, but it should not be constructed that the invention is limited to the scope of the examples. The experimental methods that are not specified in details in the following examples are those according to conventional methods and conditions, or according to the product manuals.

Effect Embodiment 1 CTG Cell Proliferation Assay

In vitro test of the inhibition effect of the compound in combination with androgen receptor pathway modulators on the prostate cancer cell proliferation.

Inhibition effect of the compounds such as B101, B102, B103, B104, B105, B106, C111 and the like, androgen receptor pathway modulators, hormone compounds, alone or in combination with each other on the prostate cancer cell proliferation were tested on Vcap cells (androgen receptor (+) prostate cancer cells) (ATCC, catalogue number CRL-2876). The specific experimental operation was as follows: $5 \times 10^3$ Vcap cells per well were inoculated into 96-well plates with transparent bottom and white wall (Corning, catalogue number CLS3903) containing the specific medium, and were cultured in a 37° C., 5% $CO_2$ incubator for 24 hours. The tested compounds and the androgen receptor pathway modulators were prepared to a 150 mM stocking solution with DMSO (Sigma, catalogue number 276855), diluted with culture medium to the desired concentrations (the final concentration of DMSO is 0.2%), and then added to each well, 2 wells/concentration, followed by being incubated in a 37° C., 5% $CO_2$ incubator for 5 days. The tested compounds were used alone or in combination with other androgen receptor pathway modulators and/or hormone compounds respectively. The combination drugs were: Enzalutamide (Selleck, catalogue number S1250), ARN-509 (Selleck, catalogue number S2840), Abiraterone acetate (Selleck, catalogue number S2246), Galeterone (Selleck, catalogue number S2803), ODM-201 (Kangpu Biopharmaceuticals, Ltd.) or Prednisone (Selleck, catalogue number S1622). The concentration setting of each drug was shown in the following tables of experimental results. After that, 100 μl of CellTiter-Glo® cell viability assay reagent (Promega, catalogue number G7570) was added to each well and mixed well on a vibrator for 10 minutes to induce cell lysis. The 96-well plate was placed at room temperature for 10 minutes, so as to stabilize its luminescence signal. A white bottom membrane was pasted on the bottom of the plate and the plate was tested using EnSpire. The data was processed by Graphpad/Prism and Calcusyn software to calculate the average cell proliferation inhibition rate or survival rate for each compound or the synergism index of the drug combination, and the specific experimental results were shown in Tables 1-12.

TABLE 1

Vcap cell proliferation inhibition rate: the combination of B105 and Enzalutamide

| | | B105 (μM) | | | | | | | | |
|---|---|---|---|---|---|---|---|---|---|---|
| | | 300.00 | 100.00 | 33.33 | 11.11 | 3.70 | 1.23 | 0.41 | 0.14 | 0.05 | 0.00 |
| Enzalutamide (μM) | 11.11 | 62.2% | 64.6% | 65.4% | 64.6% | 62.5% | 63.4% | 60.2% | 59.2% | 52.3% | 38.9% |
| | 3.70 | 65.8% | 67.7% | 67.3% | 67.8% | 67.0% | 64.5% | 63.9% | 59.8% | 53.4% | 38.2% |
| | 1.23 | 62.9% | 63.2% | 64.5% | 66.4% | 64.6% | 61.8% | 60.2% | 54.1% | 48.2% | 30.0% |
| | 0.41 | 55.4% | 51.9% | 53.0% | 52.3% | 50.5% | 49.7% | 48.1% | 45.4% | 37.1% | 29.5% |
| | 0.14 | 41.0% | 39.7% | 41.4% | 40.9% | 37.8% | 38.5% | 39.7% | 36.2% | 28.3% | 20.8% |
| | 0.05 | 33.3% | 29.5% | 34.6% | 33.8% | 32.2% | 33.5% | 33.6% | 31.9% | 25.8% | 17.7% |
| | 0.00 | 22.8% | 25.1% | 27.4% | 27.0% | 25.9% | 26.3% | 28.2% | 23.9% | 17.4% | 6.5% |

Notes of table 1: The cell proliferation inhibition rate (%) was measured after processing the Vcap cells with different concentrations of B105 and Enzalutamide alone or in combination for 5 days. The effect of drug combination was outstanding, for example, the inhibition rate on Vcap cells was 26.3% when B105 was used alone (concentration of 1.23 μM), the inhibition rate on Vcap cells was 30% when Enzalutamide was used alone (concentration of 1.23 μM), and the inhibition rate on Vcap cells was 61.8% when the two were combined (1.23 μM B105 and 1.23 μM Enzalutamide).

TABLE 2

Synergism index of the combination of B105 and Enzalutamide (carrying out synergism analysis on the experimental data of the drug combination in table 1)

|  |  | B105 (μM) | | | | | | | | |
|---|---|---|---|---|---|---|---|---|---|---|
|  |  | 300.00 | 100.00 | 33.33 | 11.11 | 3.70 | 1.23 | 0.41 | 0.14 | 0.05 |
| Enzalutamide (μM) | 11.11 | 0.018 | 0.011 | 0.01 | 0.011 | 0.017 | 0.014 | 0.027 | 0.033 | 0.126 |
|  | 3.70 | 0.003 | 0.002 | 0.002 | 0.002 | 0.002 | 0.004 | 0.004 | 0.01 | 0.034 |
|  | 1.23 | 0.002 | 0.002 | 0.001 | 0.001 | 0.001 | 0.002 | 0.003 | 0.01 | 0.03 |
|  | 0.41 | 0.003 | 0.005 | 0.004 | 0.005 | 0.007 | 0.008 | 0.01 | 0.017 | 0.088 |
|  | 0.14 | 0.014 | 0.018 | 0.013 | 0.014 | 0.026 | 0.023 | 0.018 | 0.036 | 0.201 |
|  | 0.05 | 0.024 | 0.055 | 0.018 | 0.021 | 0.03 | 0.023 | 0.022 | 0.032 | 0.132 |

Notes of table 2: The synergism analysis was carried out on the experimental data of the drug combination of B105 and Enzalutamide in table 1 to give the data in Table 2 which showed a strong synergism when the two drugs are used in combination.

Notes of the synergism index of drug combination (the same below): <0.1: very strong synergism; 0.1-0.3: strong synergism; 0.3-0.7: synergism; 0.7-0.85: mild synergism; 0.85-0.90: slight synergism; 0.90-1.10: approximately additive action; 1.10-1.20: slight antagonism; 1.20-1.45: mild antagonism; 1.45-3.3: antagonism; 3.3-10: strong antagonism; >10: very strong antagonism.

TABLE 3

Vcap cell proliferation inhibition rate: the combination of C111 and Enzalutamide

|  |  | C111 (μM) | | | | | | | | | |
|---|---|---|---|---|---|---|---|---|---|---|---|
|  |  | 300.00 | 100.00 | 33.33 | 11.11 | 3.70 | 1.23 | 0.41 | 0.14 | 0.05 | 0.00 |
| Enzalutamide (μM) | 11.11 | 68.8% | 64.2% | 62.8% | 58.3% | 57.0% | 55.7% | 54.0% | 53.5% | 53.3% | 36.6% |
|  | 3.70 | 70.7% | 64.4% | 58.5% | 57.5% | 55.2% | 52.9% | 54.3% | 51.6% | 51.9% | 37.0% |
|  | 1.23 | 70.1% | 64.3% | 59.5% | 57.0% | 52.2% | 54.7% | 51.1% | 52.5% | 49.8% | 36.8% |
|  | 0.41 | 61.6% | 53.1% | 48.3% | 47.5% | 45.5% | 42.1% | 44.9% | 40.7% | 41.1% | 33.9% |
|  | 0.14 | 54.0% | 43.3% | 44.9% | 44.4% | 36.4% | 42.0% | 40.9% | 41.4% | 38.3% | 27.7% |
|  | 0.05 | 44.4% | 38.4% | 37.9% | 33.8% | 34.6% | 34.7% | 30.2% | 31.7% | 29.8% | 17.0% |
|  | 0.00 | 33.9% | 31.6% | 29.1% | 28.8% | 25.4% | 23.4% | 24.9% | 20.9% | 19.6% | 6.9% |

Notes of table 3: The cell proliferation inhibition rate (%) was measured after processing the Vcap cells with different concentrations of C111 and Enzalutamide alone or in combination for 5 days. The effect of drug combination was outstanding, for example, the inhibition rate on Vcap cells was 23.4% when C111 was used alone (concentration of 1.23 μM), the inhibition rate on Vcap cells was 36.8% when Enzalutamide was used alone (concentration of 1.23 μM), and the inhibition rate on Vcap cells was 54.7% when the two were combined (1.23 μM C111 and 1.23 μM Enzalutamide).

TABLE 4

Synergism index of the combination of C111 and Enzalutamide (carrying out synergism analysis on the experimental data of the drug combination in table 3)

|  |  | C111 (μM) | | | | | | | | |
|---|---|---|---|---|---|---|---|---|---|---|
|  |  | 300.00 | 100.00 | 33.33 | 11.11 | 3.70 | 1.23 | 0.41 | 0.14 | 0.05 |
| Enzalutamide (μM) | 11.11 | 0.001 | 0.005 | 0.007 | 0.02 | 0.028 | 0.038 | 0.056 | 0.063 | 0.066 |
|  | 3.70 | 0 | 0.002 | 0.006 | 0.008 | 0.014 | 0.024 | 0.018 | 0.033 | 0.031 |
|  | 1.23 | 0 | 0.001 | 0.002 | 0.003 | 0.009 | 0.005 | 0.012 | 0.009 | 0.017 |
|  | 0.41 | 0 | 0.003 | 0.008 | 0.009 | 0.015 | 0.034 | 0.017 | 0.047 | 0.043 |
|  | 0.14 | 0.001 | 0.011 | 0.006 | 0.007 | 0.049 | 0.012 | 0.015 | 0.014 | 0.029 |
|  | 0.05 | 0.006 | 0.036 | 0.023 | 0.065 | 0.033 | 0.027 | 0.092 | 0.057 | 0.094 |

Notes of table 4: The synergism analysis was carried out on the experimental data of the drug combination of C111 and Enzalutamide in table 3 to give the data in Table 4 which showed a strong synergism when the two drugs are used in combination.

TABLE 5

Survival rate of Vcap cells: tested compound alone, tested compound in combination with Enzalutamide or ARN-509

| tested compound | tested compound alone | | | in combination with 1 μM Enzalutamide | | | in combination with 1 μM ARN-509 | | |
| --- | --- | --- | --- | --- | --- | --- | --- | --- | --- |
| | 10 μM | 1 μM | 0.1 μM | 10 μM | 1 μM | 0.1 μM | 10 μM | 1 μM | 0.1 μM |
| Enzalutamide | 52.3% | 54.0% | 74.5% | | | | | | |
| ARN-509 | 48.9% | 52.2% | 81.8% | | | | | | |
| B101 | 64.7% | 65.4% | 77.7% | 24.4% | 25.2% | 30.6% | 24.5% | 24.3% | 29.3% |
| B105 | 72.7% | 72.5% | 83.3% | 27.5% | 27.5% | 31.6% | 27.0% | 28.0% | 30.6% |
| C111 | 77.0% | 81.0% | 81.5% | 36.6% | 35.8% | 36.3% | 37.3% | 35.6% | 37.0% |

Notes of table 5: The effect of the drug combination was outstanding, for example, the cell survival rates were 65.4%, 72.5%, 81.0%, 54.0% and 52.2% when B101, B105, C111, enzalutamide and ARN-509 were used alone respectively at 1.0 μM. The cell survival rates were 25.2%, 27.5% and 35.8% when 1.0 μM B101, B105 or C111 was used in combination with 1.0 μM enzalutamide respectively. The cell survival rates were 24.3%, 28.0% and 35.6% when 1.0 μM B101, B105 or C111 was used in combination with 1.0 μM ARN-509 respectively.

TABLE 6

Survival rate of Vcap cells: tested compound alone, tested compound in combination with Galeterone or Abiraterone acetate

| tested compound | tested compound alone | | | in combination with in 1 μM Galeterone | | | combination with 1 μM Abiraterone acetate | | |
| --- | --- | --- | --- | --- | --- | --- | --- | --- | --- |
| | 10 μM | 1 μM | 0.1 μM | 10 μM | 1 μM | 0.1 μM | 10 μM | 1 μM | 0.1 μM |
| B101 | 64.7% | 65.4% | 77.7% | 32.5% | 34.4% | 38.6% | 52.9% | 56.6% | 61.8% |
| B105 | 72.7% | 72.5% | 83.3% | 36.3% | 36.7% | 40.9% | 58.0% | 57.1% | 65.0% |
| C111 | 77.0% | 81.0% | 81.5% | 47.8% | 47.0% | 46.6% | 66.1% | 68.5% | 65.5% |
| Galeterone | 19.3% | 62.8% | 95.9% | | | | | | |
| Abiraterone acetate | 31.4% | 91.7% | 106.3% | | | | | | |

Notes of table 6: The effect of the drug combination was outstanding, for example, the cell survival rates were 65.4%, 72.5%, 81.0%, 62.8% and 91.7% when B101, B105, C111, Galeterone and Abiraterone acetate were used alone respectively at 1.0 μM. The cell survival rates were 34.4%, 36.7% and 47.0% when 1.0 μM B101, B105 or C111 was used in combination with 1.0 μM Galeterone respectively. The cell survival rates were 56.6%, 57.1% and 68.5% when 1.0 μM B101, B105 or C111 was used in combination with 1.0 μM Abiraterone acetate respectively.

TABLE 7

Survival rate of Vcap cells: tested compound alone, tested compound in combination with ODM-201

| tested compound | tested compound alone | | | in combination with 1 μM ODM-201 | | |
|---|---|---|---|---|---|---|
| | 10 μM | 1 μM | 0.1 μM | 10 μM | 1 μM | 0.1 μM |
| ODM-201 | 75.4% | 69.0% | 90.7% | | | |
| B101 | 65.8% | 71.1% | 81.7% | 32.5% | 37.1% | 43.8% |
| B105 | 65.5% | 69.7% | 77.9% | 32.2% | 36.6% | 43.3% |
| C111 | 63.3% | 72.0% | 76.3% | 37.2% | 43.1% | 45.9% |

Notes of table 7: The effect of the drugs combination was outstanding, for example, the cell survival rates were 69.0%, 71.1%, 69.7% and 72.0% respectively when ODM-201, B101, B105 and C111 were used alone at 1.0 μM. The cell survival rates were 37.1%, 36.6% and 43.1% when 1.0 μM B101, B105 or C111 was used in combination with 1.0 μM ODM-201 respectively.

TABLE 8

Survival rate of Vcap cells: B105 in combination with Enzalutamide, ARN-509, Prednisone, Galeterone, or Abiraterone acetate respectively

| drug combination | B105 1 μM | Enzalutamide 10 μM | Enzalutamide 1 μM | Enzalutamide 0.1 μM | ARN-509 10 μM | ARN-509 1 μM | ARN-509 0.1 μM | Prednisone 1 μM | Galeterone 1 μM | Abiraterone acetate 1 μM | Cell survival rate |
|---|---|---|---|---|---|---|---|---|---|---|---|
| 2-drug combination | | v | | | | | | v | | | 51.8% |
| | | | v | | | | | v | | | 54.5% |
| | | | | v | | | | v | | | 84.6% |
| | | v | | | | | | | v | | 50.9% |
| | | | v | | | | | | v | | 52.4% |
| | | | | v | | | | | v | | 59.5% |
| | | v | | | | | | | | v | 51.7% |
| | | | v | | | | | | | v | 50.7% |
| | | | | v | | | | | | v | 69.7% |
| | | | | | v | | | v | | | 47.4% |
| | | | | | | v | | v | | | 54.3% |
| | | | | | | | v | v | | | 79.6% |
| | | | | | v | | | | v | | 46.5% |
| | | | | | | v | | | v | | 50.8% |
| | | | | | | | v | | v | | 61.0% |
| | | | | | v | | | | | v | 46.6% |
| | | | | | | v | | | | v | 50.5% |
| | | | | | | | v | | | v | 68.9% |
| 3-drug combination | | v | | | | | | v | v | | 50.4% |
| | | | v | | | | | v | v | | 49.5% |
| | | | | v | | | | v | v | | 54.3% |
| | | v | | | | | | v | | v | 46.3% |
| | | | v | | | | | v | | v | 45.9% |
| | | | | v | | | | v | | v | 68.5% |
| | | | | | v | | | v | v | | 46.2% |
| | | | | | | v | | v | v | | 47.5% |
| | | | | | | | v | v | v | | 58.3% |
| | | | | | v | | | v | | v | 44.1% |
| | | | | | | v | | v | | v | 46.1% |
| | | | | | | | v | v | | v | 69.3% |
| | v | | | | | | | v | v | | 35.6% |
| | v | | | | | | | v | | v | 53.1% |
| | v | v | | | | | | | v | | 23.9% |
| | v | v | | | | | | | | v | 23.0% |
| | v | v | | | | | | v | | | 24.5% |
| | v | | v | | | | | | v | | 21.7% |
| | v | | v | | | | | | | v | 22.8% |
| | v | | v | | | | | v | | | 25.5% |
| | v | | | v | | | | | v | | 22.8% |
| | v | | | v | | | | | | v | 22.0% |
| | v | | | v | | | | v | | | 22.6% |
| | v | | | | v | | | | v | | 21.6% |
| | v | | | | v | | | | | v | 22.7% |
| | v | | | | v | | | v | | | 23.6% |
| | v | | | | | v | | | v | | 27.6% |
| | v | | | | | v | | | | v | 37.0% |
| | v | | | | | v | | v | | | 46.4% |

TABLE 8-continued

Survival rate of Vcap cells: B105 in combination with Enzalutamide, ARN-509, Prednisone, Galeterone, or Abiraterone acetate respectively

| drug combination | B105 1 μM | Enzalutamide 10 μM | Enzalutamide 1 μM | Enzalutamide 0.1 μM | ARN-509 10 μM | ARN-509 1 μM | ARN-509 0.1 μM | Prednisone 1 μM | Galeterone 1 μM | Abiraterone acetate 1 μM | Cell survival rate |
|---|---|---|---|---|---|---|---|---|---|---|---|
|  | v |  |  |  |  |  | v |  | v |  | 27.9% |
|  | v |  |  |  |  |  | v |  |  | v | 32.5% |
|  | v |  |  |  |  |  | v | v |  |  | 39.8% |
| 4-drug combination | v | v |  |  |  |  |  | v | v |  | 28.8% |
|  | v | v |  |  |  |  |  | v |  | v | 27.3% |
|  | v |  | v |  |  |  |  | v | v |  | 23.8% |
|  | v |  | v |  |  |  |  | v |  | v | 22.2% |
|  | v |  |  | v |  |  |  | v | v |  | 25.5% |
|  | v |  |  | v |  |  |  | v |  | v | 25.9% |
|  | v |  |  |  | v |  |  | v | v |  | 25.5% |
|  | v |  |  |  | v |  |  | v |  | v | 23.4% |
|  | v |  |  |  |  | v |  | v | v |  | 28.8% |
|  | v |  |  |  |  | v |  | v |  | v | 38.8% |
|  | v |  |  |  |  |  | v | v | v |  | 27.1% |
|  | v |  |  |  |  |  | v | v |  | v | 32.7% |

"V" refers to the components contained in the combination. The blank indicates the component was not contained. The same below.

Notes of table 8: The effect of the drug combination was outstanding, for example, the cell survival rate was 50.7% when 1.0 μM Enzalutamide was used in combination with 1.0 μM Abiraterone acetate. The cell survival rate decreased to 22.0% when 1.0 μM Enzalutamide was used in combination with 1.0 μM Abiraterone acetate and 1.0 μM B105. The cell survival rate was 45.9% when 1.0 μM Enzalutamide was used in combination with 1.0 μM Prednisone and 1.0 μM Abiraterone acetate. The cell survival rate decreased to 25.9% when 1.0 μM Enzalutamide was used in combination with 1.0 μM Prednisone and 1.0 μM Abiraterone acetate and 1.0 μM B105.

TABLE 9

Survival rate of Vcap cells: C111 in combination with Enzalutamide, ARN-509, Prednisone, Galeterone, or Abiraterone acetate respectively

| Drug combination | C111 1 μM | Enzalutamide 10 μM | Enzalutamide 1 μM | Enzalutamide 0.1 μM | ARN-509 10 μM | ARN-509 1 μM | ARN-509 0.1 μM | Prednisone 1 μM | Galeterone 1 μM | Abiraterone acetate 1 μM | Cell survival rate |
|---|---|---|---|---|---|---|---|---|---|---|---|
| 3-drug combination |  | v |  |  |  |  |  |  | v | v | 51.4% |
|  |  |  | v |  |  |  |  |  | v | v | 52.8% |
|  |  |  |  | v |  |  |  |  | v | v | 64.1% |
|  |  | v |  |  |  |  |  |  | v | v | 50.2% |
|  |  |  | v |  |  |  |  |  | v | v | 49.8% |
|  |  |  |  | v |  |  |  |  | v | v | 68.1% |
|  |  |  |  |  | v |  |  |  | v | v | 48.7% |
|  |  |  |  |  |  | v |  |  | v | v | 54.0% |
|  |  |  |  |  |  |  | v |  | v | v | 57.4% |
|  |  |  |  |  | v |  |  |  | v | v | 48.4% |
|  |  |  |  |  |  | v |  |  | v | v | 55.5% |
|  |  |  |  |  |  |  | v |  | v | v | 66.5% |
|  | v |  |  |  |  |  |  |  | v | v | 41.9% |
|  | v |  |  |  |  |  |  |  | v | v | 64.9% |
|  | v | v |  |  |  |  |  |  |  | v | 39.0% |
|  | v | v |  |  |  |  |  |  |  | v | 38.4% |
|  | v | v |  |  |  |  |  |  | v |  | 38.8% |
|  | v |  |  |  | v |  |  |  |  | v | 34.3% |
|  | v |  |  |  | v |  |  |  |  | v | 34.1% |
|  | v |  |  |  | v |  |  |  | v |  | 35.4% |
|  | v |  | v |  |  |  |  |  |  | v | 37.2% |
|  | v |  | v |  |  |  |  |  |  | v | 40.1% |
|  | v |  | v |  |  |  |  |  | v |  | 41.6% |
|  | v |  |  |  |  | v |  |  |  | v | 39.5% |
|  | v |  |  |  |  | v |  |  |  | v | 38.8% |
|  | v |  |  |  |  | v |  |  | v |  | 38.8% |
|  | v |  |  | v |  |  |  |  |  | v | 44.4% |
|  | v |  |  | v |  |  |  |  |  | v | 49.6% |
|  | v |  |  | v |  |  |  |  | v |  | 56.7% |
|  | v |  |  |  |  |  | v |  |  | v | 42.6% |
|  | v |  |  |  |  |  | v |  |  | v | 47.7% |
|  | v |  |  |  |  |  | v |  | v |  | 60.0% |

TABLE 9-continued

Survival rate of Vcap cells: C111 in combination with Enzalutamide, ARN-509, Prednisone, Galeterone, or Abiraterone acetate respectively

| Drug combination | C111 1 μM | C111 10 μM | Enzalutamide 1 μM | Enzalutamide 0.1 μM | ARN-509 10 μM | ARN-509 1 μM | ARN-509 0.1 μM | Prednisone 1 μM | Galeterone 1 μM | Abiraterone acetate 1 μM | Cell survival rate |
|---|---|---|---|---|---|---|---|---|---|---|---|
| 4-drug combination | v | v |   |   |   |   | v | v |   |   | 36.3% |
|   | v | v |   |   |   |   |   | v |   | v | 38.1% |
|   | v |   |   |   | v |   |   | v | v |   | 34.5% |
|   | v |   |   |   | v |   |   | v |   | v | 33.2% |
|   | v |   | v |   |   |   |   | v | v |   | 36.4% |
|   | v |   | v |   |   |   |   | v |   | v | 35.3% |
|   | v |   |   |   |   | v |   | v | v |   | 34.9% |
|   | v |   |   |   |   | v |   | v |   | v | 33.2% |
|   | v |   |   | v |   |   |   | v | v |   | 35.8% |
|   | v |   |   | v |   |   |   | v |   | v | 40.8% |
|   | v |   |   |   |   |   | v | v | v |   | 34.1% |
|   | v |   |   |   |   |   | v | v |   | v | 41.3% |

Notes of table 9: the effect of the drug combination was outstanding, for example, the cell survival rate was 50.7% (in table 8) when 1.0 μM Enzalutamide was used in combination with 1.0 μM Abiraterone acetate. The cell survival rate decreased to 40.1% when 1.0 μM Enzalutamide was used in combination with 1.0 μM Abiraterone acetate and 1.0 μM C111. The cell survival rate was 49.8% when 1.0 μM Enzalutamide was used in combination with 1.0 μM Prednisone and 1.0 μM Abiraterone acetate. The cell survival rate decreased to 35.3% when 1.0 μM Enzalutamide was used in combination with 1.0 μM Prednisone, 1.0 μM Abiraterone acetate and 1.0 μM C111.

TABLE 10

Survival rate of Vcap cells: B101 in combination with Enzalutamide, ARN-509, Prednisone, Galeterone, or Abiraterone acetate respectively

| Drug combination | B101 1 μM | Enzalutamide 10 μM | Enzalutamide 1 μM | Enzalutamide 0.1 μM | ARN-509 10 μM | ARN-509 1 μM | ARN-509 0.1 μM | Prednisone 1 μM | Galeterone 1 μM | Abiraterone acetate 1 μM | Cell survival rate |
|---|---|---|---|---|---|---|---|---|---|---|---|
| 3-drug combination |   | v |   |   |   |   |   | v | v |   | 56.1% |
|   |   |   | v |   |   |   |   | v | v |   | 54.1% |
|   |   |   |   | v |   |   |   | v | v |   | 60.1% |
|   |   | v |   |   |   |   |   | v |   | v | 50.2% |
|   |   |   | v |   |   |   |   | v |   | v | 51.3% |
|   |   |   |   | v |   |   |   | v |   | v | 69.1% |
|   |   |   |   |   | v |   |   | v | v |   | 49.8% |
|   |   |   |   |   |   | v |   | v | v |   | 51.8% |
|   |   |   |   |   |   |   | v | v | v |   | 65.1% |
|   |   |   |   |   | v |   |   | v |   | v | 47.6% |
|   |   |   |   |   |   | v |   | v |   | v | 48.2% |
|   |   |   |   |   |   |   | v | v |   | v | 71.8% |
|   | v |   |   |   |   |   |   | v | v |   | 37.5% |
|   | v |   |   |   |   |   |   | v |   | v | 57.6% |
|   | v | v |   |   |   |   |   |   | v |   | 29.0% |
|   | v | v |   |   |   |   |   |   |   | v | 26.2% |
|   | v |   | v |   |   |   |   |   | v |   | 27.5% |
|   | v |   | v |   |   |   |   |   |   | v | 24.3% |
|   | v |   |   | v |   |   |   |   | v |   | 25.6% |
|   | v |   |   | v |   |   |   |   |   | v | 26.6% |
|   | v |   |   |   | v |   |   |   | v |   | 26.6% |
|   | v |   |   |   | v |   |   |   |   | v | 26.7% |
|   | v |   |   |   |   | v |   |   | v |   | 27.0% |
|   | v |   |   |   |   | v |   |   |   | v | 25.8% |
|   | v |   |   |   |   |   | v |   | v |   | 25.4% |
|   | v |   |   |   |   |   | v |   |   | v | 24.9% |
|   | v |   |   |   | v |   |   | v |   |   | 30.5% |
|   | v |   |   |   |   | v |   | v |   |   | 40.1% |
|   | v |   |   |   |   |   | v | v |   |   | 48.6% |
|   | v | v |   |   |   |   |   | v |   |   | 32.3% |
|   | v |   | v |   |   |   |   | v |   |   | 35.1% |
|   | v |   |   | v |   |   |   | v |   |   | 45.3% |
| 4-drug combination | v | v |   |   |   |   |   | v | v |   | 28.3% |
|   | v | v |   |   |   |   |   | v |   | v | 29.3% |
|   | v |   | v |   |   |   |   | v | v |   | 22.5% |
|   | v |   | v |   |   |   |   | v |   | v | 21.7% |
|   | v |   |   | v |   |   |   | v | v |   | 27.4% |
|   | v |   |   | v |   |   |   | v |   | v | 27.2% |

TABLE 10-continued

Survival rate of Vcap cells: B101 in combination with Enzalutamide, ARN-509, Prednisone, Galeterone, or Abiraterone acetate respectively

| Drug combination | B101 1 μM | Enzalutamide 10 μM | Enzalutamide 1 μM | Enzalutamide 0.1 μM | ARN-509 10 μM | ARN-509 1 μM | ARN-509 0.1 μM | Prednisone 1 μM | Gale-terone 1 μM | Abiraterone acetate 1 μM | Cell survival rate |
|---|---|---|---|---|---|---|---|---|---|---|---|
| | v | | | | | v | | v | v | | 25.0% |
| | v | | | | | v | | v | | v | 24.6% |
| | v | | v | | | | | v | v | | 26.2% |
| | v | | v | | | | | v | | v | 34.9% |
| | v | | | | | | v | v | v | | 28.7% |
| | v | | | | | | v | v | | v | 33.3% |

Notes of table 10: the effect of the drug combination was outstanding, for example, the cell survival rate was 50.7% (in table 8) when 1.0 μM Enzalutamide was used in combination with 1.0 μM Abiraterone acetate. The cell survival rate decreased to 26.7% when 1.0 μM Enzalutamide was used in combination with 1.0 μM Abiraterone acetate and 1.0 μM B101. The cell survival rate was 51.3% when 1.0 μM Enzalutamide was used in combination with 1.0 μM Prednisone and 1.0 μM Abiraterone acetate. The cell survival rate decreased to 27.2% when 1.0 μM Enzalutamide was used in combination with 1.0 μM Prednisone, 1.0 μM Abiraterone acetate and 1.0 μM B101.

TABLE 11

Survival rate of Vcap cells: tested compound alone, tested compound in combination with B101 or B105

| tested compound Concentration of the tested compound | tested compound alone | | | in combination with 1 μM B101 | | | in combination with 1 μM B105 | | |
|---|---|---|---|---|---|---|---|---|---|
| | 10 μM | 1 μM | 0.1 μM | 10 μM | 1 μM | 0.1 μM | 10 μM | 1 μM | 0.1 μM |
| B101 | 73.3% | 77.9% | 83.3% | — | — | — | — | — | — |
| B105 | 80.0% | 79.1% | 81.5% | — | — | — | — | — | — |
| Prednisone | 99.4% | 99.7% | 99.1% | 75.3% | 76.9% | 84.0% | 79.7% | 80.6% | 87.5% |
| bicalutamide | 92.0% | 94.0% | 99.2% | 64.0% | 66.5% | 70.5% | 63.4% | 67.3% | 75.9% |
| MK-2866 | 69.4% | 77.4% | 76.5% | 52.7% | 63.6% | 61.4% | 52.5% | 59.7% | 62.6% |
| ARN-509 | 61.9% | 70.4% | 95.9% | 38.4% | 39.2% | 42.7% | 38.0% | 38.6% | 45.3% |
| Andarine | 69.4% | 82.7% | 85.6% | 53.8% | 65.5% | 69.8% | 53.5% | 64.6% | 71.1% |
| Flutamide | 73.1% | 96.7% | 105.4% | 42.8% | 65.1% | 80.4% | 43.8% | 64.6% | 76.5% |
| Dehydroepiandrosterone | 100.4% | 102.4% | 101.2% | 75.4% | 84.5% | 85.6% | 72.9% | 78.6% | 84.2% |
| Epiandrosterone | 90.4% | 82.0% | 87.3% | 79.8% | 71.1% | 71.0% | 77.4% | 64.6% | 71.5% |
| Cyproterone Acetate | 83.5% | 96.0% | 97.2% | 78.9% | 85.0% | 85.0% | 79.4% | 84.0% | 82.1% |
| Megestrol Acetate | 88.9% | 102.9% | 99.7% | 75.2% | 83.1% | 85.2% | 76.6% | 83.3% | 82.1% |
| Spironolactone | 72.5% | 91.3% | 100.2% | 65.9% | 77.3% | 85.3% | 64.5% | 79.6% | 87.2% |
| Abiraterone acetate | 60.5% | 97.0% | 96.1% | 66.7% | 70.5% | 72.2% | 69.2% | 70.7% | 77.3% |

TABLE 12

Survival rate of Vcap cells: tested compound alone, tested compound in combination with Enzalutamide or ARN-509

| tested compound Concentration of the tested compound | tested compound alone | | | in combination with 1 μM Enzalutamide | | | in combination with 1 μM ARN-509 | | |
|---|---|---|---|---|---|---|---|---|---|
| | 10 μM | 1 μM | 0.1 μM | 10 μM | 1 μM | 0.1 μM | 10 μM | 1 μM | 0.1 μM |
| B102 | 78.4% | 80.9% | 84.7% | 40.1% | 41.1% | 46.3% | 38.3% | 40.2% | 47.2% |
| B103 | 85.5% | 84.1% | 86.3% | 42.9% | 42.7% | 50.2% | 38.3% | 41.7% | 48.8% |
| B104 | 74.0% | 77.4% | 84.4% | 38.8% | 41.2% | 47.1% | 37.8% | 40.5% | 45.7% |
| B106 | 74.1% | 79.0% | 86.8% | 38.2% | 40.5% | 50.6% | 39.9% | 41.1% | 50.6% |
| Enzalutamide | 58.4% | 65.7% | 85.9% | — | — | — | — | — | — |
| ARN-509 | 61.9% | 70.4% | 95.9% | — | — | — | — | — | — |

Notes of table 12: The effect of the drugs combination was outstanding, for example, the cell survival rates were 80.9%, 84.1%, 77.4%, 79%, 65.7% and 70.4% when B102, B103, B104, B106, Enzalutamide and ARN-509 were used alone respectively. The cell survival rates were 41.1%, 42.7%, 41.2% and 40.5% when 1.0 µM B102, B103, B104 or B106 was used in combination with 1.0 µM Enzalutamide respectively. The cell survival rates were respectively 40.2%, 41.7%, 40.5%, 41.1%, when 1.0 µM B102, B103, B104 or B106 was used in combination with 1.0 µM ARN-509 respectively.

Effect Embodiment 2 PSA Inhibition Rate Experiment

The purpose of this experiment was to test the change of the secretion level of PSA (Prostate antigen) in the supernatant of VCap cells processed by the tested compounds in combination with Enzalutamide for 5 days.

VCap cells were processed by 0.5 µM Enzalutamide alone, and by different concentrations of 2 tested compounds in combination with 0.5 µM Enzalutamide for 5 days respectively, then the PSA level of each treatment group was tested by electrochemiluminescence immunoassay.

Experimental Materials and Methods
1. Cell Line

| Type of tumor | Name of cell | Medium | Processing time (days) |
|---|---|---|---|
| prostate cancer | VCap | DMEM + 10% FBS | 5 |

The cell culture conditions were: 37° C., 5% $CO_2$ and 95% humidity.

2. Reagents
1) DMEM medium (Thermo scientific, product number: SH30243.01)
2) FBS (Fetal Bovine Serum) (Gibco, product number: 10099-141)
3) 0.25% trypsin-EDTA (Gibco, product number: 25200-072)
4) DMSO (Sigma, product number: D2650)
5) Prostate specific antigen reagent (Roche, product number: 04641655190) (provided by Taicang First People's Hospital)

3. Equipments
1) Carbon dioxide incubator: SANYO Electric Co., Ltd. (Japan). (Equipment ID: TAINC0490)
2) Microscope: Chongguang XDS-1B, Chongqing Guangdian Corp. (Chongqing, P.R.China). (Equipment ID: TAMIC0130)
3) Refrigerator: Haier Z16TXZ (China). (Equipment ID: TAREF0490)
4) Electronic Balance: Mettlertoledo AL104. (Shanghai, China). (Equipment ID: TBB AL0560)
5) Automatic Electrochemical Immunoassay Analyzer: Roche Cobas e601 (Taicang First People's Hospital)

4. Secretion inhibition rate of the tested compounds on VCap cell PSA

Cell Inoculation

Cells were collected in exponential growth phase for viable cell count. The cell suspension was adjusted to $4.17 \times 10E4/ml$ with the medium mentioned above. 120 µl of cell suspension was added to each well of a 96-well cell culture plateat, a final concentration of cells was 5000 cells/well. The cells were incubated overnight in a 37° C., 5% $CO_2$ incubator.

Dosing Treatment 10 mM stocking solution was prepared by dissolving each tested compound in DMSO. A series of 4× serial gradient dilutions were prepared with the stocking solution and DMSO, followed by being diluted with medium to be 10-fold dilutions respectively, and a 10-fold solution of Enzalutamide was prepared meanwhile. Enzalutamide and the equivalent volume of corresponding solution of the tested compound were added to each well for each cell line respectively, and a duplicate well was set for each drug concentration. The final concentrations of Enzalutamide and the tested compound used in the test are shown in Table 13. The final concentration of DMSO per well was 0.2%. The cells were incubated for 5 days in a 37° C., 5% $CO_2$ incubator.

Detection

After 5 days' drug treatment, the cell supernatant of each well was collected, and centrifuged at 2000 r/min for 5 minutes, then transferred to a clean EP tube for PSA detection.

5. Data Analysis

Calculation formula of PSA inhibition rate: $(1-(V_{sample}/V_{DMSO})) \times 100\%$. Wherein, $V_{sample}$ is the PSA reading of the drug treatment group, and $V_{DMSO}$ is the average value of PSA of the solvent control group.

TABLE 13

PSA inhibition rate (%): 0.5 µM Enzalutamide used alone, and in combination with different concentrations of the tested compound

| Concentration of the tested compound (µM) | 100 | 25 | 6.25 | 1.56 | 0.39 | 0.10 | 0.02 | 0.01 |
|---|---|---|---|---|---|---|---|---|
| Enzalutamide (0.5 µM) + B105 | 66.4 | 67.7 | 66.7 | 65.1 | 62.7 | 60.4 | 50.6 | 44 |
| Enzalutamide (0.5 µM) + C111 | 68 | 57.3 | 58.8 | 60.6 | 58.6 | 52.8 | 55.3 | 51.7 |

PSA inhibition rate was 30.7% when Enzalutamide (0.5 µM) was used alone

Notes of Table 13: The PSA inhibition rate was 30.7% when 0.504 Enzalutamide was used alone. The PSA inhibition rates were 60.4% and 52.8% when 0.504 Enzalutamide was used in combination with 0.1 µM B105 and C111 respectively. It can be seen that the effect of drug combination was significantly enhanced compared with Enzalutamide used alone.

Effect Embodiment 3

Referring to the method of Effect embodiment 1, the Vcap cells were replaced by LNCap cells (androgen receptor (+) prostate cancer cells) (ATCC, catalog number CRL-1740), and the results were as follows:

TABLE 14

Survival rate of LNCap cells: tested compound alone, tested compound in combination with Enzalutamide or ARN-509

| tested compound | tested compound alone | | | in combination with 1 µM Enzalutamide | | | in combination with 1 µM ARN-509 | | |
|---|---|---|---|---|---|---|---|---|---|
| | 10 µM | 1 µM | 0.1 µM | 10 µM | 1 µM | 0.1 µM | 10 µM | 1 µM | 0.1 µM |
| Enzalutamide | 59.3% | 70.5% | 101.5% | | | | | | |
| ARN-509 | 60.2% | 86.7% | 105.2% | | | | | | |
| B101 | 42.4% | 63.0% | 99.6% | 27.1% | 34.1% | 59.3% | 32.4% | 46.3% | 86.7% |
| B105 | 40.8% | 61.5% | 102.9% | 25.8% | 32.0% | 57.5% | 32.4% | 44.7% | 82.6% |

Notes of table 14: The effect of the drug combination was outstanding, for example, the cell survival rates were 63%, 61.5%, 70.5% and 86.7% when B101, B105, enzalutamide and ARN-509 were used alone respectively at 1.0 µM. The cell survival rates were 34.1% and 32% when 1.0 µM B101 or B105 was used in combination with 1.0 µM enzalutamide respectively. The cell survival rates were 46.3% or 44.7% when 1.0 µM B101 or B105 was used in combination with 1.0 µM ARN-509 respectively.

TABLE 15

Survival rate of LNCap cells: tested compound alone, tested compound in combination with Galeterone or Abiraterone acetate

| tested compound | tested compound alone | | | in combination with 1 µM Galeterone | | | in combination with 1 µM Abiraterone acetate | | |
|---|---|---|---|---|---|---|---|---|---|
| | 10 µM | 1 µM | 0.1 µM | 10 µM | 1 µM | 0.1 µM | 10 µM | 1 µM | 0.1 µM |
| B101 | 42.4% | 63.0% | 99.6% | 31.4% | 43.6% | 76.3% | 33.2% | 46.2% | 82.4% |
| B105 | 40.8% | 61.5% | 102.9% | 30.6% | 40.6% | 73.4% | 31.7% | 47.9% | 83.7% |
| Galeterone | 24.2% | 79.0% | 104.9% | | | | | | |
| Abiraterone acetate | 45.2% | 90.7% | 109.2% | | | | | | |

Notes of table 15: The effect of the drug combination was outstanding, for example, the cell survival rates were 63%, 61.5%, 79% and 90.7% when B101, B105, Galeterone and Abiraterone acetate were used alone respectively at 1.0 µM. The cell survival rates were 43.6% and 40.6% when 1.0 µM B101 or B105 was used in combination with 1.0 µM Galeterone respectively. The cell survival rates were 46.2% and 47.9% when 1.0 µM B101 or B105 was used in combination with 1.0 µM Abiraterone acetate respectively.

TABLE 16

Survival rate of LNCap cells: B105 in combination with Enzalutamide, ARN-509, Prednisone, Galeterone, or Abiraterone acetate respectively

| Drug combination | Enzalutamide (0.1, 1.0, 10 μM) | ARN-509 (0.1, 1.0, 10 μM) | B105 (1 μM) | Prednisone (1 μM) | Galeterone (1 μM) | Abiraterone acetate (1 μM) | Cell survival rate (10 μM) | Cell survival rate (1 μM) | Cell survival rate (1 μM) |
|---|---|---|---|---|---|---|---|---|---|
| 3-drug combination | | | v | v | v | | | 44.5% | |
| 3-drug combination | | | v | v | | v | | 48.2% | |
| 3-drug combination | v | | | v | v | | 51.5% | 55.7% | 68.8% |
| 3-drug combination | v | | | v | | v | 51.4% | 56.7% | 69.9% |
| 3-drug combination | v | | v | | v | | 26.2% | 28.8% | 30.3% |
| 3-drug combination | v | | v | | | v | 26.6% | 29.0% | 31.6% |
| 3-drug combination | v | | v | v | | | 28.4% | 30.8% | 41.0% |
| 4-drug combination | v | | v | v | v | | 25.2% | 26.8% | 29.5% |
| 4-drug combination | v | | v | v | | v | 26.5% | 28.6% | 32.8% |
| 3-drug combination | | v | | v | v | | 54.3% | 65.7% | 75.7% |
| 3-drug combination | | v | | v | | v | 51.3% | 66.9% | 77.4% |
| 3-drug combination | | v | v | | v | | 27.3% | 30.9% | 31.4% |
| 3-drug combination | | v | v | | | v | 26.1% | 30.8% | 35.5% |
| 3-drug combination | | v | v | v | | | 26.7% | 35.1% | 46.0% |
| 4-drug combination | | v | v | v | v | | 26.5% | 30.6% | 37.4% |
| 4-drug combination | | v | v | v | | v | 26.5% | 31.2% | 36.6% |

"V" refers to the components contained in the combination. The blank indicates the component was not contained. The same below.

Notes of table 16: The effect of the drug combination was outstanding, for example, the cell survival rate was 56.7% when 1.0 μM Enzalutamide was used in combination with 1.0 μM Prednisone and 1.0 μM Abiraterone acetate. The cell survival rate decreased to 28.6% when 1.0 μM Enzalutamide was used in combination with 1.0 μM Prednisone and 1.0 μM Abiraterone acetate and 1.0 μM B105. The cell survival rate was 55.7% when 1.0 μM Enzalutamide was used in combination with 1.0 μM Prednisone and 1.0 μM Galeterone. The cell survival rate decreased to 26.8% when 1.0 μM Enzalutamide was used in combination with 1.0 μM Prednisone and 1.0 μM Galeterone and 1.0 μM B105.

TABLE 17

Survival rate of LNCap cells: B101 in combination with Enzalutamide, ARN-509, Prednisone, Galeterone, or Abiraterone acetate respectively

| Drug combination | Enzalutamide (0.1, 1.0, 10 μM) | ARN-509 (0.1, 1.0, 10 μM) | B105 (1 μM) | Prednisone (1 μM) | Galeterone (1 μM) | Abiraterone acetate (1 μM) | Cell survival rate (10 μM) | Cell survival rate (1 μM) | Cell survival rate (1 μM) |
|---|---|---|---|---|---|---|---|---|---|
| 3-drug combination | | | v | v | v | | | 43.5% | |
| 3-drug combination | | | v | v | | v | | 49.8% | |
| 3-drug combination | v | | | v | v | | 50.6% | 53.4% | 64.0% |
| 3-drug combination | v | | | v | | v | 50.5% | 57.6% | 69.5% |
| 3-drug combination | v | | v | | v | | 26.9% | 28.6% | 31.6% |
| 3-drug combination | v | | v | | | v | 27.4% | 28.4% | 33.8% |
| 3-drug combination | v | | v | v | | | 28.3% | 29.3% | 41.6% |
| 4-drug combination | v | | v | v | v | | 24.2% | 26.6% | 31.3% |

TABLE 17-continued

Survival rate of LNCap cells: B101 in combination with Enzalutamide, ARN-509, Prednisone, Galeterone, or Abiraterone acetate respectively

| Drug combination | Enzalu- tamide (0.1, 1.0, 10 μM) | ARN-509 (0.1, 1.0, 10 μM) | B105 (1 μM) | Pred- nisone (1 μM) | Gale- terone (1 μM) | Abira- terone acetate (1 μM) | Cell survival rate (10 μM) | Cell survival rate (1 μM) | Cell survival rate (1 μM) |
|---|---|---|---|---|---|---|---|---|---|
| 4-drug combination | v | | v | v | | v | 25.4% | 27.5% | 32.5% |
| 3-drug combination | | v | | v | v | | 48.4% | 66.2% | 71.1% |
| 3-drug combination | | v | | v | | v | 50.1% | 71.4% | 79.0% |
| 3-drug combination | | v | v | | v | | 27.4% | 32.4% | 36.7% |
| 3-drug combination | | v | v | | | v | 26.6% | 32.6% | 36.9% |
| 3-drug combination | | v | v | v | | | 26.2% | 36.8% | 47.4% |
| 4-drug combination | | v | v | v | v | | 25.1% | 28.0% | 32.5% |
| 4-drug combination | | v | v | v | | v | 25.7% | 31.5% | 38.4% |

"V" refers to the components contained in the combination. The blank indicates the component was not contained.

Notes of table 17: The effect of the drug combination was outstanding, for example, the cell survival rate was 57.6% when 1.0 μM Enzalutamide was used in combination with 1.0 μM Prednisone and 1.0 μM Abiraterone acetate. The cell survival rate decreased to 27.5% when 1.0 μM Enzalutamide was used in combination with 1.0 μM Prednisone and 1.0 μM Abiraterone acetate and 1.0 μM B101. The cell survival rate was 53.4% when 1.0 μM Enzalutamide was used in combination with 1.0 μM Prednisone and 1.0 μM Galeterone. The cell survival rate decreased to 26.6% when 1.0 μM Enzalutamide was used in combination with 1.0 μM Prednisone and 1.0 μM Galeterone and 1.0 μM B101.

Although the embodiments of the invention were described above, it will be understood by people skilled in the art that these are just examples. Many changes and modifications can be made to these embodiments without departing from the principle and essence of the present invention. Therefore, the protection scope of the present invention is defined by the claims attached.

What is claimed is:

1. A combination, comprising a benzoheterocyclic compound, a pharmaceutically acceptable salt, solvate, polymorph, co-crystal, stereoisomer, isotope compound, metabolite or prodrug thereof, and an androgen receptor pathway modulator,
    wherein the benzoheterocyclic compound is any one of the following compounds:

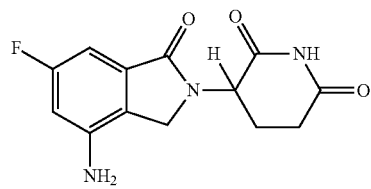
B101

-continued

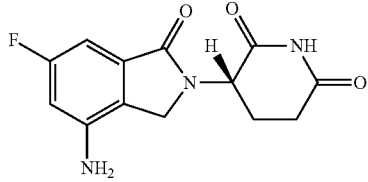
B102

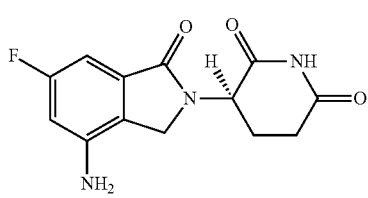
B103

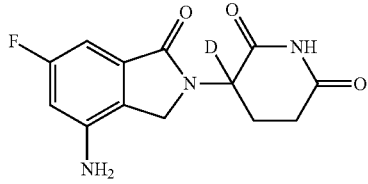
B104

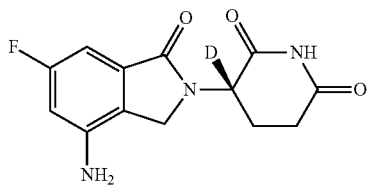
B105

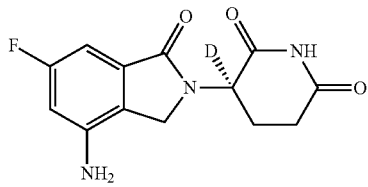
B106

-continued

C107
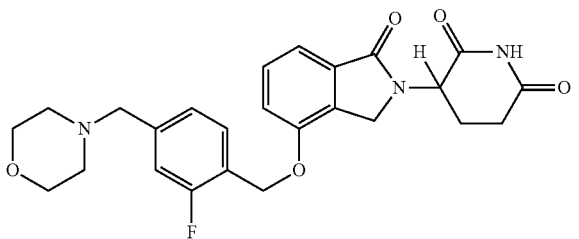

C108
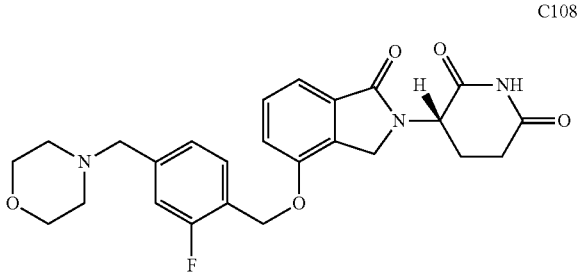

C109
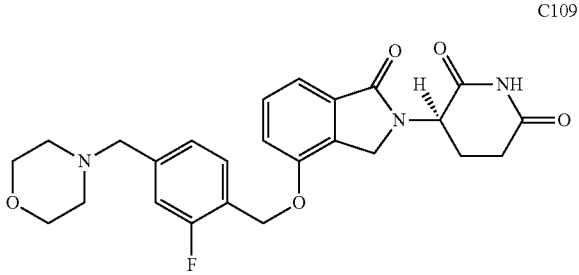

C110
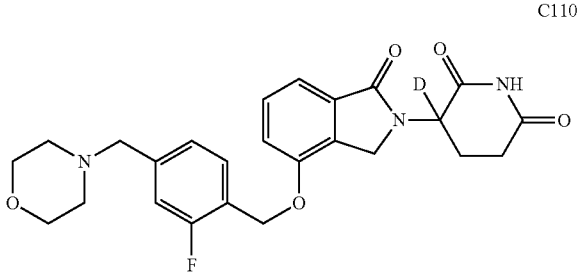

C111
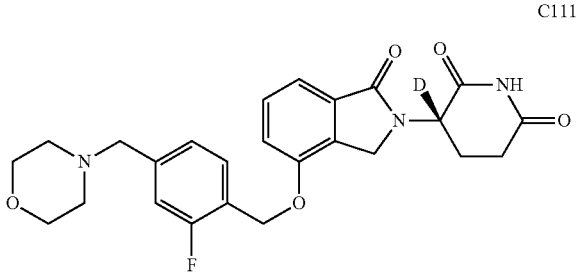

C112
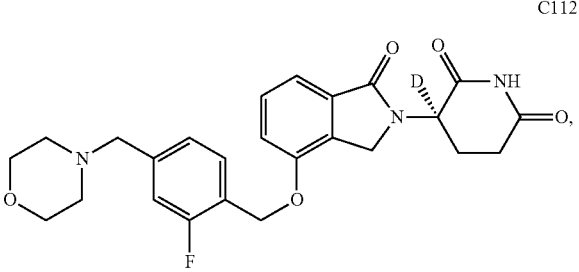

and
wherein the androgen receptor pathway modulator is selected from one or more of Enzalutamide, ARN-509, Abiraterone acetate, Galeterone, and ODM-201.

2. The combination according to claim 1, wherein the androgen receptor pathway modulator is Enzalutamide, ARN-509, Galeterone, ODM-201, Abiraterone acetate, Enzalutamide and Galeterone, Enzalutamide and Abiraterone acetate, Enzalutamide and ODM-201, ARN-509 and Galeterone, ARN-509 and Abiraterone acetate, ARN-509 and ODM-201, or ODM-201 and Abiraterone acetate.

3. The combination according to claim 1, wherein the combination of the benzoheterocyclic compound and the androgen receptor pathway modulator is B101 and Enzalutamide, B102 and Enzalutamide, B103 and Enzalutamide, B104 and Enzalutamide, B105 and Enzalutamide, B106 and Enzalutamide, C111 and Enzalutamide, B101 and ARN-509, B102 and ARN-509, B103 and ARN-509, B104 and ARN-509, B105 and ARN-509, B106 and ARN-509, C111 and ARN-509, B101 and Abiraterone acetate, B105 and Abiraterone acetate, C111 and Abiraterone acetate, B101 and Galeterone, B105 and Galeterone, C111 and Galeterone, B101 and ODM-201, B105 and ODM 201, C111 and ODM-201, B101 and Enzalutamide and Galeterone, B105 and Enzalutamide and Galeterone, C111 and Enzalutamide and Galeterone, B101 and Enzalutamide and Abiraterone acetate, B105 and Enzalutamide and Abiraterone acetate, C111 and Enzalutamide and Abiraterone acetate, B101 and ARN-509 and Galeterone, B105 and ARN-509 and Galeterone, C111 and ARN-509 and Galeterone, B101 and ARN-509 and Abiraterone acetate, B105 and ARN-509 and Abiraterone acetate, or C111 and ARN-509 and Abiraterone acetate.

4. The combination according to claim 1, wherein the combination further comprises a hormone compound, and the hormone compound is prednisone.

5. The combination according to claim 4, wherein the combination of the androgen receptor pathway modulator and the hormone compound is Galeterone and prednisone, prednisone and Abiraterone acetate, Enzalutamide and prednisone, ARN-509 and prednisone, Enzalutamide and Galeterone and prednisone, Enzalutamide and Abiraterone acetate and prednisone, ARN-509 and Galeterone and prednisone, or ARN-509 and Abiraterone acetate and prednisone.

6. The combination according to claim 4, wherein the combination of the benzoheterocyclic compound, the androgen receptor pathway modulator and the hormone compound is B101 and Enzalutamide and prednisone, B105 and Enzalutamide and prednisone, C111 and Enzalutamide and prednisone, B101 and ARN-509 and prednisone, B105 and ARN-509 and prednisone, C111 and ARN-509 and prednisone, B101 and Galeterone and prednisone, B105 and Galeterone and prednisone, C111 and Galeterone and prednisone, B101 and prednisone and Abiraterone acetate, B105 and prednisone and Abiraterone acetate, C111 and prednisone and Abiraterone acetate, B101 and Enzalutamide and Galeterone and prednisone, B105 and Enzalutamide and Galeterone and prednisone, C111 and Enzalutamide and Galeterone and prednisone, B101 and Enzalutamide and Abiraterone acetate and prednisone, B105 and Enzalutamide and Abiraterone acetate and prednisone, C111 and Enzalutamide and Abiraterone acetate and prednisone, B101 and ARN-509 and Galeterone and prednisone, B105 and ARN-509 and Galeterone and prednisone, C111 and ARN-509 and Galeterone and prednisone, B101 and ARN-509 and Abiraterone acetate and prednisone, B105 and ARN-509 and Abiraterone acetate and prednisone, or C111 and ARN-509 and Abiraterone acetate and prednisone.

7. A pharmaceutical composition, comprising the combination according to claim 1 and one or more pharmaceutically acceptable excipients.

8. A method of treatment of prostate cancer, comprising administrating a therapeutically effective amount of the combination according to claim 1 to the patients in need.

9. The method according to claim 8, wherein the benzoheterocyclic compound, the pharmaceutically acceptable salt, solvate, polymorph, co-crystal, stereoisomer, isotope compound, metabolite or prodrug thereof and the androgen receptor pathway modulator are administered simultaneously or separately;
and/or, the prostate cancer is castration-resistant prostate cancer.

10. A kit, comprising a pharmaceutical composition A and a pharmaceutical composition B;
wherein the pharmaceutical composition A comprises the benzoheterocyclic compound, the pharmaceutically acceptable salt, solvate, polymorph, co-crystal, stereoisomer, isotope compound, metabolite or prodrug thereof and one or more pharmaceutically acceptable excipients;
the pharmaceutical composition B comprises the androgen receptor pathway modulator and one or more pharmaceutically acceptable excipients;
the benzoheterocyclic compound, the pharmaceutically acceptable salt, solvate, polymorph, co-crystal, stereoisomer, isotope compound, metabolite or prodrug thereof; and the androgen receptor pathway modulator are as defined in claim 1.

11. The kit according to claim 10, further comprising a pharmaceutical composition C, which comprises a hormone compound and one or more pharmaceutically acceptable excipients, wherein the hormone compound is prednisone
and/or, the pharmaceutical compositions in the kit are administered simultaneously or separately;
and/or, the kit is used for treatment of prostate cancer.

12. The kit according to claim 11, wherein the combination of the benzoheterocyclic compound, the pharmaceutically acceptable salt, solvate, polymorph, co-crystal, stereoisomer, isotope compound, metabolite or prodrug thereof in pharmaceutical composition A, the androgen receptor pathway modulator in pharmaceutical composition B and the hormone compound in pharmaceutical composition C is: B101 and Enzalutamide and prednisone, B105 and Enzalutamide and prednisone, C111 and Enzalutamide and prednisone, B101 and ARN-509 and prednisone, B105 and ARN-509 and prednisone, C111 and ARN-509 and prednisone, B101 and Galeterone and prednisone, B105 and Galeterone and prednisone, C111 and Galeterone and prednisone, B101 and prednisone and Abiraterone acetate, B105 and prednisone and Abiraterone acetate, C111 and prednisone and Abiraterone acetate, B101 and Enzalutamide and Galeterone and prednisone, B105 and Enzalutamide and Galeterone and prednisone, C111 and Enzalutamide and Galeterone and prednisone, B101 and Enzalutamide and Abiraterone acetate and prednisone, B105 and Enzalutamide and Abiraterone acetate and prednisone, C111 and Enzalutamide and Abiraterone acetate and prednisone, B101 and ARN-509 and Galeterone and prednisone, B105 and ARN-509 and Galeterone and prednisone, C111 and ARN-509 and Galeterone and prednisone, B101 and ARN-509 and Abiraterone acetate and prednisone, B105 and ARN-509 and Abiraterone acetate and prednisone, or C111 and ARN-509 and Abiraterone acetate and prednisone.

13. A pharmaceutical composition, comprising the combination according to claim 4 and one or more pharmaceutically acceptable excipients.

14. A method of treatment of prostate cancer, comprising administrating a therapeutically effective amount of the combination according to claim 4 to the patients in need.

15. The method according to claim 14, wherein the benzoheterocyclic compound, the pharmaceutically acceptable salt, solvate, polymorph, co-crystal, stereoisomer, isotope compound, metabolite or prodrug thereof, the androgen receptor pathway modulator and the hormone compound are administered simultaneously or separately;
and/or, the prostate cancer is castration-resistant prostate cancer.

16. A kit, comprising a pharmaceutical composition A and a pharmaceutical composition B; wherein the combination of the benzoheterocyclic compound, the pharmaceutically acceptable salt, solvate, polymorph, co-crystal, stereoisomer, isotope compound, metabolite or prodrug thereof in the pharmaceutical composition A; and the androgen receptor pathway modulator in the pharmaceutical composition B is as defined in claim 3.

17. The kit according to claim 11, wherein the prostate cancer is castration-resistant prostate cancer.

* * * * *